US010900073B2

(12) United States Patent
Blainey et al.

(10) Patent No.: US 10,900,073 B2
(45) Date of Patent: *Jan. 26, 2021

(54) HIGH RESOLUTION SYSTEMS, KITS, APPARATUS, AND METHODS FOR HIGH THROUGHPUT MICROBIOLOGY APPLICATIONS

(71) Applicant: General Automation Lab Technologies, Inc., San Francisco, CA (US)

(72) Inventors: Paul C. Blainey, Cambridge, MA (US); Michael W. Seely, San Diego, CA (US); Roman Stocker, Zurich (CH); Karsten Zengler, Cardiff by the Sea, CA (US); Scott Conradson, Los Altos Hills, CA (US); Peter Christey, San Francisco, CA (US); Alexander Hallock, Redwood City, CA (US)

(73) Assignee: GENERAL AUTOMATION LAB TECHNOLOGIES INC., San Carlos, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 15/135,377

(22) Filed: Apr. 21, 2016

(65) Prior Publication Data
US 2016/0312275 A1 Oct. 27, 2016

Related U.S. Application Data

(60) Provisional application No. 62/299,088, filed on Feb. 24, 2016, provisional application No. 62/292,091, filed on Feb. 5, 2016, provisional application No. 62/150,677, filed on Apr. 21, 2015.

(51) Int. Cl.
| *C12Q 1/68* | (2018.01) |
| *C07H 1/00* | (2006.01) |
| *C12Q 1/6888* | (2018.01) |
| *C12Q 1/6869* | (2018.01) |
| *B01L 3/00* | (2006.01) |
| *C12Q 1/6853* | (2018.01) |
| *C12Q 1/6816* | (2018.01) |
| *C12Q 1/689* | (2018.01) |
| *C12M 1/32* | (2006.01) |
| *C12M 1/04* | (2006.01) |
| *B01L 3/02* | (2006.01) |

(52) U.S. Cl.
CPC .......... *C12Q 1/6853* (2013.01); *B01L 3/5085* (2013.01); *C12M 23/12* (2013.01); *C12M 23/24* (2013.01); *C12Q 1/689* (2013.01); *C12Q 1/6816* (2013.01); *B01L 3/0244* (2013.01); *B01L 2200/025* (2013.01); *B01L 2200/0689* (2013.01); *B01L 2200/12* (2013.01); *B01L 2200/141* (2013.01); *B01L 2300/021* (2013.01); *B01L 2300/0636* (2013.01); *B01L 2300/0681* (2013.01); *B01L 2300/0829* (2013.01); *B01L 2300/0893* (2013.01); *B01L 2300/165* (2013.01)

(58) Field of Classification Search
CPC ...... C12Q 1/68; C12Q 1/6888; C12Q 1/6869; C12Q 1/689; C07H 21/00; B01L 5/5085
See application file for complete search history.

(56) References Cited

U.S. PATENT DOCUMENTS

| 4,634,676 | A |  | 1/1987 | Sapatino |  |
|---|---|---|---|---|---|
| 4,717,667 | A | * | 1/1988 | Provonchee | ........... C12M 23/04 435/30 |
| 4,770,856 | A | * | 9/1988 | Uthemann | ............ B01L 3/5085 422/22 |
| 5,061,621 | A |  | 10/1991 | Perlman |  |
| 5,587,322 | A |  | 10/1996 | Chrebet |  |
| 5,858,770 | A |  | 1/1999 | Perlman |  |
| 5,882,922 | A |  | 3/1999 | Tyndorf |  |
| 6,083,724 | A |  | 7/2000 | Lowenthal |  |
| 6,103,479 | A |  | 8/2000 | Taylor |  |
| 6,174,673 | B1 |  | 1/2001 | Short |  |
| 6,509,168 | B2 |  | 1/2003 | Croteau |  |

(Continued)

FOREIGN PATENT DOCUMENTS

| EP | 2805769 A1 | 11/2014 |
|---|---|---|
| WO | 2005052582 A2 | 6/2005 |

(Continued)

OTHER PUBLICATIONS

Jung et al. Clinica Chimica Acta 411:1611 (Year: 2010).*
Burns et al.,A novel approach for high throughput cultivation assays and the isolation of planktonic bacteria FEMS Microbiol Ecol. 45 :161-171 (2003).*
Button et al. Viability and isolation of marine bacteria by dilution culture: theory, procedures, and initial results. Appl. Environ Microbiol. 59 :881-891 (1993).*
Collado et al. High-throughput culturing of fungi from plant litter by a dilution-to-extinction techniqueFEMS Microbioloical Ecology 60 : 521-533 (Year: 2007).*

(Continued)

*Primary Examiner* — Ethan C Whisenant
(74) *Attorney, Agent, or Firm* — Lin Sun-Hoffman; Yong Chen; Liu Chen & Hoffman LLP

(57) ABSTRACT

A microfabricated device defining a high density array of microwells is described for cultivating cells from a sample. A series of unique tags may be disposed in the microwells to identify one or more species of cells and locate the particular microwells in which each species was cultivated. A unique tag may be a nucleic acid molecule including a target-specific nucleotide sequence for annealing to a target nucleic acid fragment and a location-specific nucleotide sequence predetermined to identify one or more microwells. The device may be incubated to grow a plurality of cells, which may be split into an analysis portion and a reserve portion. High throughput methods are described for cultivating, screening, and determining a relative and/or absolute abundance of cells from a sample.

24 Claims, 21 Drawing Sheets

Specification includes a Sequence Listing.

(56) References Cited

U.S. PATENT DOCUMENTS

| | | |
|---|---|---|
| 6,900,055 B1 | 5/2005 | Fuller |
| 6,951,714 B2 | 10/2005 | Giovannoni |
| 6,972,183 B1 | 12/2005 | Lafferty |
| 7,011,957 B2 | 3/2006 | Kim |
| 7,019,827 B2 | 3/2006 | Lafferty |
| 7,195,872 B2 | 3/2007 | Agrawal |
| 7,419,778 B2 | 9/2008 | Van Damme |
| 9,228,933 B2 | 1/2016 | Joseph |
| 2002/0172993 A1 | 11/2002 | Nautiyal et al. |
| 2005/0070005 A1 | 3/2005 | Keller |
| 2005/0147959 A1* | 7/2005 | Frondoza ............ C12N 5/0655 435/2 |
| 2005/0255445 A1 | 11/2005 | Van Damme |
| 2005/0266547 A1 | 12/2005 | Scherze |
| 2007/0026516 A1 | 2/2007 | Martin |
| 2007/0072187 A1 | 3/2007 | Blok |
| 2008/0206831 A1 | 8/2008 | Coffey |
| 2009/0298153 A1 | 12/2009 | Martin |
| 2010/0021959 A1 | 1/2010 | Ingham |
| 2010/0152054 A1* | 6/2010 | Love .................. B82Y 30/00 506/9 |
| 2011/0160067 A1 | 6/2011 | Sundstrom et al. |
| 2011/0294208 A1 | 12/2011 | Allbritton |
| 2013/0052649 A1 | 2/2013 | Lee |
| 2013/0065795 A1 | 3/2013 | Allbritton |
| 2013/0295551 A1 | 11/2013 | Eddington |
| 2014/0227684 A1 | 8/2014 | Hindson |
| 2014/0303354 A1* | 10/2014 | Masternak ......... C07K 16/2803 530/387.3 |
| 2014/0304846 A1* | 10/2014 | Heron ................ C07K 14/705 800/16 |
| 2015/0057163 A1 | 2/2015 | Rotem |
| 2015/0118707 A1 | 4/2015 | Selvaganapathy |
| 2015/0141261 A1 | 5/2015 | Hunicke-Smith |
| 2015/0204862 A1 | 7/2015 | Fan |
| 2015/0299784 A1 | 10/2015 | Fan |
| 2016/0122753 A1 | 5/2016 | Mikkelsen |
| 2016/0244825 A1 | 8/2016 | Vigneault |
| 2016/0245805 A1 | 8/2016 | Baer |
| 2016/0250632 A1 | 9/2016 | Hong |
| 2016/0264919 A1 | 9/2016 | Kabaha |
| 2017/0198275 A1 | 7/2017 | Lee |
| 2017/0247652 A1 | 8/2017 | Goluch |
| 2017/0307606 A1 | 10/2017 | Hallock |
| 2017/0362554 A1 | 12/2017 | Martin |
| 2017/0362569 A1 | 12/2017 | Valamehr |
| 2017/0363545 A1 | 12/2017 | Halverson |

FOREIGN PATENT DOCUMENTS

| | | |
|---|---|---|
| WO | WO2014028537 | 2/2014 |
| WO | WO2015031691 | 3/2015 |

OTHER PUBLICATIONS

Gich et al., Specific Detection, Isolation, and Characterization of Selected, Previously Uncultured Members of the Freshwater Bacterioplankton Community. Appl. Environ Microbiol. 71 : 5908-5919 (2005).*

Hadelsman, Jo., Metagenomics: Application of Genomics to Uncultured Microorganisms. Microbiology and Molecular Biolody Reviews 68(4) : 669-685 (Year: 2004).*

Page et al., Representative Freshwater Bacterioplankton Isolated from Crater Lake, Oregon Appl. Environ Microbiol. 70 : 6542-6550 (2004).*

Simu et al., Oligotrophic Bacterioplankton with a Novel Single-Cell Life Strategy. Appl. Environ Microbiol. 70 : 2445-2451 (2004).*

International Search Report and Written Opinion for WO2016172362.

Connon, et al., High-Throughput Methods for Culturing Microorganisms in Very-Low-Nutrient Media Yield Diverse New Marine Isolates, Applied and Environmental Microbiology, Aug. 2002, p. 3878-3885.

Zengler, et al., Cultivating the uncultured, PNAS, 2002, vol. 99, No. 24, p. 15681-15686.

Stevenson, et al., New Strategies for Cultivation and Detection of Previously Uncultured Microbes, Applied and Environmental Microbiology, 2004, p. 4748-4755.

Laffert, et al., GigaMatrixTM: An Ultra High-Throughput Tool for Accessing Biodiversity, Journal of Association for Laboratory Automation, Aug. 2004, p. 200-208.

Ingham, et al., The micro-Petri dish, a million-well growth chip for the culture and high-throughput screening of microorganisms, PNAS, 2007, vol. 104, No. 46, p. 18217-18222.

Bollmann, et al., Incubation of Environmental Samples in a Diffusion Chamber Increases the Diversity of Recovered Isolates, Applied and Environmental Microbiology, Oct. 2007, p. 6386-6390.

Miller, et al., "Basic Concepts of Microarrays and Potential Applications in Clinical Microbiology", Clinical Microbiology Reviews, Oct. 2009, p. 611-633.

Nichols, et al., Use of Ichip for High-Throughput In Situ Cultivation of "Uncultivable" Microbial Species, Applied and Environmental Microbiology, 2010, p. 2445-2450.

Vartoukian, et al., Strategies for culture of 'unculturable' bacteria, FEMS Microbiol Lett 2010,309, p. 1-7.

Jung, et al., Cell-free DNA in the blood as solid tumor biomarker—A Critical appraisal of the literature, Clinica Chimica Acta, 2010,411, p. 1611-1624.

Lecomte, et al., Isolation and identification of soil bacteria growing at the expense of arbuscular mycorrhizal fungi, FEMS Microbiol Lett 2011, vol. 317, p. 43-51.

Stewart, Growing Unculturable Bacteria, Journal of Bacteriology, 2012, vol. 194 No. 16 p. 4151-4160.

Ma, et al., Gene-targeted microfluidic cultivation validated by isolation of a gut bacterium listed in Human Microbiome Project's Most Wanted taxa PNAS, 2014, vol. 111, No. 27, p. 9768-9773.

Tandoga, et al., Isolation of Microorganisms Using Constrictions, PLOS ONE, 2014, vol. 9, No. 6, p. 1-7.

Chen, et al., High-throughput analysis and protein engineering using microcapillary arrays, Nature Chemical Biology, 2015 doi:10.1038/nchembio.1978.

Extended European Search Report on EP 17862455, dated Sep. 1, 2020.

Khatri, B. et al. High Throughput Phenotypic Analysis of *Mycobacterium tuberculosis* and *Mycobacterium bovis* Strains' Metabolism Using Biolog Phenotype Microarrays, Plos One, V. 8, No. 1, e52673, 2013.

Hanif, M.K. et al. Isolation and characterization of a β-propeller gene containing phosphobacterium Bacillus subtilis strain KPS-11 for growth promotion of potato (*Solanum tuberosum* L.), Frontiers in Microbiology, vol. 6, 583, 2015.

* cited by examiner

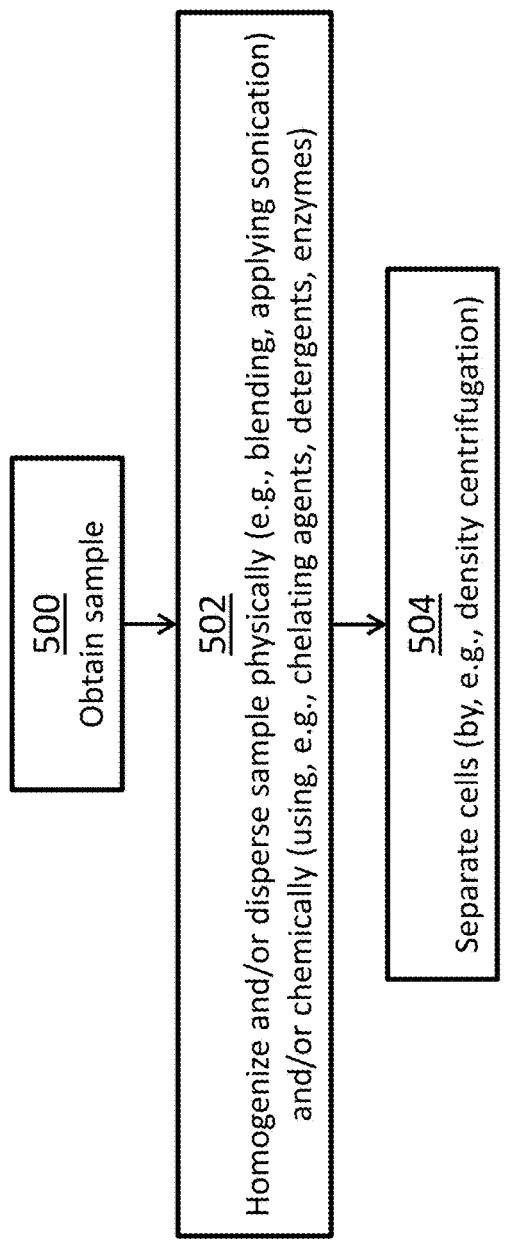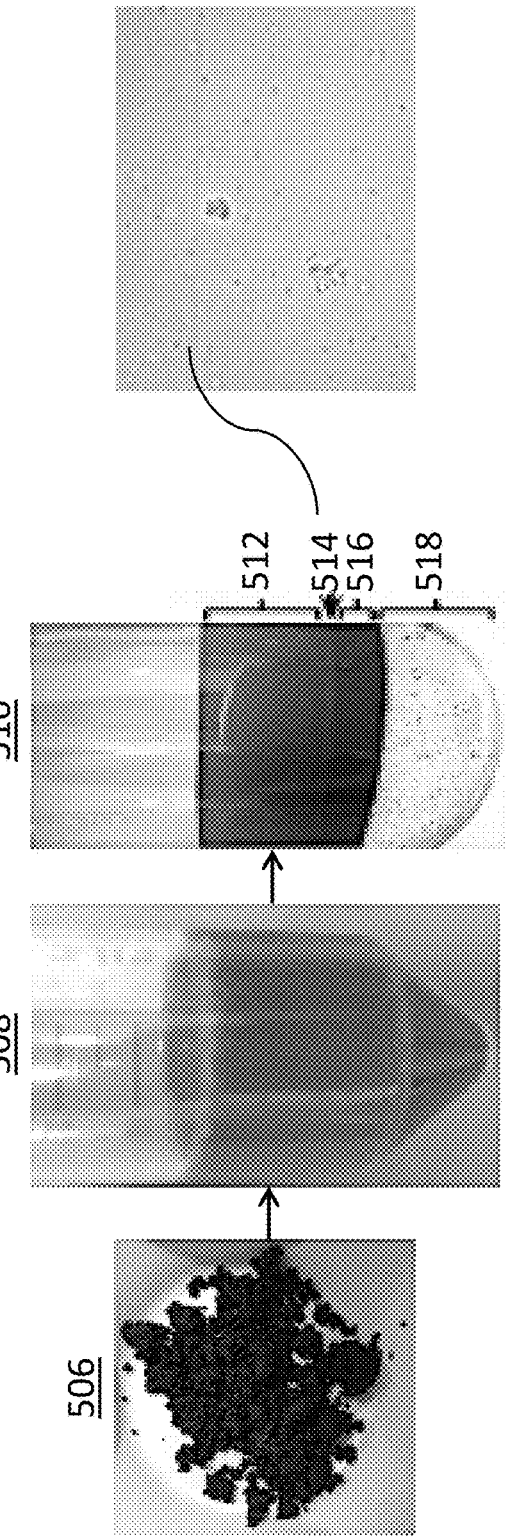

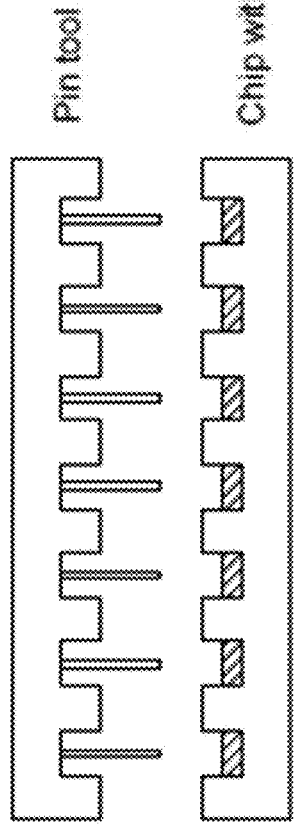
FIG. 10A
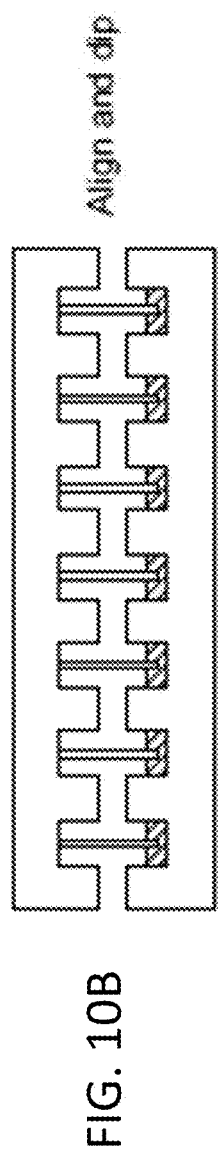
FIG. 10B
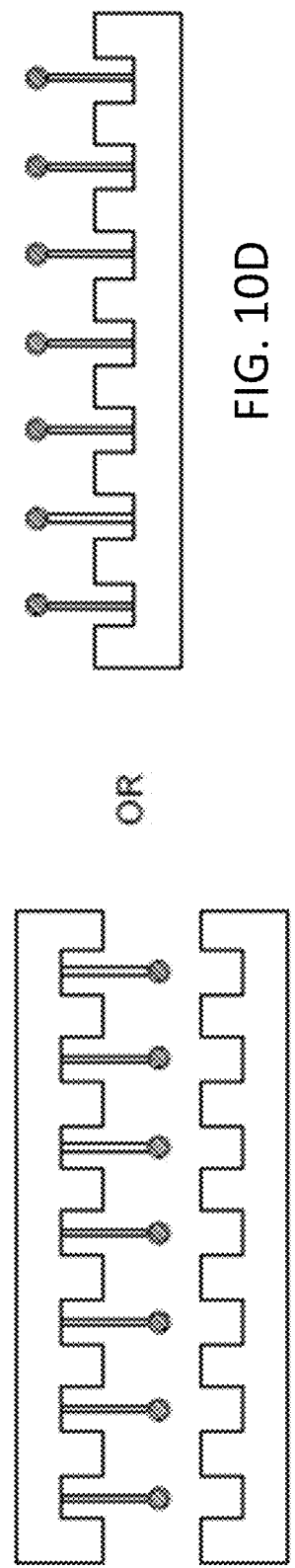
FIG. 10D
OR
FIG. 10C

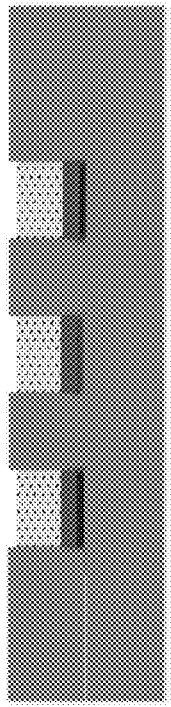
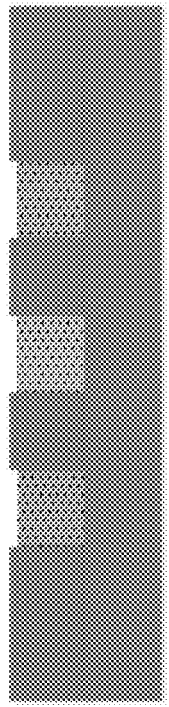
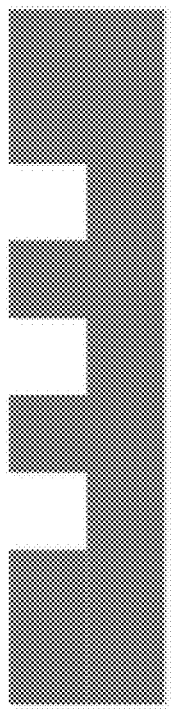

HIGH RESOLUTION SYSTEMS, KITS, APPARATUS, AND METHODS FOR HIGH THROUGHPUT MICROBIOLOGY APPLICATIONS

CROSS-REFERENCE TO RELATED APPLICATIONS

This application claims a priority benefit of U.S. Provisional Patent Application No. 62/299,088, entitled "Biobanking Cells Using High Density Microfabricated Arrays," filed on Feb. 24, 2016; U.S. Provisional Patent Application No. 62/292,091, entitled "Systems, Apparatus, and Methods for Isolation, Cultivation, Screening, and Identification of Cells," filed on Feb. 5, 2016; and U.S. Provisional Patent Application No. 62/150,677, entitled "Systems, Apparatus, and Methods for Isolation, Cultivation, Screening, and Identification of Cells," filed on Apr. 21, 2015, each of which is incorporated herein by reference in its entirety.

INCORPORATION OF SEQUENCE LISTING

This application includes a Sequence Listing which has been submitted in ASCII format via EFS-Web, named "GALT_001_01US_SeqList_ST25.txt," which is 3 KB in size (measured in Windows 7) and which was created on Jun. 23, 2016. The contents of the Sequence Listing were present in the application as originally filed and are incorporated herein by reference in their entirety.

TECHNICAL FIELD

The present disclosure relates generally to innovations in microbiology, microfabrication, chemistry, optics, robotics, and information technology. More specifically, the present disclosure relates to systems, apparatus, kits, and methods for high throughput cultivation, screening, isolation, sampling, and/or identification of biological entities and/or nutrients.

BACKGROUND

Traditional techniques and tools for cultivating biological entities from environmental and other samples are often slow, laborious, and expensive. Even with these techniques and tools, often cells and other biological entities still defy all attempts at culture, resulting in missed information and/or product opportunities. Likewise, the screening of a population of biological entities for a particular metabolite, enzyme, protein, nucleic acid, phenotype, mutation, metabolic pathway, gene, adaptation, capability, and/or therapeutic benefit is challenging, requiring complex and expensive methods. For example, microbes live in extremely high-risk environments. To survive, microbes have developed amazing sets of biochemical tools, including novel enzymes, unique metabolites, innovative genetic pathways, and strategies for manipulating their environment and their microbial neighbors—powerful solutions that could lead to new insights and products ranging from life-saving antibiotics to fertilizers that improve food production and security.

SUMMARY

The present disclosure provides microbiology systems, apparatus, kits, and methods for streamlining the cultivation workflow, supporting high throughput screening, and/or developing new insights and products in accordance with some embodiments. For example, an apparatus may comprise a microfabricated device for receiving a sample comprising one or more cells. The microfabricated device defines a high density array of microwells for cultivating one or more cells.

In some embodiments, a device with a high density array of microwells for cultivating cells may be provided. In further embodiments, a set of unique tags may be provided for disposal into each microwell or some of the microwells. Alternatively, the device may be provided with the unique tags already seeded into each microwell or some of the microwells. The device and/or the unique tags may be provided alone or part of a kit. For example, a kit may include a microfabricated device for receiving a sample comprising one or more cells, the microfabricated device defining a high density array of microwells for cultivating the cell(s). A kit also may include a set of unique tags for disposing in the microwells so as to identify the specific microwell in which a species of cell is cultivated. One or more unique tags may be disposed in each microwell of the high density array of microwells. A kit further may include instructions for seeding microwells with unique tags and/or using the unique tags to trace cultivated cells back to the specific microwell in which they were cultivated.

In some embodiments, a unique tag may include a nucleic acid molecule with a target-specific nucleotide sequence for annealing to a target nucleic acid fragment of a cell or a particular species of cell (e.g., an organism) that may be present in a microwell and a location-specific nucleotide sequence for identifying the microwell itself. More than one unique tag may be disposed in a particular microwell such that more than one location-specific nucleotide sequence is present in the particular microwell. That is, the location-specific nucleotide sequences may be found in more than one microwell (e.g., predetermined to identify a dimension of microwells in the high density array of microwells), and the unique tags may be multi-dimensional. For example, a set of unique tags may be two-dimensional, including tags with a first location-specific nucleotide sequence predetermined to identify a first dimension of microwells (e.g., a row) in a high density array of microwells and tags with a second location-specific nucleotide sequence predetermined to identify a second dimension of microwells (e.g., a column) in the high density array of microwells. Together, the first location-specific nucleotide sequence and the second location-specific nucleotide sequence identify a specific microwell of the high density array of microwells. Thus, the combination of unique tags in a particular microwell operates to identify that microwell.

In some embodiments, one or more nutrient may be provided for growing and/or screening cells within each or some of the microwells of a device including a high density array of microwells for cultivating cells. One or more nutrients may be provided for disposal in all or some of the microwells (e.g., directly in a microwell, through a membrane, and/or on a permeable or semi-permeable membrane. Alternatively, the device may be provided with one or more nutrients already disposed in each microwell or some of the microwells. A nutrient may be provided alone, as part of a medium, and/or as part of a kit. A kit may include instructions for providing one or more nutrients to cells being cultivated within specific microwells in the device. For example, a kit further may include at least one nutrient for cultivating the at least one species of the at least one cell. The at least one nutrient for cultivating the at least one species of the at least one cell may include or be a component of an extract from a natural environment of the at least one species of the at least one cell, a medium derived from the natural environment of the at least one species of the at least one cell, a medium formulated to resemble the natural environment of the at least one species of the at least one cell, a selective medium to cultivate only the at least one species of the at least one cell, and/or a differential medium to distinguish the at least one species of the at least one cell. The natural environment of the at least one species of the at least one cell may be a biological tissue, a biological product, a microbial suspension, air, soil, sediment, living organic matter, forage, petroleum, sewage, and/or water.

In some embodiments, a membrane may be provided for keeping cells within each or some of the microwells (e.g., preventing cross-contamination) of a device including a high density array of microwells for cultivating cells. A membrane may be applied to seal some or all of the microwells. Alternatively, the device may be provided with the membrane already sealed over some or all of the microwells. A membrane may be, for example, impermeable, permeable only by gas, or allow for diffusion of one or more nutrients into one or more microwells. The device and/or the membrane may be provided alone or as part of a kit. For example, a kit may include a microfabricated device for receiving a sample comprising at least one cell. A kit also may include a membrane to retain the at least one cell in the at least one microwell of the high density array of microwells after the sample is loaded on the microfabricated device. A kit further may include instructions for loading microwells with a sample and/or using the membrane keep cultivated cells within the specific microwells in which they were cultivated.

In some embodiments, steps are provided for cultivating cells using a device with a high density array of microwells for cultivating cells. For example, a method may include obtaining a microfabricated device defining a high density array of microwells for cultivating at least one cell from a sample, which may include disposing at least one unique tag in at least one microwell of the high density array of microwells, loading the device with a sample including one or more cells, and/or applying a membrane to all or a portion of the device to retain the cells in their respective microwells. In some embodiments, a sample is prepared before loading. For example, a sample may be diluted such that no more than one cell is disposed in each microwell of a preponderance of the high density array of microwells. A method also may include incubating a device to grow a plurality of cells from the at least one cell in the at least one microwell of the high density array of microwells.

In some embodiments, steps are disclosed for replicating and/or splitting cells cultivated in a high density array of microwells such that a portion of the cells may be modified and/or destroyed for analysis (e.g., amplified and sequenced) whereas the remaining cells may be reserved for future sampling and/or use based on the information gleaned from the analysis. For example, a method may include splitting a plurality of cells in the at least one microwell of the high density array of microwells into a first portion of the plurality of cells and a second portion of the plurality of cells. The at least one unique tag may remain with at least the first portion of the plurality of cells. Splitting the plurality of cells in the at least one microwell of the high density array of microwells may include removing the membrane from the at least one microwell of the high density array of microwells such that some of the cells remain in the at least one microwell of the high density array of microwells and some of the cells remain on the membrane. Alternatively, a membrane may be temporarily peeled back to allow sampling or picked through (i.e., punctured) for sampling.

In some embodiments, steps are disclosed for analyzing all or some of the cells cultivated in a high density array of microwells. For example, a method may include analyzing a first portion of a plurality of cells to determine at least one species of interest. The cells to be analyzed may be in the same microwell in which they were cultivated, attached to a membrane that was covering the microwell in which they were cultivated, and/or transferred to another location (e.g., a petri dish or a second device with a corresponding high density array of microwells). Analysis may include determining a presence or an absence of at least one species of interest, which may be selected based on at least one of a nucleic acid and a gene. For example, a polymerase chain reaction (PCR) may be performed to amplify any of the target nucleic acid fragments present in the cells based on the target-specific nucleotide sequence of the at least one unique tag. Analysis may further comprise the step of sequencing any PCR-amplified target nucleic acid fragments using next generation sequencing (NGS) or any other type of sequencing. Sequencing may be used to identify a species of cell (e.g., an organism) and/or one or more locations in the original high density array of microwells at which the species of cell was cultivated.

In some embodiments, steps are disclosed for identifying and/or locating one or more microwells in a high density array of microwells in which a particular species of cell was cultivated. For example, a method may include identifying at least one microwell of the high density array of microwells in which at least one species of interest was cultivated based on at least one unique tag. Based on identifying the at least one microwell of the high density array of microwells in which the at least one species of interest was cultivated, a method may include locating the at least one species of interest within the second portion of the plurality of cells.

In some embodiments, steps are disclosed for picking or sampling one or more microwells in a high density array of microwells in which a plurality of cells were cultivated. For example, a method may include picking at least one cell from a particular microwell or a membrane location correlated to the particular microwell. Devices and methods are described for picking from more than one microwell simultaneously.

In some embodiments, methods are disclosed for screening cells using a device with a high density array of microwells for cultivating cells. For example, a method may include screening cells cultivated in a high density array of microwells to determine a presence or an absence of a species of interest. If present, the method may include picking one or more cells of the species of interest from one or more microwells in which the cells were cultivated. A method may include performing an assay based on a metabolite, a metabolic pathway, an enzyme, a protein, a nucleic acid, a phenotype, a gene, a mutation, an adaptation, and/or a capability of the cells. If unique tags were utilized, a method may include using one or more location-specific nucleotide sequences to identify one or more microwells in which a species of interest was cultivated. For example, a target nucleic acid fragment may be present in the species of interest, the target nucleic acid fragment including genetic code relating to a metabolite, a metabolic pathway, an enzyme, a protein, a nucleic acid, a phenotype, a gene, a mutation, an adaptation, and/or a capability.

In some embodiments, methods are disclosed for determining a relative abundance and/or an absolute abundance of a species of interest in a sample using a device with a high density array of microwells for cultivating cells. For example, a method may include preparing and loading a sample into microwells with a set of unique tags disposed therein, the sample prepared such that no more than one cell of the at least one cell is disposed in each microwell of a preponderance of the high density array of microwells. Following cultivation, a method may include using the tags to determine a first number of microwells with at least one cell, a second number of microwells with the species of interest, and based thereupon, a relative abundance of the at least one species of interest in the sample. A method may further include determining a total number of cells from the sample and, based on the total number and a relative abundance of at least one species of interest in the sample, an absolute abundance of the at least one species of interest in the sample.

More generally, systems, apparatus, kits, and methods are disclosed for cultivating a biological entity from a sample using a microfabricated device defining a high density array of experimental units. A biological entity may be an organism, a cell, a cell component, a cell product, and a virus. In some embodiments, more than one biological entity may be present in a sample, loaded on the device, and/or loaded in an experimental unit. An experimental unit may include one or more biological entities and/or one or more unique tags to identify spatial information relating to the particular experimental unit. A unique tag may include a binding molecule, such as a protein, a nucleic acid, a carbohydrate, a lipid, and/or a drug. For example, a unique tag may include a target-specific component for binding to a biomolecule present in a biological entity of interest. A unique tag also may include a location-specific component for identifying spatial information relating to the at least one experimental unit. The device may be incubated to grow a plurality of biological entities in the high density array of experimental units. One or more cultivated biological entities may be analyzed to identify one or more species and/or spatial information relating to one or more experimental units in which the entities were cultivated based on the at least one unique tag.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 5A is a flowchart illustrating a method for isolating cells from a sample in accordance with some embodiments. FIG. 5B is a diagram illustrating a method for isolating cells from a soil sample in accordance with some embodiments.

FIGS. 10A-10D are diagrams illustrating a tool for picking a chip in accordance with some embodiments.

FIGS. 21A-21E are diagrams illustrating a chip with well-specific chemistries in accordance with some embodiments.

DETAILED DESCRIPTION

Figure 1:
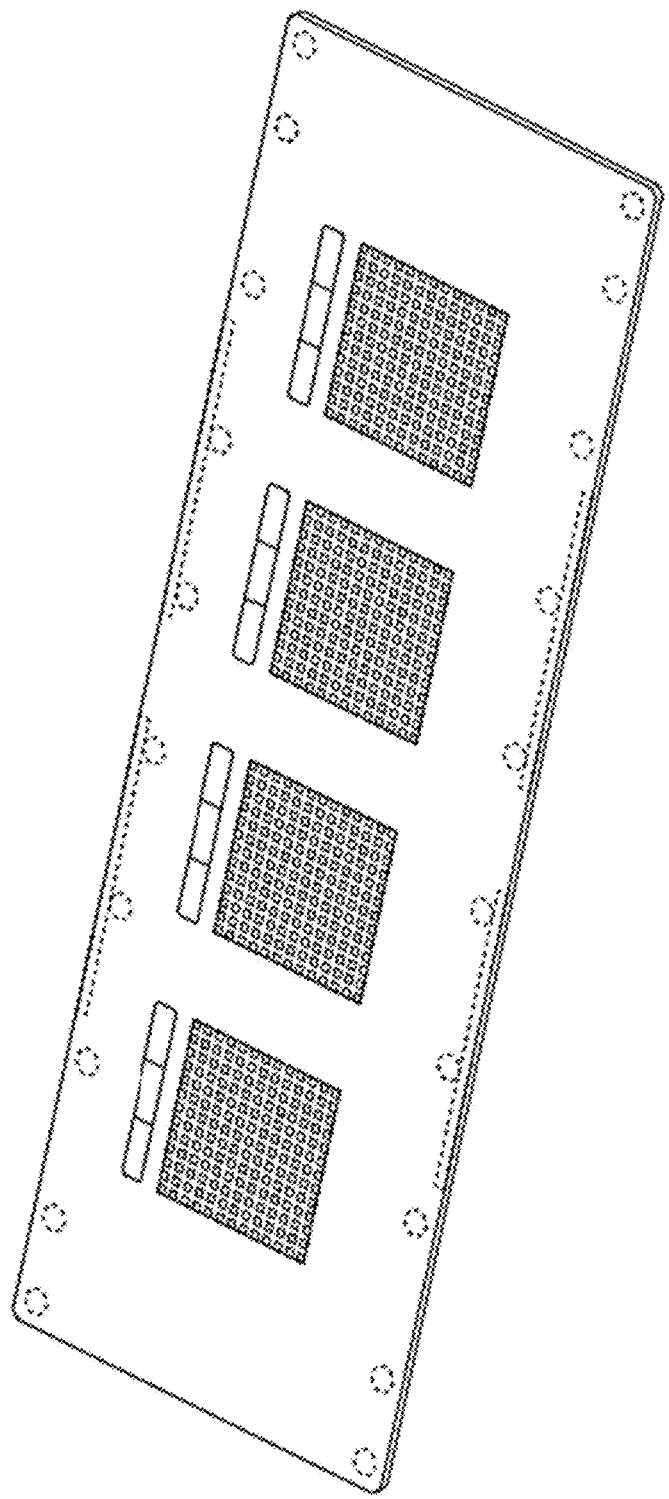
FIG. 1 is a perspective view illustrating a microfabricated device or chip in accordance with some embodiments.

The present disclosure relates generally to systems, kits, apparatus, and methods for isolation, culturing, adaptation, sampling, and/or screening of biological entities and/or nutrients. A microfabricated device (or a "chip") is disclosed for receiving a sample comprising at least one biological entity (e.g., at least one cell). The term "biological entity" may include, but is not limited to, an organism, a cell, a cell component, a cell product, and a virus, and the term "species" may be used to describe a unit of classification, including, but not limited to, an operational taxonomic unit (OTU), a genotype, a phylotype, a phenotype, an ecotype, a history, a behavior or interaction, a product, a variant, and an evolutionarily significant unit.

A cell may be Archaea, Bacteria, or Eukaryota (e.g., fungi). For example, a cell may be a microorganism, such as an aerobic, anaerobic, or facultative aerobic microorganisms. A virus may be a bacteriophage. Other cell components/products may include, but are not limited to, proteins, amino acids, enzymes, saccharides, adenosine triphosphate (ATP), lipids, nucleic acids (e.g., DNA and RNA), nucleosides, nucleotides, cell membranes/walls, flagella, fimbriae, organelles, metabolites, vitamins, hormones, neurotransmitters, and antibodies.

A nutrient may be defined (e.g., a chemically defined or synthetic medium) or undefined (e.g., a basal or complex medium). A nutrient may include or be a component of a laboratory-formulated and/or a commercially manufactured medium (e.g., a mix of two or more chemicals). A nutrient may include or be a component of a liquid nutrient medium (i.e., a nutrient broth), such as a marine broth, a lysogeny broth (e.g., Luria broth), etc. A nutrient may include or be a component of a liquid medium mixed with agar to form a solid medium and/or a commercially available manufactured agar plate, such as blood agar.

A nutrient may include or be a component of selective media. For example, selective media may be used for the growth of only certain biological entities or only biological entities with certain properties (e.g., antibiotic resistance or synthesis of a certain metabolite). A nutrient may include or be a component of differential media to distinguish one type of biological entity from another type of biological entity or other types of biological entities by using biochemical characteristics in the presence of specific indicator (e.g., neutral red, phenol red, eosin y, or methylene blue).

A nutrient may include or be a component of an extract of or media derived from a natural environment. For example, a nutrient may be derived from an environment natural to a particular type of biological entity, a different environment, or a plurality of environments. The environment may include, but is not limited to, one or more of a biological tissue (e.g., connective, muscle, nervous, epithelial, plant epidermis, vascular, ground, etc.), a biological fluid or other biological product (e.g., amniotic fluid, bile, blood, cerebrospinal fluid, cerumen, exudate, fecal matter, gastric fluid, interstitial fluid, intracellular fluid, lymphatic fluid, milk, mucus, rumen content, saliva, sebum, semen, sweat, urine, vaginal secretion, vomit, etc.), a microbial suspension, air (including, e.g., different gas contents), supercritical carbon dioxide, soil (including, e.g., minerals, organic matter, gases, liquids, organisms, etc.), sediment (e.g., agricultural, marine, etc.), living organic matter (e.g., plants, insects, other small organisms and microorganisms), dead organic matter, forage (e.g., grasses, legumes, silage, crop residue, etc.), a mineral, oil or oil products (e.g., animal, vegetable, petrochemical), water (e.g., naturally-sourced freshwater, drinking water, seawater, etc.), and/or sewage (e.g., sanitary, commercial, industrial, and/or agricultural wastewater and surface runoff).

A microfabricated device may define a high density array of microwells for cultivating the at least one biological entity. The term "high density" may refer to a capability of a system or method to distribute a number of experiments within a constant area. For example, a microfabricated device comprising a "high density" of experimental units may include about 150 microwells per $cm^2$ to about 160,000 microwells or more per $cm^2$, as discussed further herein. Additional examples are shown in TABLE 1.

TABLE 1

| Length of side of microwells (μm) | Spacing between microwells (μm) | Density of microwells (wells/cm2) |
|---|---|---|
| 500 | 500 | 100 |
| 100 | 100 | 2500 |
| 100 | 50 | 4489 |
| 100 | 10 | 8281 |
| 50 | 50 | 10000 |
| 50 | 10 | 27556 |
| 20 | 10 | 110889 |
| 10 | 5 | 444889 |
| 5 | 5 | 1000000 |

A microfabricated device may include a substrate with a series of functional layers. The series of functional layers may include a first functional layer defining a first array of experimental units (e.g., wells) and at least one subsequent functional layer defining a subsequent array of experimental units (e.g., microwells) in each experimental unit of the preceding functional layer. Each of the experimental units may be configured to receive and cultivate and/or screen biological entities and/or nutrients. In particular, systems, kits, apparatus, and methods described herein may be used for automated and/or high throughput screening of different conditions against a high density matrix of cells. For example, systems, kits, apparatus, and methods described herein may be used to test and compare the effect(s) of one or more different nutrients on the growth of microorganisms and/or screen for metabolites, enzyme activity, mutations, or other cell features.

FIG. 1 is a perspective view illustrating a microfabricated device or chip in accordance with some embodiments. Chip 100 includes a substrate shaped in a microscope slide format with injection-molded features on top surface 102. The features include four separate microwell arrays (or microarrays) 104 as well as ejector marks 106. The microwells in each microarray are arranged in a grid pattern with well-free margins around the edges of chip 100 and between microarrays 104.

Figure 2A:
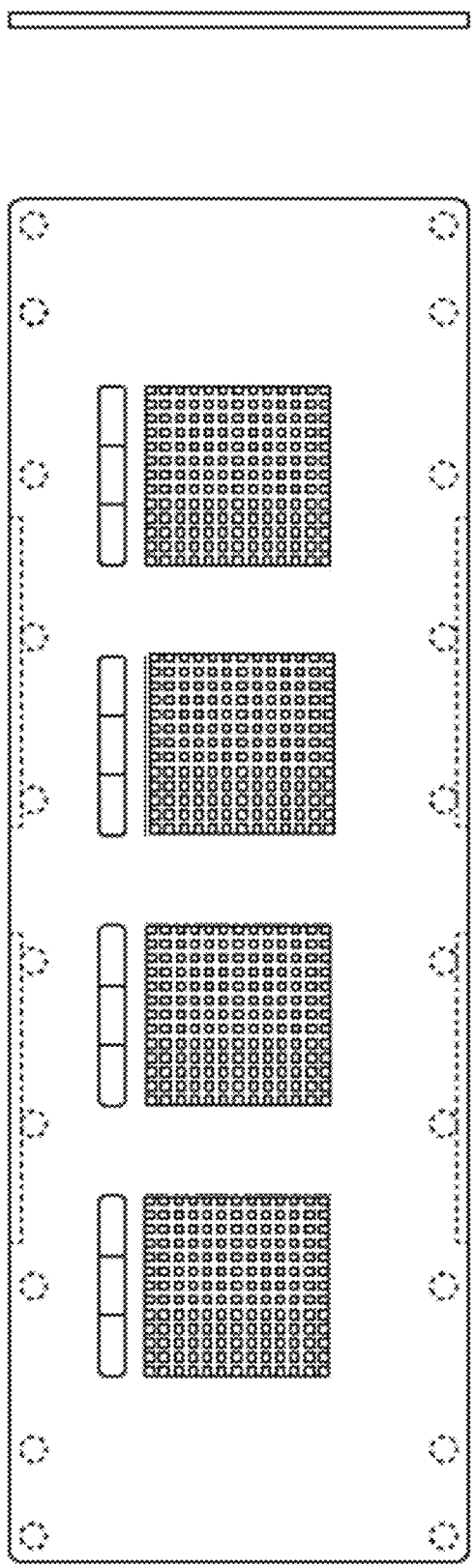
FIGS. 2A-2C are top, side, and end views, respectively, illustrating dimensions of microfabricated device or chip in accordance with some embodiments.
Figure 2B:
Figure 2C:
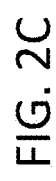

FIGS. 2A-2C are top, side, and end views, respectively, illustrating dimensions of chip 100 in accordance with some embodiments. In FIG. 2A, the top of chip 100 is approximately 25.5 mm by 75.5 mm. In FIG. 2B, the end of chip 100 is approximately 25.5 mm by 0.8 mm. In FIG. 2C, the side of chip 100 is approximately 75.5 mm by 0.8 mm.

Figure 3A:
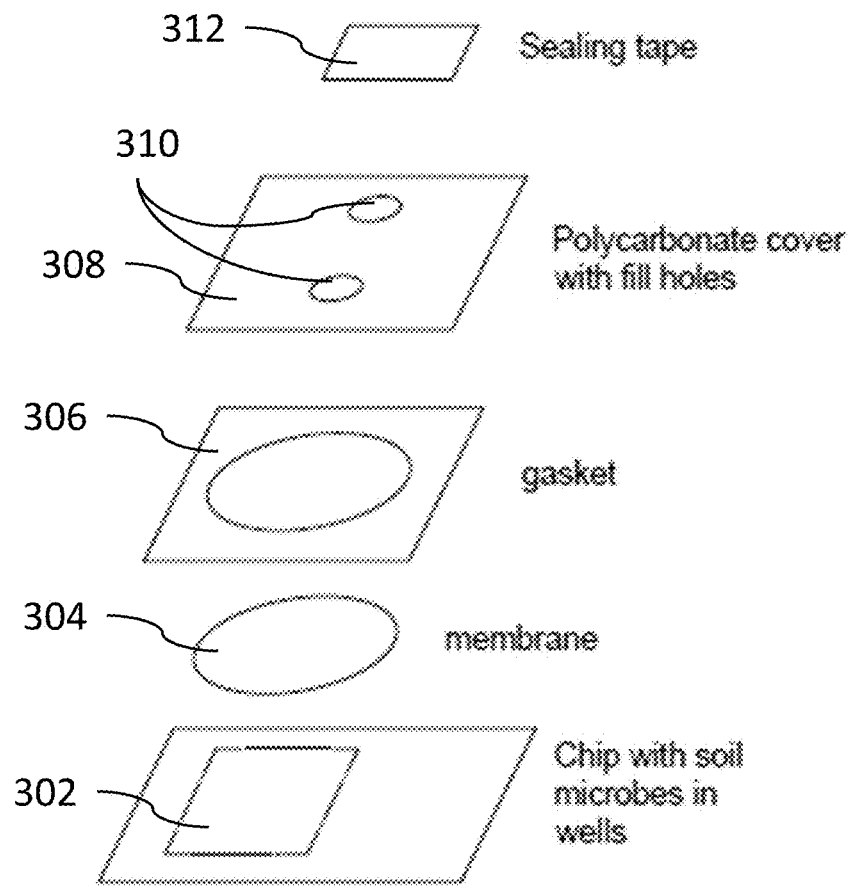
FIGS. 3A and 3B are exploded and top views, respectively, illustrating a microfabricated device or chip in accordance with some embodiments.

After a sample is loaded on a microfabricated device, a membrane may be applied to at least a portion of a microfabricated device. FIG. 3A is an exploded diagram of the microfabricated device 300 shown from a top view in FIG. 3B in accordance with some embodiments. Device 300 includes a chip with an array of wells 302 holding, for example, soil microbes. A membrane 304 is placed on top of the array of wells 302. A gasket 306 is placed on top of the membrane 304. A polycarbonate cover 308 with fill holes 310 is placed on top of the gasket 306. Finally, sealing tape 312 is applied to the cover 308.

A membrane may cover at least a portion of a microfabricated device including one or more experimental units, wells, or microwells. For example, after a sample is loaded on a microfabricated device, at least one membrane may be applied to at least one microwell of a high density array of microwells. A plurality of membranes may be applied to a plurality of portions of a microfabricated device. For example, separate membranes may be applied to separate subsections of a high density array of microwells.

A membrane may be connected, attached, partially attached, affixed, sealed, and/or partially sealed to a microfabricated device to retain at least one biological entity in the at least one microwell of the high density array of microwells. For example, a membrane may be reversibly affixed to a microfabricated device using lamination. A membrane may be punctured, peeled back, detached, partially detached, removed, and/or partially removed to access at least one biological entity in the at least one microwell of the high density array of microwells.

A portion of the population of cells in at least one experimental unit, well, or microwell may attach to a membrane (via, e.g., adsorption). If so, the population of cells in at least one experimental unit, well, or microwell may be sampled by peeling back the membrane such that the portion of the population of cells in the at least one experimental unit, well, or microwell remains attached to the membrane.

Figure 4A:
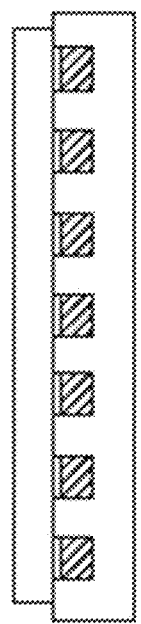
FIGS. 4A and 4B are diagrams illustrating a membrane in accordance with some embodiments.
Figure 4B:
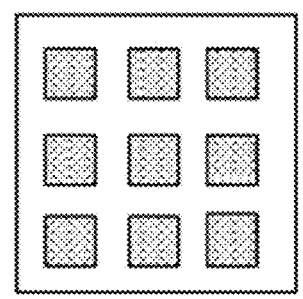
Figure 4C:
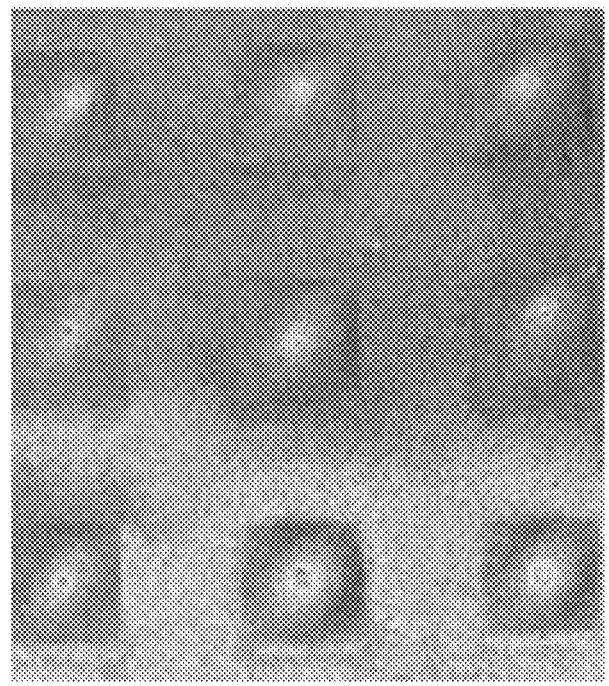
FIG. 4C is an image of a membrane surface with impressions formed from contact with an array of wells in accordance with some embodiments.

FIGS. 4A and 4B are diagrams illustrating a membrane in accordance with some embodiments. FIG. 4A shows a side view of a chip 400 defining an array of wells filled with content and a membrane 402 sealed on chip 400 over the array of wells, such that the surface of membrane 402 that was in contact with chip 400, when peeled off chip 400, has impressions of each of the wells with samples of the well contents attached (e.g., stuck) thereto, as shown in FIG. 4B. FIG. 4C is an image of a membrane surface with impressions formed from contact with an array of wells in accordance with some embodiments.

A membrane may be impermeable, semi-permeable, selectively permeable, differentially permeable, and/or partially permeable to allow diffusion of at least one nutrient into the at least one microwell of a high density array of microwells. For example, a membrane may include a natural material and/or a synthetic material. A membrane may include a hydrogel layer and/or filter paper. In some embodiments, a membrane is selected with a pore size small enough to retain at least some or all of the cells in a microwell. For mammalian cells, the pore size may be a few microns and still retain the cells. However, in some embodiments, the pore size may be less than or equal to about 0.2 µm, such as 0.1 µm. Membrane diameters and pore sizes depend on the material. For example, a hydrophilic polycarbonate membrane may be utilized, for which the diameter may range from about 10 mm to about 3000 mm, and the pore size may range from about 0.01 µm to about 30.0 µm. An impermeable membrane has a pore size approaching zero. In embodiments with an impermeable membrane, any nutrients must be provided in a microwell prior to being sealed with the membrane. A membrane that is gas permeable but not liquid permeable may allow oxygen into a microwell and carbon dioxide out of the microwell. The membrane may have a complex structure that may or may not have defined pore sizes. However, the pores may be on a nanometer scale. Other factors in selecting a membrane may include cost, ability to seal, and/or ability to sterilize.

A substrate may define an array of microchannels extended from a first surface to a second surface opposite the first surface. A microchannel may have a first opening in the first surface and a second opening in the second surface. A first membrane may be applied to at least a portion of the first surface such that at least some of the population of cells in at least one microchannel attach to the first membrane. A second detachable membrane may be applied to at least a portion of the second surface such that at least some of the population of cells in at least one microchannel attach to the second membrane. The population of cells in the at least one microchannel is sampled by peeling back the first membrane such that the at least some of the population of cells in the at least one microchannel remain attached to the first membrane and/or the second membrane such that the at least some of the population of cells in the at least one microchannel remain attached to the second membrane.

The term "high throughput" may refer to a capability of a system or method to enable quick performance of a very large number of experiments in parallel or in series. An example of a "high throughput" system may include automation equipment with cell biology techniques to prepare, incubate, and/or conduct a large number of chemical, genetic, pharmacological, optical, and/or imaging analyses to screen one or more biological entities for at least one of a metabolite, an enzyme, a protein, a nucleic acid, a phenotype, a mutation, a metabolic pathway, a gene, an adaptation, and a capability, as discussed herein. According to some embodiments, "high throughput" may refer to simultaneous or near simultaneous experiments on a scale ranging from at least about 96 experiments to at least about 10,000,000 experiments.

Systems, kits, apparatus, and methods disclosed herein may be used for high throughput screening of different conditions against a matrix of biological entities (e.g., cells). A "wells-within-wells" concept may be implemented by manufacturing (e.g., microfabricating) a substrate or chip to have multiple levels of functional layers to whatever level is required or desired (i.e., wells within wells within wells within wells, etc.). A first functional layer may define an array of experimental units (e.g., wells). Each of the experimental units presents a second functional layer by defining a subsequent array of experimental units (e.g., microwells). This enables multiple experiments or tests to be performed at the same time on a single chip, thus enabling high throughput operation.

Figure 3B:
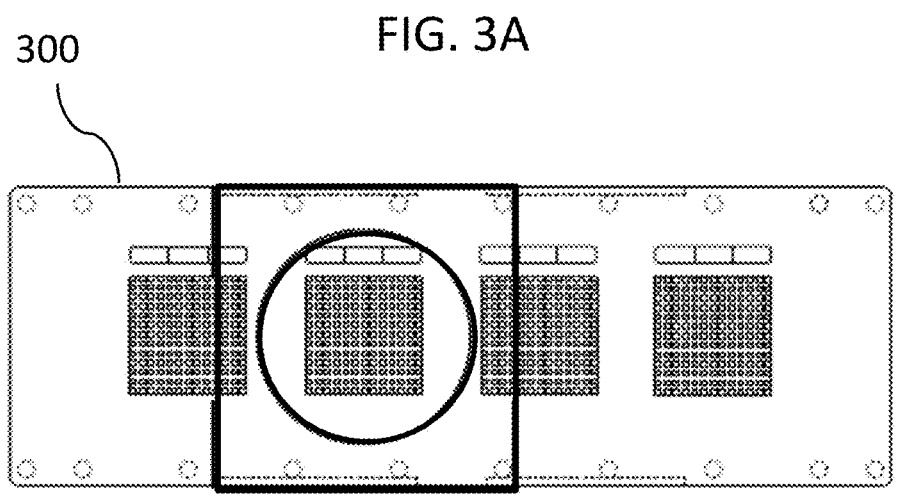

For example, in FIGS. 3A and 3B, gasket 306 is placed on top of membrane 304, which is applied to an array of wells 302 on a microfabricated device 300 in accordance with some embodiments. Gasket 306 has only one opening. However, in further embodiments, multiple smaller gaskets with a smaller opening or a single gasket with more than one smaller opening may be placed on top of a device (either with or without a membrane), thereby forming a functional layer or an array of larger experimental units with a subsequent functional layer or subsequent array of experimental units (e.g., wells 302) located therein.

With multiple levels of functional layers, more than one nutrient or nutrient formulation, for example, can be tested simultaneously or near simultaneously. The same format may be used, for example, to screen for metabolites or specific capabilities of cells or to wean microorganisms from environmentally derived nutrients to other nutrients.

Experimental units are predetermined sites on a surface of a microfabricated device. For example, a surface of a chip may be designed to immobilize cells in a first array of predetermined sites. These predetermined sites may be wells, microwells, microchannels, and/or designated immobilization sites. For example, a surface may be manufactured to define an array of microwells. The array may be divided into sections by defining walls in the substrate or adding walls. For example, the surface may be manufactured to first define a first array of wells, in which an inner surface of each well, in turn, is manufactured to define a second array of microwells, microchannels, or immobilization sites. In another example, the surface may be manufactured to define an array of microwells, and another substrate (e.g., agar, plastic, or another material) is applied to the surface to partition the surface and the microwells defined thereby. Each well, microwell, microchannel, and/or immobilization site may be configured to receive and grow at least one cell; however, in use, any given well, microwell, microchannel, or immobilization site may or may not actually receive and/or grow one or more cells. Types of experimental units may be interchangeable. For example, embodiments herein that expressly describe microwells are also intended to disclose embodiments in which the microwells are at least in part replaced with microchannels, immobilization sites, and/or other types of experimental units.

One or more portions of a microfabricated device may be selected, treated, and/or coated with a surface chemistry modifier to have a particular surface chemistry. For example, at least a portion of a substrate surface may be configured with first surface characteristics that repel cells and/or reduce cellular tendency to stick to the surface or second surface characteristics that attract cells and/or increase cellular tendency to attach to the surface. Depending on the type of target cell, the material and/or coating may be hydrophobic and/or hydrophilic. At least a portion of the top surface of the substrate may be treated to have first surface characteristics that repel target cells and/or reduce the tendency of target cells to stick to the surface. Meanwhile, at least a portion of the inner surface of each experimental unit, well, or microwell may be treated to have second surface characteristics that attract target cells and increase the tendency of target cells to occupy the experimental unit, well, or microwell. A surface of a substrate may have a plurality of portions with different surface characteristics.

A surface chemistry modifier may be applied using chemical vapor deposition, electroporation, plasma treatment, and/or electrochemical deposition. The surface chemistry modifier may control surface potential, Lund potential, zeta potential, surface morphology, hydrophobicity, and/or hydrophilicity. The surface chemistry modifier may include a silane, a polyelectrolyte, a metal, a polymer, an antibody, and/or a plasma. For example, the surface chemistry modifier may include octadecyltrichlorosilane. The surface chemistry modifier may include a dynamic copolymer, such as polyoxyethylene (20) sorbitan monolaurate and/or polyethylene glycol p-(1,1,3,3-tetramethylbutyl)-phenyl ether. The surface chemistry modifier may include a static copolymer, such as poloxamer 407, poly(L-lysine), and/or a poly(ethylene glycol)-poly(l-lysine) block copolymer.

An apparatus for screening different conditions against a matrix of cells may include a substrate with a surface defining an array of microwells. Sections of the microwell array may be partitioned into subarrays (e.g., by larger wells or walls). The substrate may be microfabricated. Each microwell may receive and grow at least one biological entity (e.g., cell). The resulting matrix of biological entities (e.g., cells) may be a high density matrix of biological entities. The first array and/or the second array may be planar, substantially planar, and/or multi-planar (e.g., on a roll).

The term "high resolution" may refer to a capability of a system or method to distinguish between a number of available experiments. For example, a "high resolution" system or method may select an experimental unit from a microfabricated device comprising a high density of experimental units, in which the experimental unit has a diameter from about 1 nm to about 800 µm. A substrate of a microfabricated device or chip may include about or more than 10,000,000 microwells. For example, an array of microwells may include at least 96 locations, at least 1,000 locations, at least 5,000 locations, at least 10,000 locations, at least 50,000 locations, at least 100,000 locations, at least 500,000 locations, at least 1,000,000 locations, at least 5,000,000 locations, or at least 10,000,000 locations.

The surface density of microwells may be from about 150 microwells per $cm^2$ to about 160,000 microwells per $cm^2$ or more. A substrate of a microfabricated device or chip may have a surface density of microwells of at least 150 microwells per $cm^2$, at least 250 microwells per $cm^2$, at least 400 microwells per $cm^2$, at least 500 microwells per $cm^2$, at least 750 microwells per $cm^2$, at least 1,000 microwells per $cm^2$, at least 2,500 microwells per $cm^2$, at least 5,000 microwells per $cm^2$, at least 7,500 microwells per $cm^2$, at least 10,000 microwells per $cm^2$, at least 50,000 microwells per $cm^2$, at least 100,000 microwells per $cm^2$, or at least 160,000 microwells per $cm^2$.

The dimensions of a microwell may range from nanoscopic (e.g., a diameter from about 1 to about 100 nanometers) to microscopic or larger. For example, each microwell may have a diameter of about 1 µm to about 800 µm, a diameter of about 25 µm to about 500 µm, or a diameter of about 30 µm to about 100 µm. A microwell may have a diameter of about or less than 1 µm, about or less than 5 µm, about or less than 10 µm, about or less than 25 µm, about or less than 50 µm, about or less than 100 µm, about or less than 200 µm, about or less than 300 µm, about or less than 400 µm, about or less than 500 µm, about or less than 600 µm, about or less than 700 µm, or about or less than 800 µm.

A microwell may have a depth of about 500 µm to about 5000 µm, a depth of about 1 µm to about 500 µm, or a depth of about 25 µm to about 100 µm. A microwell may have a depth of about 1 µm, about 5 µm, about 10 µm, about 25 µm, about 50 µm, about 100 µm, about 200 µm, about 300 µm, about 400 µm, about 500 µm, about 600 µm, about 700 µm, about 800 µm, about 1000 µm, about 1,500 µm, about 2,000 µm, about 3,000 µm, or about 5,000 µm.

Each microwell may have an opening that is round, hexagonal, or square. Each microwell may include sidewalls. The sidewalls may have a cross-sectional profile that is straight, oblique, and/or curved. At least one unique location-specific tag, as described further below, may be disposed in at least one microwell of the high density array of microwells to facilitate identification of a species and a correlation of a species to a specific microwell of the high density array of microwells. The at least one unique tag may be disposed and/or positioned at the bottom of the microwell and/or on at least one side of the microwell. The at least one unique tag may include a nucleic acid molecule with a target-specific nucleotide sequence for annealing to a target nucleic acid fragment of the at least one biological entity and a location-specific nucleotide sequence for identifying the at least one microwell of the high density array of microwells.

For example, a substrate of a microfabricated device or chip may have a surface with dimensions of about 4 inches by 4 inches. The surface may define an array of approximately 100 million microwells. The microwell array may be partitioned into about 100 subsections by walls and/or the substrate may define an array of about 100 wells, with about one million microwells defined within each subsection or well totaling to approximately 100 million microwells. For a use case of testing different nutrients, microorganisms from an environmental sample may be loaded on the chip such that individual microorganisms or clusters of microorganisms partition into the microwells on the chip, each microwell being located at the bottom of a larger well. Each larger well may include an experimental unit such that about 100 different nutrients may be tested in parallel or in series on the same chip, with each well providing up to 1 million test cases.

Target cells may be Archaea, Bacteria, or Eukaryota (e.g., fungi, plants, or animals). For example, target cells may be microorganisms, such as aerobic, anaerobic, and/or facultative aerobic microorganisms. Different nutrients may be tested in parallel or in series on a composition of target cells to analyze and compare, for instance, growth or other effects on cell population, cell components, and/or cell products. A composition of target cells may be screened for a cell component, product, and/or capability, such as one or more of a virus (e.g., a bacteriophage), a cell surface (e.g., a cell membrane or wall), a metabolite, a vitamin, a hormone, a neurotransmitter, an antibody, an amino acid, an enzyme, a protein, a saccharide, ATP, a lipid, a nucleoside, a nucleotide, a nucleic acid (e.g., DNA or RNA), a phenotype, a mutation, a metabolic pathway, a gene, and an adaptation.

A composition of cells may include an environmental sample extract and/or a dilutant. The environmental sample extract and/or the dilutant may include, but is not limited to, one or more of a biological tissue (e.g., connective, muscle, nervous, epithelial, plant epidermis, vascular, ground, etc.), a biological fluid or other biological product (e.g., amniotic fluid, bile, blood, cerebrospinal fluid, cerumen, exudate, fecal matter, gastric fluid, interstitial fluid, intracellular fluid, lymphatic fluid, milk, mucus, rumen content, saliva, sebum, semen, sweat, urine, vaginal secretion, vomit, etc.), a microbial suspension, air (including, e.g., different gas contents), supercritical carbon dioxide, soil (including, e.g., minerals, organic matter, gases, liquids, organisms, etc.), sediment (e.g., agricultural, marine, etc.), living organic matter (e.g., plants, insects, other small organisms and microorganisms), dead organic matter, forage (e.g., grasses, legumes, silage, crop residue, etc.), a mineral, oil or oil products (e.g., animal, vegetable, petrochemical), alcohol, a buffer, an organic solvent, water (e.g., naturally-sourced freshwater, drinking water, seawater, etc.), and/or sewage (e.g., sanitary, commercial, industrial, and/or agricultural wastewater and surface runoff).

A method may include, prior to applying (e.g., loading) a composition including cells to a microfabricated device, preparing the composition by combining the cells with an environmental sample extract and/or a dilutant. The method further may include liquefying the environmental sample extract and/or the dilutant. A concentration of cells in a composition may be adjusted to target distribution of one cell per experimental unit, well, or microwell.

If a sample contains cells and/or viruses, the cells in the sample may be lysed after they are applied to a microfabricated device to release nucleic acid molecules. Cells may be lysed with chemical treatment such as alkaline exposure, detergents, sonication, enzymatic proteinase K, or lysozyme exposure. Cells may also be lysed by heating.

FIG. 5A is a flowchart illustrating a method for isolating cells from a sample in accordance with some embodiments. In step 500, a sample is obtained. In step 502, the sample is homogenized and/or dispersed using at least one of a physical technique (e.g., blending and/or sonication) and a chemical technique (e.g., chelating agents, detergents, and/or enzymes). In step 504, cells in the homogenized and/or dispersed sample are separated by density centrifugation using, for example, Nycodenz® non-particulate medium (available from Progen Biotechnik GmbH, Heidelberg, Germany).

FIG. 5B is a diagram illustrating a method for isolating cells from a soil sample in accordance with some embodiments. Panel 506 shows the soil sample. Panel 508 shows the homogenized and/or dispersed sample in a test tube. Panel 510 shows the sample after centrifugation, separated into soluble debris 512, cells 514, insoluble debris 516, and Nycodenz® 518.

Figure 6:
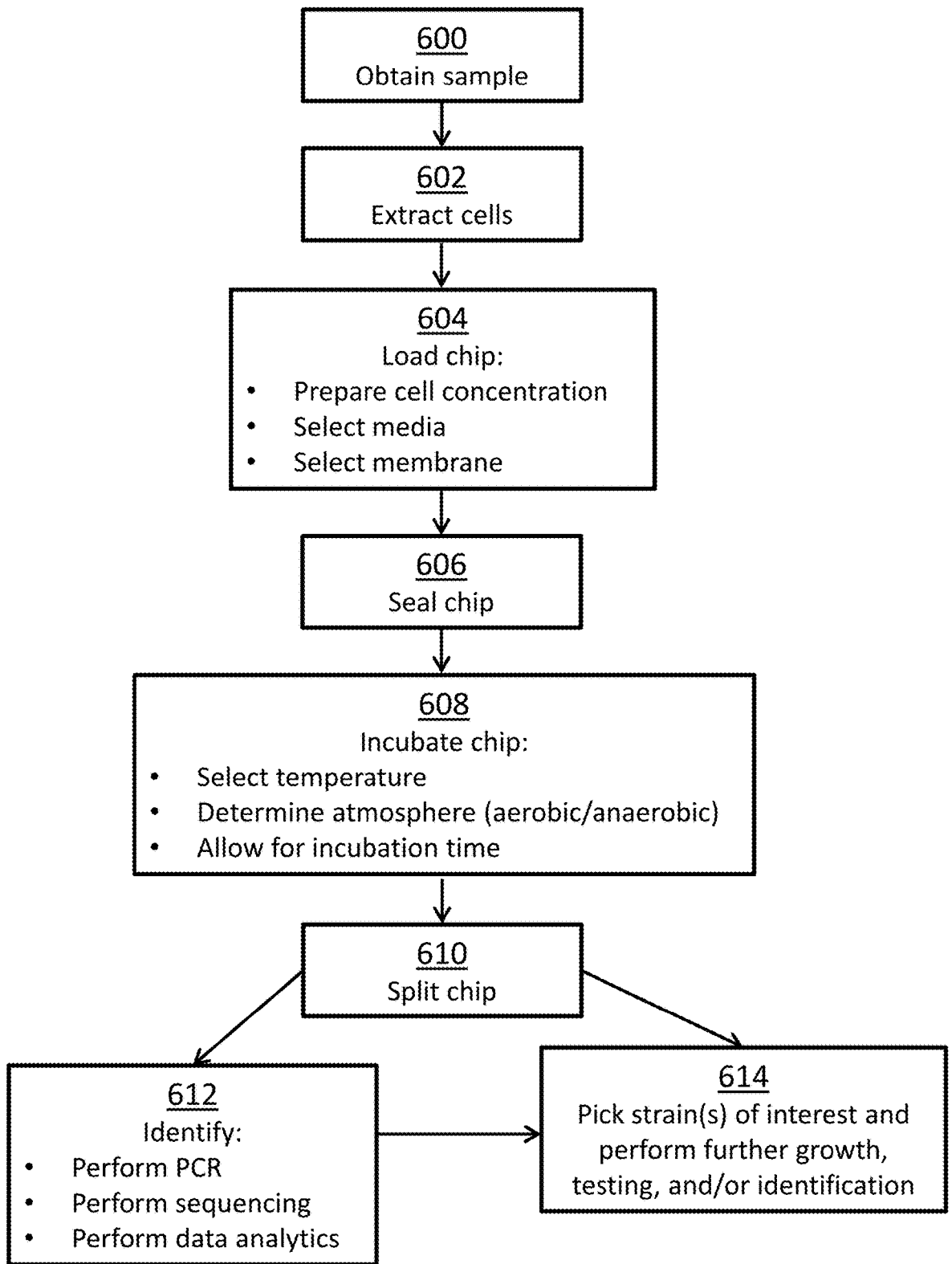
FIG. 6 is a flowchart illustrating a method for isolating and cultivating cells from a sample in accordance with some embodiments.

FIG. 6 is a flowchart illustrating a method for isolating and cultivating cells from a sample in accordance with some embodiments. In step 600, a sample is obtained. In step 602, at least one cell is extracted from the obtained sample. In step 604, at least one high density microwell array of a microfabricated device or chip is loaded with the at least one extracted cell. Step 604 may include preparing a cell concentration with the at least one extracted cell, selecting at least one nutrient/media, and/or selecting at least one membrane. In step 606, at least a portion of the microwell array is sealed with the at least one selected membrane to retain the cell concentration with the microwells. In step 608, the chip is incubated. Step 608 may include selecting a temperature, determining atmosphere (e.g., aerobic or anaerobic), and/or timing incubation). In step 610, the chip is split and/or duplicated (using, e.g., a picker), resulting in two portions of cultivated cells according to methods described herein. For example, the at least one membrane may be peeled off such that a portion of the cultivated cells remain attached or peeled off or punctured to sample the cultivated cells. In optional step 612, one portion of the cultivated cells is sacrificed for identification. Step 612 may include PCR, sequencing, and/or various data analytics. In step 614, strains of interest are identified. Further cultivation, testing, and/or identification may be performed with, for example, the strains of interest and/or the remaining portion of the cultivated cells.

Figure 7:
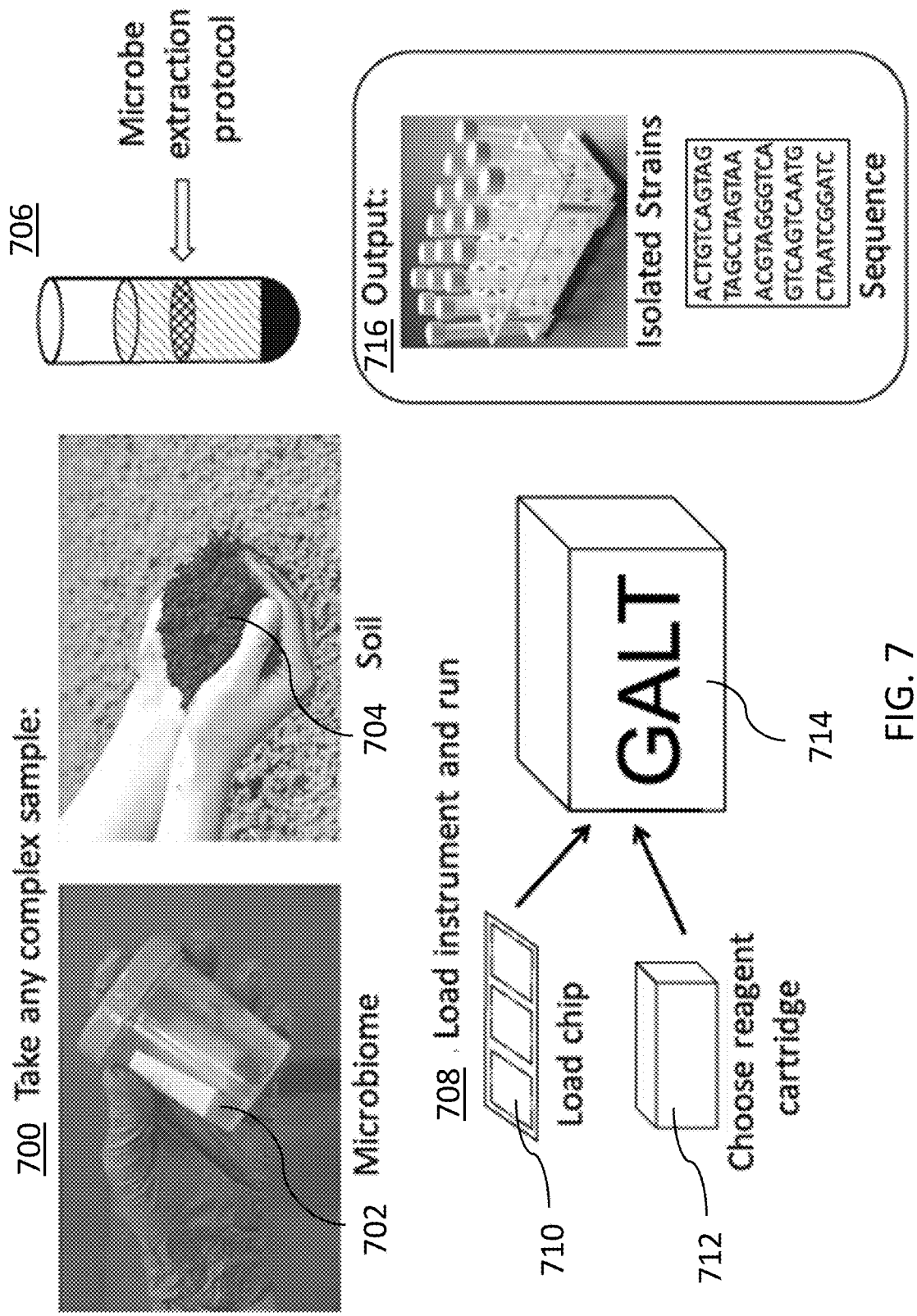
FIG. 7 is a diagram illustrating a method for isolating and cultivating cells from a complex sample in accordance with some embodiments. Panel 716 shows the output: isolated strains of cultivated cells (SEQ ID NOs: 2-6).

FIG. 7 is a diagram illustrating a method for isolating and cultivating cells from a complex sample in accordance with some embodiments. Panel 700 shows examples of complex samples, specifically a microbiome sample 702 and a soil sample 704. In Panel 706, at least one cell is extracted from the sample using, for example, the protocol illustrated in FIGS. 5A and 5B. In Panel 708, the at least one extracted cell (and any environmental extract and/or dilutant) is loaded on a microfabricated device or chip with at least one high density microwell array 710. Chip 710 and a reagent cartridge 712 may be loaded into an incubator 714. The reagent may be useful for adding liquid to maintain nutritional requirements for growth and/or various screening purposes. Panel 716 shows the output: isolated strains of cultivated cells (SEQ ID NOs: 2-6).

To identify the species or taxonomic lineage of cells or microorganisms growing in a microwell requires techniques including, but not limited to, DNA sequencing, nucleic acid hybridization, mass spectrometry, infrared spectrometry, DNA amplification, and antibody binding to identify genetic elements or other species identifiers. Many identification methods and process steps kill the microorganisms and therefore prevent further cultivation and study of microorganisms of interest. To enable both the identification of cells or microorganisms while enabling subsequent cultivation, study, and further elaboration of particular clones of interest, further embodiments are designed for sampling each experimental unit, well, or microwell across a substrate or chip while maintaining the locational integrity and separation of microorganism populations across experimental units, wells, or microwells.

A substrate as described above may enable sampling a cell population using further systems, kits, apparatus, and methods. For example, a picking device may be applied to a first surface of the substrate. The device may include at least one protrusion facing the first surface. The at least one protrusion has a diameter less than the opening diameter of each microwell, well, or experimental unit. The at least one protrusion may be inserted into at least one microwell, well, or experimental unit holding a population of cells such that a portion of the population of cells in the at least one microwell, well, or experimental unit adheres and/or attaches to the at least one protrusion. The sample of the population of cells in the at least one microwell, well, or experimental unit may be withdrawn by removing the device from the first surface of the substrate such that the portion of the population of cells in the at least one microwell, well, or experimental unit remains adhered and/or attached to the at least one protrusion. Each protrusion may be a pin or a plurality or assembly of pins.

Figure 8C:
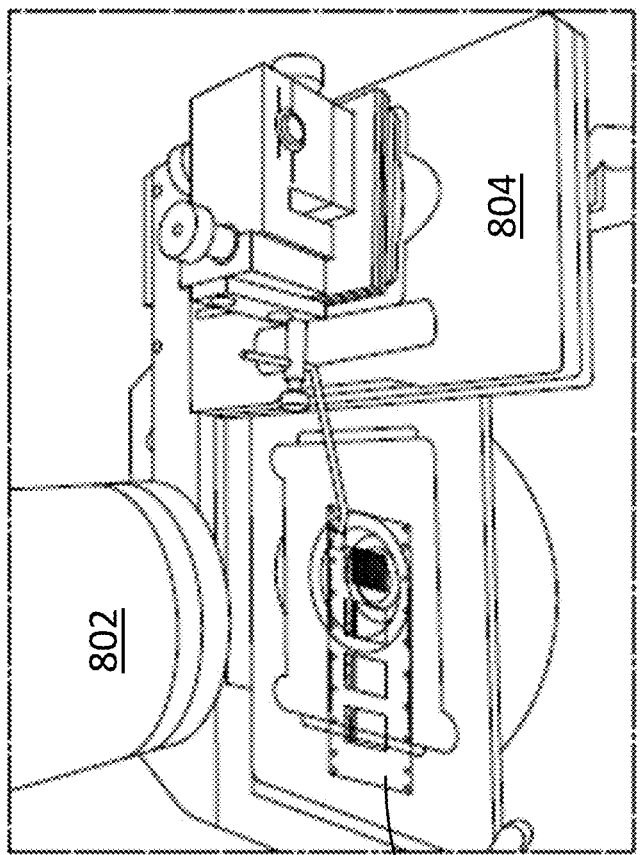
FIGS. 8A-8C are diagrams illustrating picking by one pin or multiple pins in accordance with some embodiments.
Figure 8A:
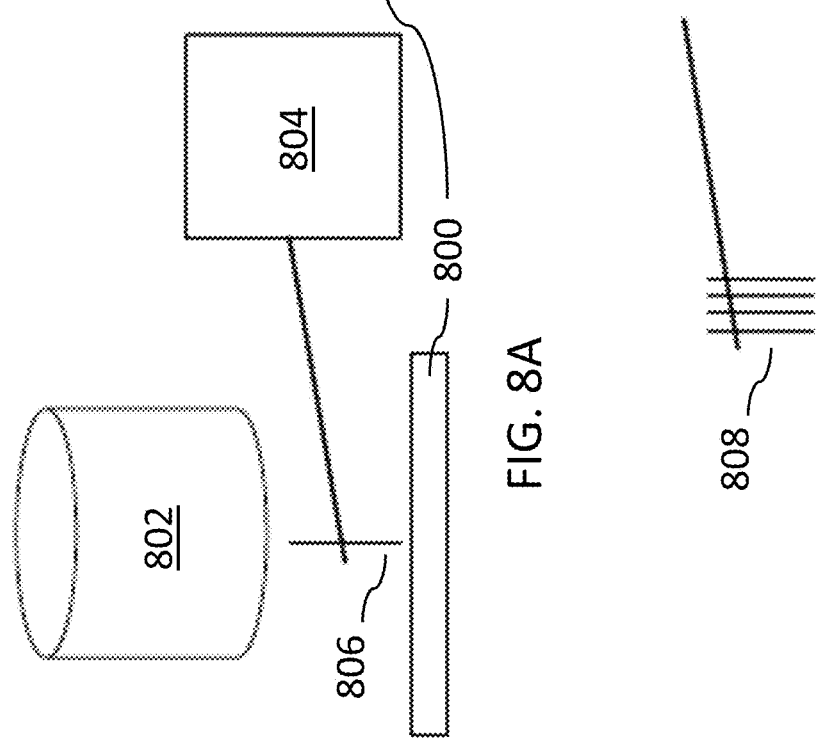
Figure 8B:

FIGS. 8A-8C are diagrams illustrating picking by one pin or multiple pins in accordance with some embodiments. Chip 800 is provided for inspection via a microscope 802 and picking via picking control device 804. In FIG. 8A, picking control device 804 comprises an arm with a single pin 806. In FIG. 8B, an arm with multiple pins 808 is shown. FIG. 8C is a perspective view of the chip during the picking process.

Figure 9B:
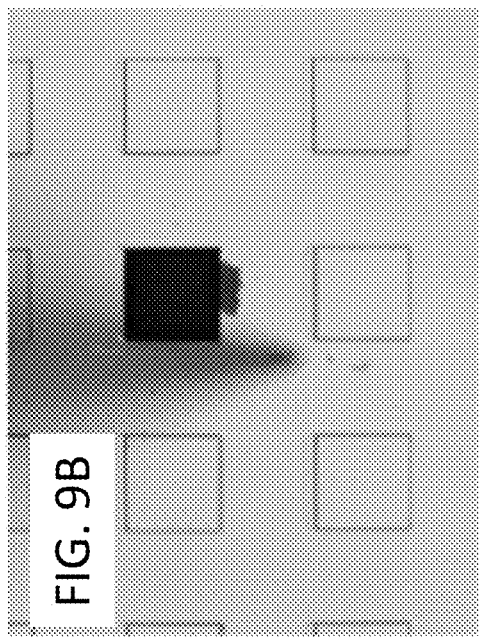
FIGS. 9A-9D are images demonstrating picking of a well in accordance with some embodiments.
Figure 9D:
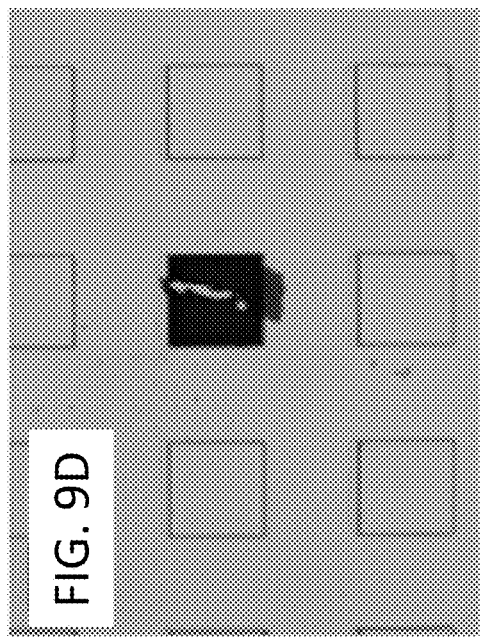
Figure 9A:
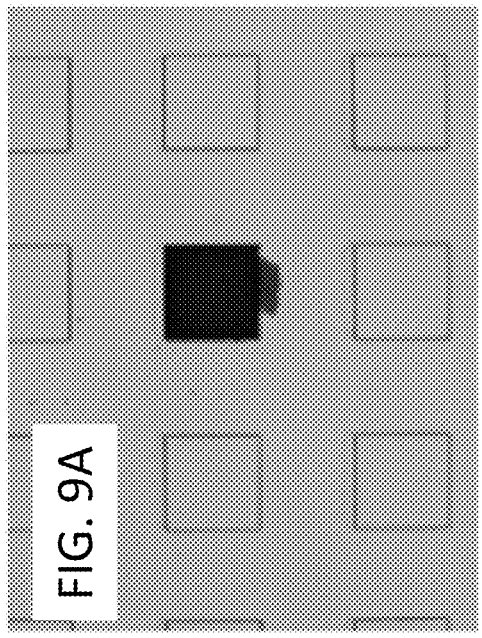
Figure 9C:
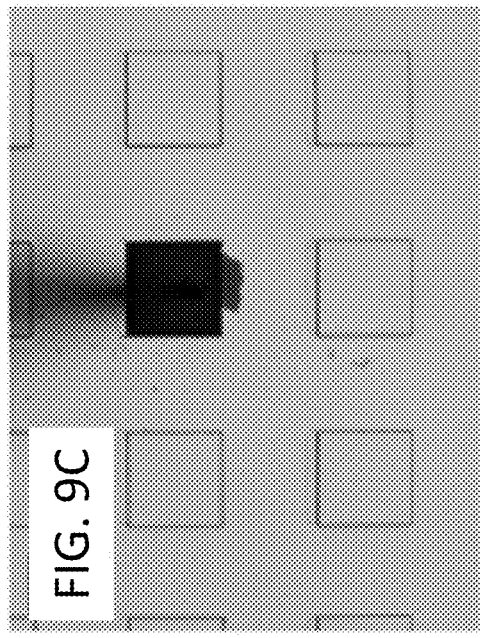

FIGS. 9A-9D are images demonstrating picking of a well in accordance with some embodiments. In FIG. 9A, the well is full. In FIG. 9B, the pin is moved into position. In FIG. 9C, the well is picked. In FIG. 9D, a sample is removed from the well.

FIGS. 10A-10D are diagrams illustrating a tool for picking a chip in accordance with some embodiments. In FIG. 10A, a tool comprising a plurality of pins is aligned with a chip having a plurality of wells. In FIG. 10B, the tool is lowered such that the pins are dipped into the wells. In FIG. 10C, the pins are shown with samples attached, and the samples are transferred to a new chip. Alternatively, in FIG. 10D, the tool is flipped such that the samples may be maintained in the tool itself.

Figure 11:
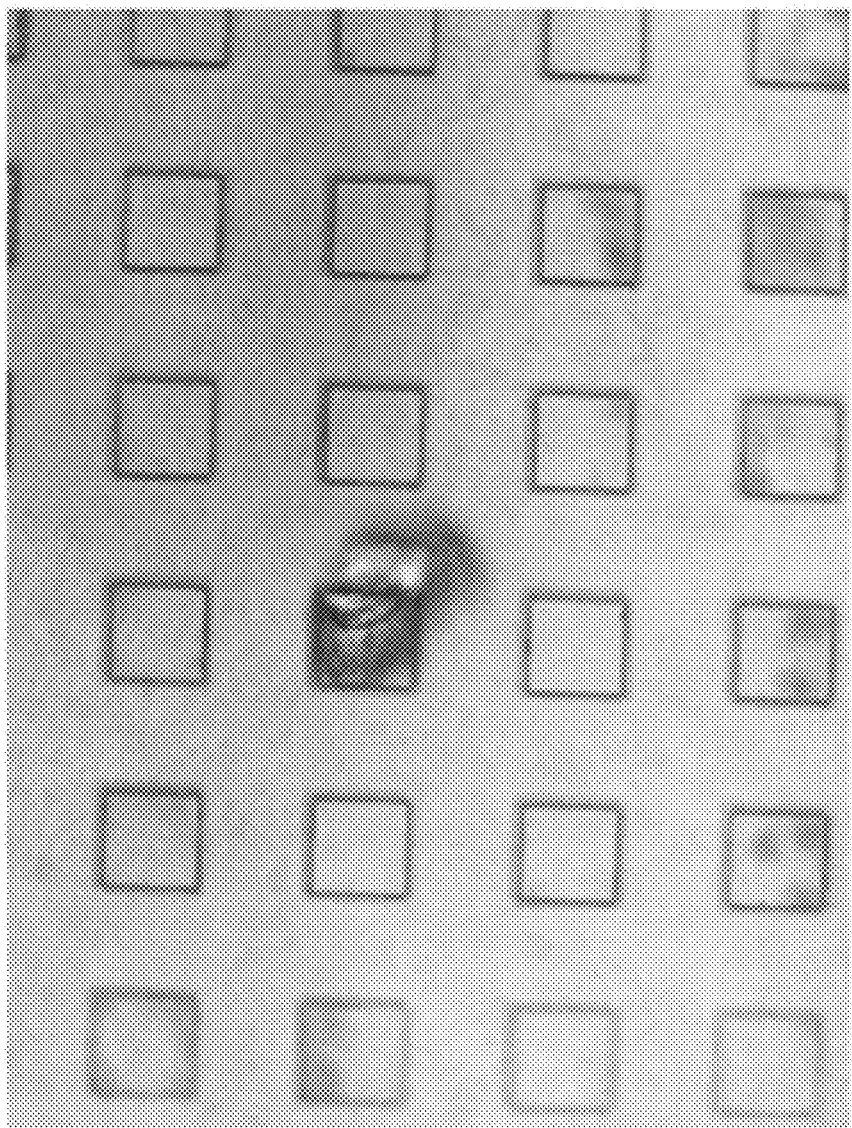
FIG. 11 is an image of a well that has been picked through a thin layer of agar, illustrating picking through a membrane or sealing layer in accordance with some embodiments.

FIG. 11 is an image of a well that has been picked through a thin layer of agar, illustrating picking through a membrane or sealing layer in accordance with some embodiments.

Alternatively, when the at least one protrusion is inserted into the at least one microwell, well, or experimental unit, a portion of the population of cells in the at least one the at least one microwell, well, or experimental unit is volume displaced up and around the at least one protrusion such that at least some of the volume displaced portion is above the first surface of the substrate and/or the inner surface of the at least one microwell, well, or experimental unit. The method also includes sampling the population of cells in the at least one microwell by collecting at least some of the volume displaced portion of the population of cells.

A similar picking device may be applied to a second surface opposite the first surface of the substrate. The device may include at least one protrusion facing the second surface. The at least one protrusion has a diameter about equal to or less than a diameter of at least one microwell, well, or experimental unit. The at least one protrusion is pushed against the second surface at a location corresponding to the at least one microwell, well, or experimental unit holding a population of cells and/or inserted into the at least one microwell, well, or experimental unit holding the population of cells such that a portion of the population of cells in the at least one microwell, well, or experimental unit is displaced above the first surface of the substrate and/or the inner surface of the at least one microwell, well, or experimental unit. The displaced portion of the population of cells may then be collected. The population of cells may be located on a plug (e.g., a hydrogel or other soft material like agar) in the at least one experimental unit, well, or microwell such that when the at least one protrusion is at least one of pushed against the second surface and inserted into the at least one microwell, the plug is displaced, thereby displacing the portion of the population of cells.

The sample of the population of cells from the at least one experimental unit, well, or microwell may be deposited in a second location. The at least one protrusion may be cleaned and/or sterilized prior to further sampling. At least a portion of the at least one protrusion may be composed of a material, treated, and/or coated with a surface chemistry modifier for surface characteristics that favor attachment of cells. The at least one protrusion may be an array of protrusions. Upon applying the device to the first surface of the substrate, the array of protrusions may be inserted into a corresponding array of experimental units, wells, or microwells. The number of protrusions in the array of protrusions may correspond to the number of experimental units in the first array, the number of microwells in one second array of microwells, or the total number of microwells in the substrate.

Another device for sampling a cell population in a substrate includes at least one needle and/or nanopipette facing the first surface. The at least one needle and/or nanopipette has an external diameter less than the opening diameter of each microwell and an internal diameter capable of accommodating a target cell diameter. The at least one needle and/or nanopipette is inserted into at least one experimental unit, well, or microwell holding a population of cells. The sample of the population of cells in the at least one experimental unit, well, or microwell is withdrawn using pressure to pull a portion of the population of cells from the at least one experimental unit, well, or microwell into the device.

The sample of the population of cells from the at least one experimental unit, well, or microwell may be deposited in a second location. The at least one needle and/or nanopipette may be cleaned and/or sterilized prior to further sampling. The at least one needle and/or nanopipette may be an array of needles and/or nanopipettes. Upon applying the device to the first surface of the microfabricated substrate, the array of needles and/or nanopipettes may be inserted into a corresponding array of experimental units, wells, or microwells. The number of needles and/or nanopipettes in the array of needles and/or nanopipettes may correspond to the number of the experimental units in the first array, the number of microwells in one second array of microwells, or the total number of microwells in the substrate.

Another method for sampling a cell population in a substrate includes applying focused acoustic energy to at least one experimental unit, well, or microwell holding a population of cells in fluid. The focused acoustic energy may be applied in a manner effective to eject a droplet from the at least one microwell, such as, for example, acoustic droplet ejection (ADE) (see, e.g., Sackmann et al., "Acoustical Micro- and Nanofluidics: Synthesis, Assembly and Other Applications," *Proceedings of the 4th European Conference on Microfluidics* (December 2014)). The droplet may include a sample of the population of cells in the at least one experimental unit, well, or microwell. The droplet may be directed into a second container or surface or substrate.

A substrate may include at least a first piece including at least a portion of the first surface and a second piece including at least a portion of the second surface. The first piece and the second piece are detachably connected along at least a portion of a plane parallel to the first surface and the second surface. The plane divides the experimental units, wells, or microwells. A cell population in at least one experimental unit, well, or microwell is sampled by detaching the first piece and the second piece such that a first portion of the population of cells in the at least one experimental unit, well, or microwell remains attached to the first piece and a second portion of the population of cells in the at least one experimental unit, well, or microwell remains attached to the second piece.

Figure 12:
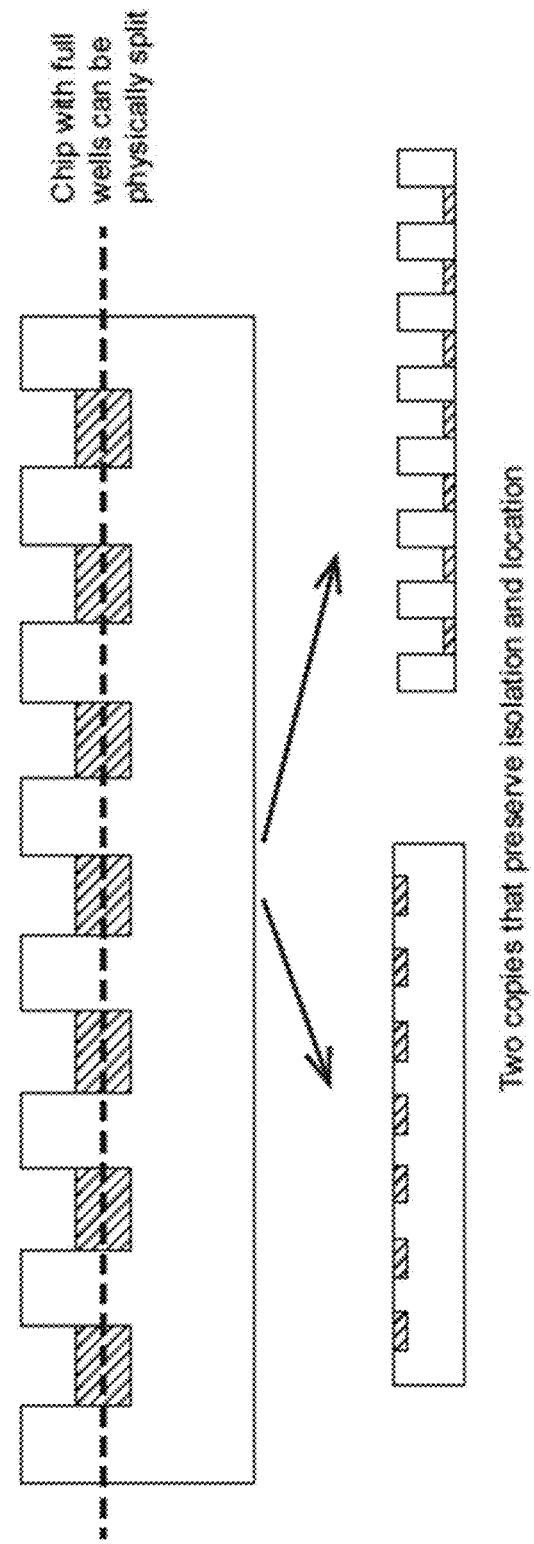
FIG. 12 is a diagram illustrating a cross-section of a chip 1200 in accordance with some embodiments.

FIG. 12 is a diagram illustrating a cross-section of a chip 1200 in accordance with some embodiments. Chip 1200 includes a substrate defining an array of wells 1202 filled with contents 1204. The substrate comprises a first piece 1206 and a second piece 1208. The first piece 1206 and the second piece 1208 are detachably connected along a plane 1210 parallel to and bisecting the array of wells 1202. When the first piece 1206 and the second piece 1208 are detached, the wells 1202 and their contents 1204 are divided, resulting in two copies of the contents 1204 that preserve both the isolation and the location of the contents 1204 on chip 1200.

Each microwell, experimental unit, or microchannel may include a partial barrier that partially separates the microwell, experimental unit, or microchannel into a first portion and a bottom portion such that a cell population is able to grow in both the first portion and the bottom portion. Prior to sampling the population of cells, the above methods may include dispersing and/or reducing clumps of cells in the population of cells. Dispersing and/or reducing clumps of cells in the population of cells may include, but is not limited to, applying sonication, shaking, and dispension with small particles.

The above methods further may include depositing the sample of the population of cells from the at least one experimental unit, well, or microwell in a second location. The second location may be a corresponding array of experimental units, wells, or microwells. The second location may be a single receptacle. The sample of the population of cells from the at least one experimental unit, well, or microwell may be maintained for subsequent cultivation. Alternatively, the remaining cells of the population of cells in the at least one experimental unit, well, or microwell may be maintained for subsequent cultivation.

The above methods further may include identifying at least one cell from the sample of the population of cells and/or the remaining cells of the population of cells. This may include performing DNA, cDNA, and/or RNA amplification, DNA and/or RNA sequencing, nucleic acid hybridization, mass spectrometry, and/or antibody binding. Alternatively, or in addition, this may include identifying an experimental unit, well, or microwell from which at least one cell originated. Each experimental unit, well, or microwell may be marked with a unique tag including a location-specific nucleotide sequence. To identify the experimental unit, well, or microwell, a location-specific nucleotide sequence may be identified in the sequencing and/or amplification reaction, and the location specific nucleotide sequence may be correlated with the at least one experimental unit, well, or microwell from which the at least one cell originated.

A microfabricated device as described above may enable culturing cells in a sample derived from an environment using further systems, kits, apparatus, and methods. For example, a sample may be applied to the first surface of a substrate such that at least one of the cells occupies at least one microwell, well, or experimental unit. A semi-permeable membrane is applied to at least a portion of the first surface (e.g., at least a portion of an inner surface of an experimental unit or well) such that a nutrient can diffuse into the at least one microwell, well, or experimental unit. Meanwhile, escape of the occupying cells from the at least one microwell, well, or experimental unit is prevented and/or mitigated. A semi-permeable membrane may be, for example, a hydrogel layer. A semi-permeable membrane may be reversibly or irreversibly connected or affixed to the substrate using, for example, lamination. Thus, the occupying cells may be incubated in the at least one microwell, well, or experimental unit with at least one nutrient. The cells may be gradually transitioned over a period of time from at least one nutrient to at least one alternative nutrient or nutrient formulation using progressive partial exchange, thereby undergoing domestication or adaptation.

A first nutrient derived from the environment may be used to incubate the cells occupying at least one first experimental unit, well, or microwell, and a second nutrient derived from the environment may be used to incubate the cells occupying at least one second experimental unit, well, or microwell. The above methods may include comparing the cells occupying the at least one first experimental unit, well, or microwell with the cells occupying at least one second experimental unit, well, or microwell to analyze the first nutrient and the second nutrient.

For example, a method may include one or more of the following steps:

Acquire a chip defining 1000 to 10 million or more microwells within a number of larger wells or flow cells, each microwell having a diameter of about 1 µm to about 800 µm and a depth of about 1 µm to about 800 µm, the chip further having one or more surface chemistries configured to facilitate the movement of target microorganisms into the microwells;

Apply an environmental sample or a derivative of the environmental sample to the chip such that any target microorganisms become located in the microwells;

Place one or more semi-permeable filters, hydrogel layers, or other barriers on the chip such that a barrier is created that allows nutrients to diffuse into the microwells but prevents and/or mitigates escape of microorganisms from the microwells;

Incubate the chip with at least one nutrient (e.g., derived from the environment);

Gradually change the nutrient source by progressive partial exchange with at least one alternative nutrient (e.g., formulation); and Detect any growth of microorganisms in the microwells.

The target cells may be Archaea, Bacteria, or Eukaryota. Target viruses may be bacteriophages. When viruses are targeted, the microwells of the chip may also include host cells in which the viruses may grow. Detecting the growth of the occupying cells or viruses may include detecting a change in biomass (e.g., DNA/RNA/protein/lipid), metabolite presence or absence, pH, consumption of nutrients, and/or consumption of gases. Detecting the growth of the occupying cells or viruses may include performing real-time sequential imaging, microscopy, optical density, fluorescence microscopy, mass spectrometry, electrochemistry, amplification (DNA, cDNA, and/or RNA), sequencing (DNA and/or RNA), nucleic acid hybridization, and/or antibody binding.

Figure 13:
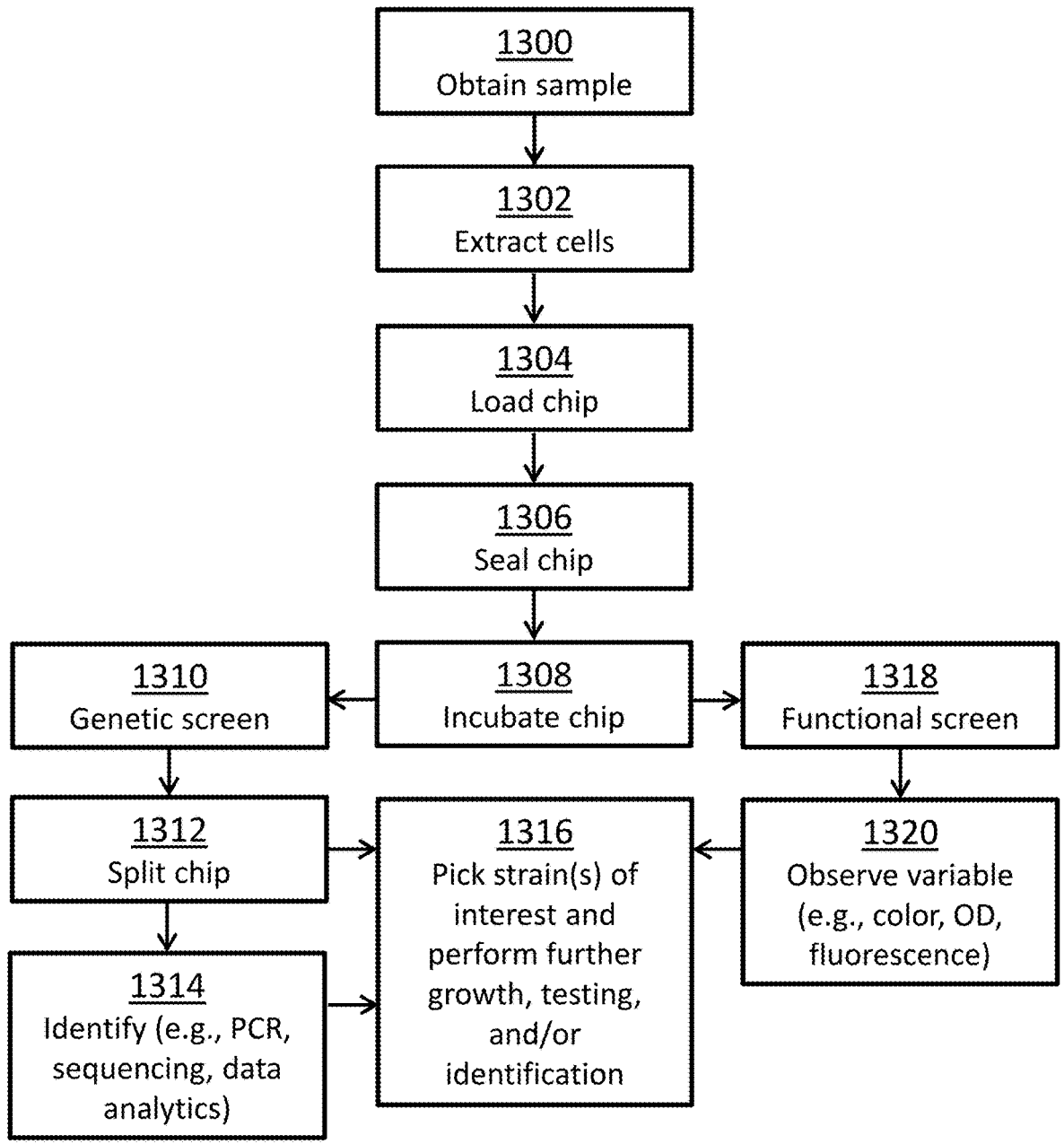
FIG. 13 is a flowchart illustrating methods for screening in accordance with some embodiments.

FIG. 13 is a flowchart illustrating methods for screening in accordance with some embodiments. In step 1300, a sample is obtained. In step 1302, at least one cell is extracted from the obtained sample. In step 1304, at least one high density microwell array of a microfabricated device or chip is loaded with the at least one extracted cell. Step 1304 may include preparing a cell concentration with the at least one extracted cell, selecting at least one nutrient/media, and/or selecting at least one membrane. In step 1306, at least a portion of the microwell array is sealed with the at least one selected membrane to retain the cell concentration with the microwells. In step 1308, the chip is incubated. Step 1308 may include selecting a temperature, determining atmosphere (e.g., aerobic or anaerobic), and/or timing incubation). A genetic screen and/or a functional screen may be performed. In step 1310, a genetic screen is applied to the chip. In step 1312, the chip is split and/or duplicated (using, e.g., a picker), resulting in two portions of cultivated cells according to methods described herein. For example, the at least one membrane may be peeled off such that a portion of the cultivated cells remain attached or peeled off or punctured to sample the cultivated cells. In optional step 1314, one portion of the cultivated cells is sacrificed for identification. Step 1314 may include PCR, sequencing, and/or various data analytics. In step 1316, strains of interest are identified. Further cultivation, testing, and/or identification may be performed with, for example, the strains of interest and/or the remaining portion of the cultivated cells. Alternatively, in step 1318, a functional screen is applied to the chip. In step 1320, one or more variables are observed and, as in step 1316, strains of interest are identified.

Figure 14:
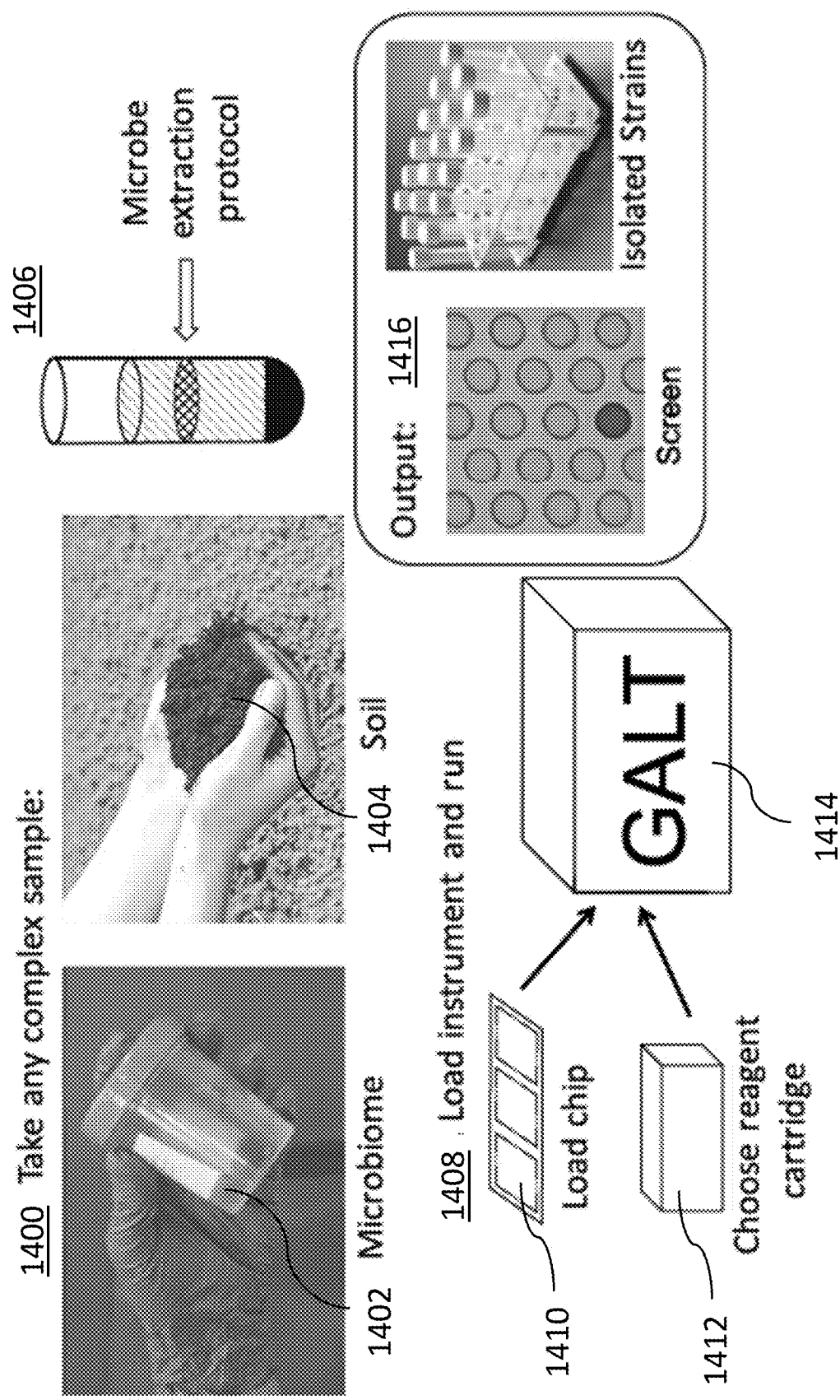
FIG. 14 is a diagram illustrating a screening method in accordance with some embodiments.

FIG. 14 is a diagram illustrating a screening method in accordance with some embodiments. Panel 1400 shows examples of complex samples, specifically a microbiome sample 1402 and a soil sample 1404. In Panel 1406, at least one cell is extracted from the sample using, for example, the protocol illustrated in FIGS. 5A and 5B. In Panel 1408, the at least one extracted cell (and any environmental extract and/or dilutant) is loaded on a microfabricated device or chip with at least one high density microwell array 1410. Chip 1410 and a reagent cartridge 1412 may be loaded into an incubator 1414. The reagent may be useful for adding liquid to maintain nutritional requirements for growth and/or various screening purposes. Panel 1416 shows the output: screen results and isolated strains of cultivated cells.

Figure 15:
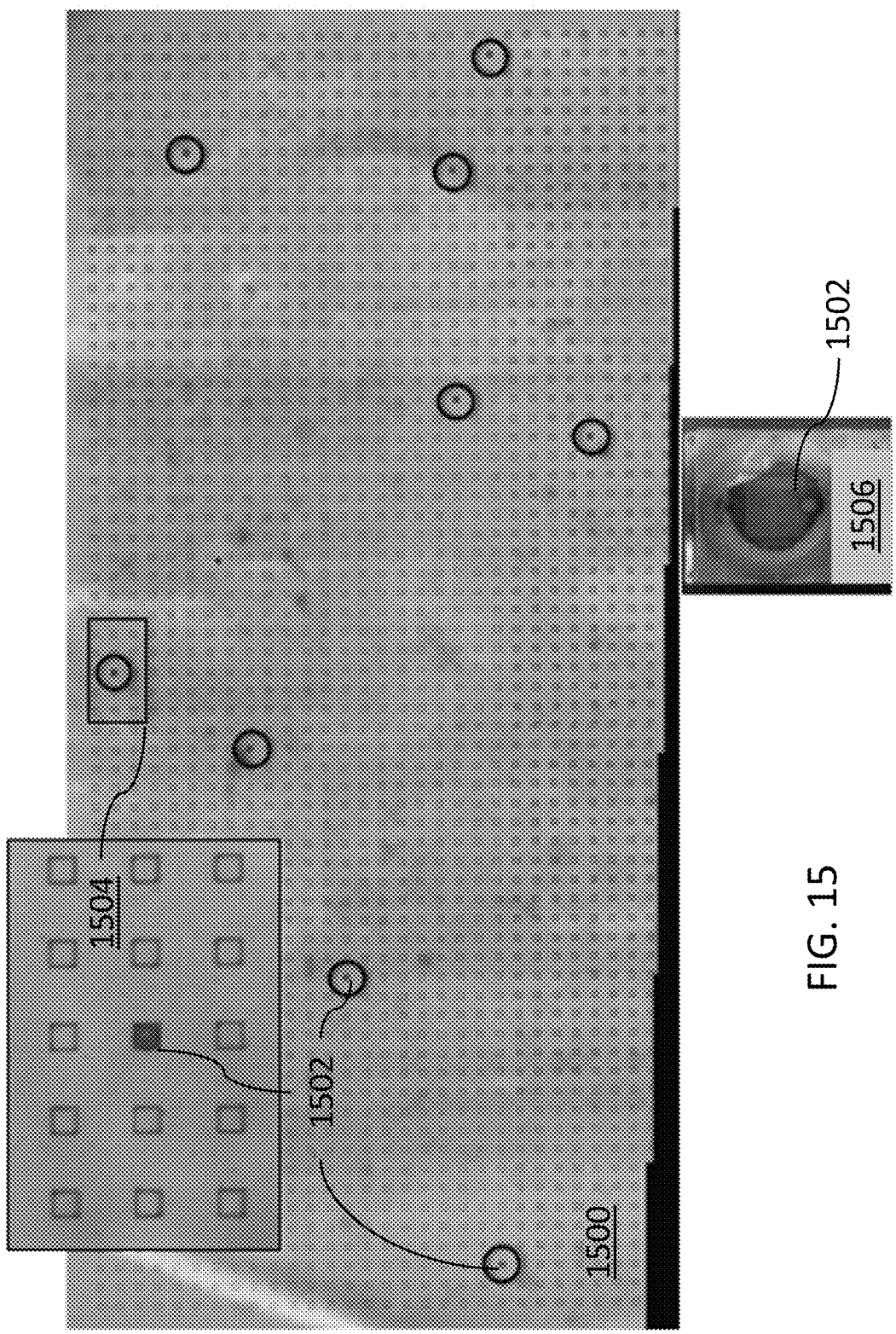
FIG. 15 is a series of images illustrating a screening example in accordance with some embodiments.

FIG. 15 is a series of images illustrating a screening example in accordance with some embodiments. The images show portions of a chip with a membrane and an acid-sensitive layer applied thereon to screen for low pH. In image 1500, more than 1800, 50-µm microwells are visible with nine clear hits 1502. Image 1504 is a magnified view of box 1504, and image 1506 is a magnified view of one of the microwells with a hit 1502.

Figure 16A:
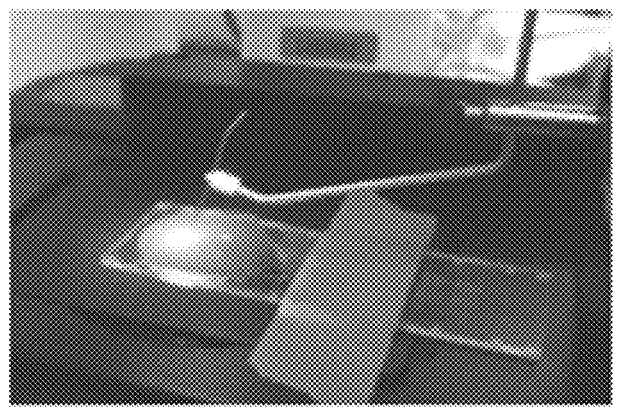
FIGS. 16A-16C are images illustrating recovery from a screen in accordance with some embodiments.
Figure 16B:
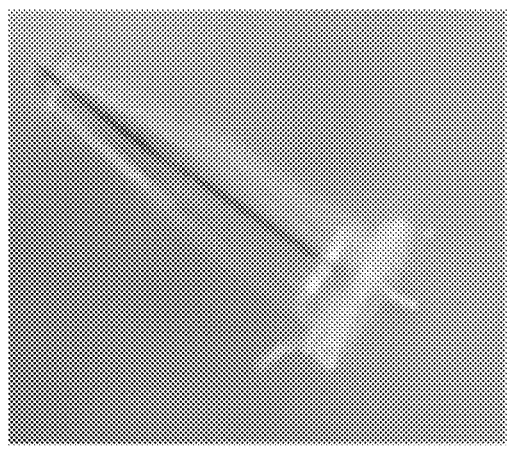
Figure 16C:
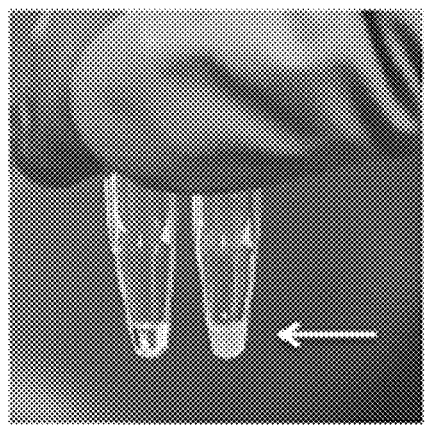

FIGS. 16A-16C are images illustrating recovery from a screen in accordance with some embodiments. In FIG. 16A, at least one well is picked using a microscope and a picking device with at least one pin. In FIG. 16B, a pin is removed and incubated in media. In FIG. 16C, growth is visible.

Figure 17B:
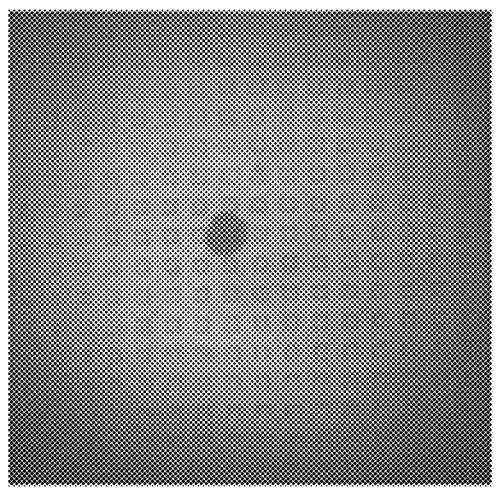
FIG. 17B is a fluorescence image of a chip following screening in accordance with some embodiments.
Figure 17C:
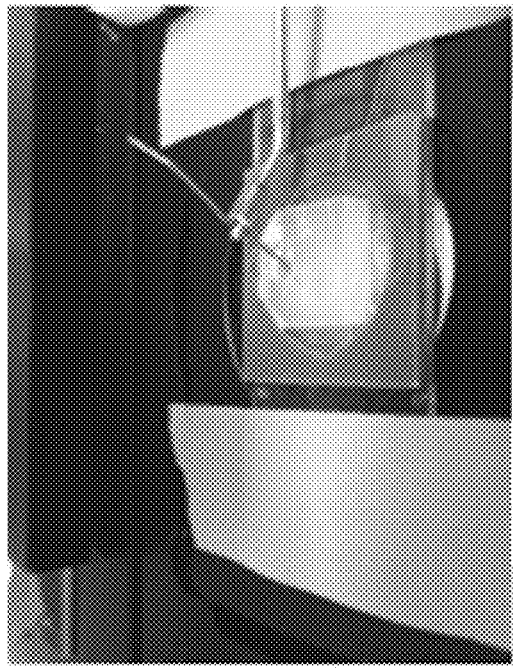
FIG. 17C is an image showing a process of picking a sample from the chip following screening in accordance with some embodiments.
Figure 17A:
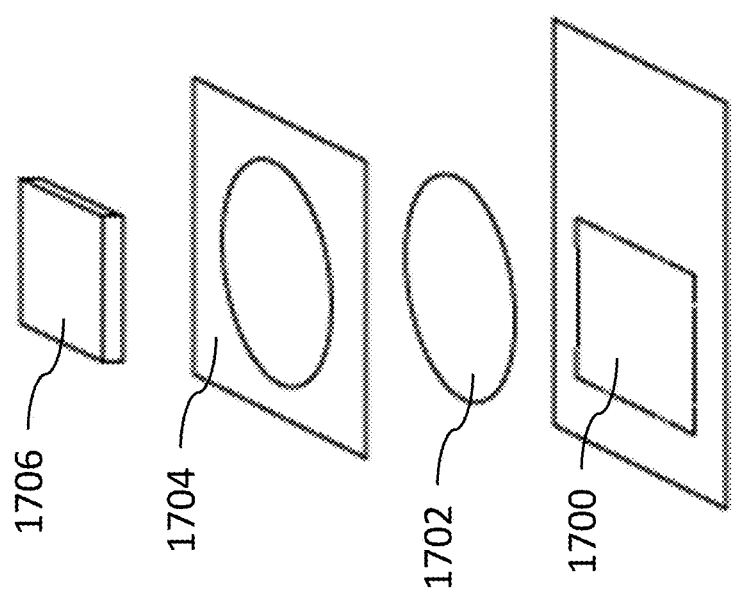
FIG. 17A is an exploded diagram illustrating a chip for screening in accordance with some embodiments.

FIG. 17A is an exploded diagram illustrating a chip for screening in accordance with some embodiments. In FIG. 17A, chip 1700 includes a high density array of microwells with, for example, soil microbes in the microwells. Membrane 1702 is applied to chip 1700. Gasket 1704 is applied to chip 1700 over membrane 1702. Agar with fluorescent *E. coli* bacteria 1706 is applied to chip 1700 over gasket 1704 and membrane 1702. FIGS. 17B and 17C are images illustrating a screening example in accordance with some embodiments. In this example, the screen is for clearance zones. FIG. 17B is a fluorescence image of a chip, prepared like chip 1700 in FIG. 17A, following the screen. FIG. 17C is an image showing a process of picking a sample from this chip through the agar.

In some embodiments, a location on an apparatus may be correlated with a portion of a sample present at that location, after that portion of the sample (or a part of the portion) is removed from the apparatus. The apparatus may be or include a microarray. The microarray may comprise a plurality of locations for applying a sample, wherein each location is marked with a unique tag which may be used to identify the location from which a portion of the sample came, after that portion of the sample is removed from the microarray.

The disclosure relates to a method of identifying from which location on a microarray a portion of a sample comprising at least one nucleic acid molecule came, after that portion of the sample is removed from the microarray, the method comprising the steps of: (a) applying one or more portions of the sample onto one or more of a plurality of locations on the microarray, wherein each location is marked with a unique tag comprising a nucleic acid molecule comprising: (i) a location-specific nucleotide sequence; and (ii) a first target-specific nucleotide sequence; (b) allowing the target nucleic acid molecule found in at least one portion of the sample to anneal to a tag marking a location; (c) performing primer extension, reverse transcription, single-stranded ligation, or double-stranded ligation on the population of annealed nucleic acid molecules, thereby incorporating a location-specific nucleotide sequence into each nucleic acid molecule produced by primer extension, reverse transcription, single-stranded ligation, or double-stranded ligation; (d) combining the population of nucleic acid molecules produced in step (c); (e) sequencing the population of combined nucleic acid molecules, thereby obtaining the sequence of one or more location-specific nucleotide sequences; and (f) correlating the sequence of at least one location-specific nucleotide sequence obtained from the population of combined nucleic acid molecules to the location on the microarray marked with a tag comprising said location-specific nucleotide sequence; thereby identifying from which location on a microarray a portion of a sample comprising at least one nucleic acid molecule came. In some embodiments, a sample may include at least one cell and one or more nucleic acid molecules are released from the cell after step (a) and before step (b). A sample may include at least one cell, and the at least one cell replicates or divides after step (a) and before step (b). A portion of the portion of the sample may be removed from at least one location before step (b) and said portion of the portion of the sample may be stored in a separate receptacle correlated to the original location of the portion of the sample on the microarray. The method of correlating or identifying a location may further comprise the step of amplifying the nucleic acid molecules produced in step (c) or the population of combined nucleic acid molecules produced in step (d). The amplifying step may comprise polymerase chain reaction amplification, multiplexed polymerase chain reaction amplification, nested polymerase chain reaction amplification, ligase chain reaction amplification, ligase detection reaction amplification, strand displacement amplification, transcription based amplification, nucleic acid sequence-based amplification, rolling circle amplification, or hyper-branched rolling circle amplification. Additional primers may be added during an amplification reaction. For example, both 5' and 3' primers may be needed for a PCR reaction. One of the primers used during an amplification reaction may be complementary to a nucleotide sequence in the sample.

In some embodiments, a composition including cells and/or viruses may be treated with a nuclease before the composition is applied to a microfabricated device so that contaminating nucleic acid molecules are not amplified in subsequent steps.

The sequencing used in the disclosed methods and apparatuses may be any process of obtaining sequence information, including hybridization and use of sequence specific proteins (for example, enzymes). Sequencing may comprise Sanger sequencing, sequencing by hybridization, sequencing by ligation, quantitative incremental fluorescent nucleotide addition sequencing (QIFNAS), stepwise ligation and cleavage, fluorescence resonance energy transfer, molecular beacons, TaqMan reporter probe digestion, pyrosequencing, fluorescent in situ sequencing (FISSEQ), wobble sequencing, multiplex sequencing, polymerized colony (POLONY) sequencing (see, e.g., U.S. Patent Application Publication No. 2012/0270740, which is incorporated by reference herein in its entirety); nanogrid rolling circle (ROLONY) sequencing (see, e.g., U.S. Patent Application Publication No. 2009/0018024, which is incorporated by reference herein in its entirety), allele-specific oligo ligation assay sequencing, or sequencing on a next-generation sequencing (NGS) platform. Non-limiting examples of NGS platforms include systems from Illumina® (San Diego, Calif.) (e.g., MiSeq™, NextSeq™, HiSeq™, and HiSeq X™), Life Technologies (Carlsbad, Calif.) (e.g., Ion Torrent™), and Pacific Biosciences (Menlo Park, Calif.) (e.g., PacBio® RS II).

An organism or species may be identified by comparing the nucleic acid sequence obtained from that organism to various databases containing sequences of organisms. For example, ribosomal RNA sequence data is available in the SILVA rRNA database project (Max Planck Institute for Marine Microbiology, Bremen, Germany (www.arb-silva.de); see, e.g., Quast et al., "The SILVA Ribosomal RNA Gene Database Project: Improved Data Processing and Web-Based Tools," 41 *Nucl. Acids Res.* D590-D596 (2013), and Pruesse et al., "SINA: Accurate High-Throughput Multiple Sequence Alignment of Ribosomal RNA Genes," 28 *Bioinformatics* 1823-1829 (2012), both of which are incorporated by reference herein in their entirety). Other ribosomal RNA sequence databases include the Ribosomal Database Project (Michigan State University, East Lansing, Mich. (www.rdp.cme.msu.edu); see, e.g., Cole et al., "Ribosomal Database Project: Data and Tools for High Throughput rRNA Analysis" 42 *Nucl. Acids Res. D*633-D642 (2014), which is incorporated by reference herein in its entirety) and Greengenes (Lawrence Berkeley National Laboratory, Berkeley, Calif. (www.greengenes.lbl.gov); see, e.g., DeSantis et al., "Greengenes, a Chimera-Checked 16S rRNA Gene Database and Workbench Compatible with ARB," 72 *Appl. Environ. Microbiol.* 5069-72 (2006), which is incorporated by reference herein in its entirety). The GenBank® genetic sequence database contains publicly available nucleotide sequences for almost 260,000 formally described species (National Institutes of Health, Bethesda, Md. (www.ncbi.nlm.nih.gov); see, e.g., Benson et al., "GenBank," 41 *Nucl. Acids Res. D*36-42 (2013).

The sequence used for matching and identification may include the 16S ribosomal region, 18S ribosomal region or any other region that provides identification information. The desired variant may be a genotype (e.g., single nucleotide polymorphism (SNP) or other type of variant) or a species containing a specific gene sequence (e.g., a sequence coding for an enzyme or protein). An organism or species may also be identified by matching its sequence to a custom internal sequence database. In some cases, one may conclude that a certain species or organism is found at a location on the microarray if the sequence obtained from the portion of the sample at the location has at least a specified percentage identity (e.g., at least 90%, at least 91%, at least 92%, at least 93%, at least 94%, at least 95%, at least 96%, at least 97%, at least 98%, at least 99%, or 100% identity) to the known DNA, cDNA, or RNA sequence obtained from that species or microorganism.

The disclosure further relates to a method of manufacturing a microarray comprising a plurality of locations for applying a sample, wherein at least one location is marked with a unique tag, the method comprising the steps of: (a) synthesizing a plurality of tags, wherein each tag comprises a nucleic acid molecule comprising: (i) a location-specific nucleotide sequence; and (ii) a target-specific nucleotide sequence; and (b) placing a tag on at least one location of the plurality of locations on the microarray. In an alternative embodiment, the disclosure relates to a method of manufacturing a microarray comprising a plurality of locations for applying a sample, wherein at least one location is marked with a unique tag, the method comprising the steps of: (a) synthesizing a plurality of tags, wherein each tag comprises a nucleic acid molecule comprising: a target-specific nucleotide sequence and not comprising a location-specific nucleotide sequence; and (b) placing a tag on at least one location of the plurality of locations on the microarray. The target-specific sequence may be the same at every location in the microarray. In either of the above embodiments, step (a) may be performed before step (b). The placing step (b) may comprise placing the tag at each location by a liquid handling procedure (for example, pipetting, spotting with a solid pin, spotting with a hollow pin, or depositing with an inkjet device). At least one tag may include a nucleic acid molecule or a portion of a nucleic acid molecule that is pre-synthesized. Step (a) may be performed simultaneously with step (b). In certain embodiments, at least one tag comprises a nucleic acid molecule that is synthesized at each location by in situ synthesis. The synthesizing step (a) may comprise inkjet printing synthesis or photolithography synthesis.

Each location on a microarray may be configured to receive a portion of the sample. A location may be tagged or labeled with a nucleic acid molecule (e.g., an oligonucleotide) that comprises at least one of: (i) a location-specific nucleotide sequence (e.g., a barcode); and (ii) a target-specific nucleotide sequence. A target-specific nucleotide sequence may complement or substantially complement a nucleotide sequence found in the sample. The order of the nucleotide sequences from the 5' end to the 3' end in the nucleic acid molecule may be: (1) a location-specific nucleotide sequence; and (2) a target-specific nucleotide sequence. Alternatively, the order of the nucleotide sequences from the 5' end to the 3' end in the nucleic acid molecule may be (2) then (1). The nucleic acid molecule may be attached at its 5' end to the microarray. One or more locations on the apparatus (e.g., microarray) may be untagged or unlabeled.

The terms "complementary" or "substantially complementary" may refer to the hybridization, the base pairing, or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T/U, or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, at least about 75%, or at least about 90% complementary.

The term "selectively hybridize" or "selective hybridization" may refer to binding detectably and specifically. Polynucleotides, oligonucleotides and fragments thereof selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS.

The nucleic acid molecule that is part of a location tag may comprise at least one deoxyribonucleotide or at least one ribonucleotide. The nucleic acid molecule may be single-stranded or double-stranded. A nucleic acid molecule may be a double-stranded molecule having a single-stranded overhang.

In some embodiments, the location tag may be used to amplify a nucleic acid molecule that anneals to it. Thus, the location tag may comprise a nucleic acid sequence that further comprises an amplification primer binding site. An amplification primer binding site may be at least 16, at least 17, at least 18, at least 19, at least 20, at least 21, at least 22, at least 23, at least 24, at least 25, at least 26, at least 27, at least 28, at least 29, or at least 30 nucleotides in length. The order of the nucleotide sequences from the 5' end to the 3' end in the nucleic acid molecule may be, for example: (1) the amplification primer binding site; (2) the location-specific nucleotide sequence; and (3) the target-specific nucleotide sequence.

In some embodiments, a nucleic acid molecule may comprise a target-specific nucleotide sequence without comprising a location-specific nucleotide sequence. In certain embodiments, a nucleic acid molecule may comprise a target-specific nucleotide sequence without comprising either a location-specific nucleotide sequence or an amplification binding site sequence. In further embodiments, a nucleic acid molecule may comprise only a target-specific nucleotide sequence. In even further embodiments, a nucleic acid molecule may contain only a target-specific nucleotide sequence. The amplification primer binding site may be capable of binding to a polymerase chain reaction primer, a multiplexed polymerase chain reaction primer, a nested polymerase chain reaction primer, a ligase chain reaction primer, a ligase detection reaction primer, a strand displacement primer, a transcription based primer, a nucleic acid sequence-based primer, a rolling circle primer, or a hyperbranched rolling circle primer. Additional primers may be added to the microarray during an amplification reaction. For example, both 5' and 3' primers may be needed for a PCR reaction. Target-specific nucleotide sequences may be amplified in the locations containing target nucleic acid molecules and may be detected by, for example, qPCR, end point PCR, and/or dyes to detect amplified nucleic acid molecules.

It may be desirable to sequence a nucleic acid molecule that anneals to a location tag or the amplified product based on such a nucleic acid molecule. The location tag may comprise a nucleic acid sequence that further comprises an adapter nucleotide sequence. In certain embodiments, an adapter nucleotide sequence may not be found in the location tag but is added to the sample nucleic acid molecules in a secondary PCR reaction or by ligation. An adapter nucleotide sequence may be a generic adapter or an adapter for a specific sequencing platform (e.g., Illumina® or Ion Torrent™). An adapter nucleotide sequence may include a sequencing primer binding site. A sequencing primer binding site may be capable of binding a primer for Sanger sequencing, sequencing by hybridization, sequencing by ligation, quantitative incremental fluorescent nucleotide addition sequencing (QIFNAS), stepwise ligation and cleavage, fluorescence resonance energy transfer, molecular beacons, TaqMan reporter probe digestion, pyrosequencing, fluorescent in situ sequencing (FISSEQ), wobble sequencing, multiplex sequencing, polymerized colony (POLONY) sequencing (see, e.g., US 2012/0270740); nanogrid rolling circle (ROLONY) sequencing (see, e.g., US 2009/0018024), allele-specific oligo ligation assay sequencing, sequencing on an NGS platform, or any suitable sequencing procedure. Non-limiting examples of NGS platforms include systems from Illumina® (San Diego, Calif.) (e.g., MiSeq™, NextSeq™, HiSeq™, and HiSeq X™), Life Technologies (Carlsbad, Calif.) (e.g., Ion Torrent™), and Pacific Biosciences (Menlo Park, Calif.) (e.g., PacBio® RS II).

A location-specific nucleotide sequence (e.g., a barcode) may be at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides in length.

A target-specific nucleotide sequence may be at least 10, at least 11, at least 12, at least 13, at least 14, at least 15, at least 16, at least 17, at least 18, at least 19, at least 20, at least 21, at least 22, at least 23, at least 24, at least 25 nucleotides, at least 26, at least 27, at least 28, at least 29, at least 30, at least 40, at least 50, at least 75, or at least 100 nucleotides in length.

At least one location on a microarray may be further marked with a unique molecular identifier tag. Unique molecular identifiers may be used to quantify growth (e.g., growth of a microorganism colony or replication of cells at the location). Unique molecular identifiers may be random nucleotide sequences. Methods using unique molecular identifiers and examples of unique molecular identifiers have been described in the art, see, e.g., WO 2013/173394, which is incorporated by reference herein in its entirety. For example, a unique molecular identifier tag may have the nucleotide sequence NNNANNNCNNNTNNNGNN-NANNNCNNN (SEQ ID NO:1), wherein the Ns (equal random mix of ACGT) create a large encoding space so that each molecule amplified gets a unique (specific) DNA sequence barcode (4^N barcodes, or 4^21~4 trillion in this example) This sequence can be counted without interference from amplification bias or other technical problems. The fixed bases in SEQ ID NO:1 (the A, C, G, T) help with reading the barcode accurately, e.g., handling indels.

The present disclosure encompasses using location-specific tags to monitor the presence or amount of more than one target-specific nucleotide sequence in a sample (e.g., multiplexing). At least one location on a microarray may be further marked with a second unique tag comprising a nucleic acid molecule comprising, for example: (i) an amplification primer binding site; (ii) a location-specific nucleotide sequence; and (iii) a target-specific nucleotide sequence.

In some embodiments, a nucleic acid molecule may comprise a target-specific nucleotide sequence without comprising a location-specific nucleotide sequence. In certain embodiments, a nucleic acid molecule may comprise a target-specific nucleotide sequence without comprising either a location-specific nucleotide sequence or an amplification binding site sequence. In further embodiments, a nucleic acid molecule may comprise only a target-specific nucleotide sequence. In even further embodiments, a nucleic acid molecule may contain only a target-specific nucleotide sequence. The target-specific nucleotide sequence may be at least 10, at least 11, at least 12, at least 13, at least 14, at least 15, at least 16, at least 17, at least 18, at least 19, at least 20, at least 21, at least 22, at least 23, at least 24, at least 25 nucleotides, at least 26, at least 27, at least 28, at least 29, at least 30, at least 40, at least 50, at least 75, or at least 100 nucleotides in length. In certain embodiments, the target-specific sequence may be the same at every location in the microarray. Additional target-specific nucleotide sequences may be monitored. For example, one or more locations may be marked with at least 10, at least 25, at least 50, at least 75, or at least 100 unique tags, wherein each tag comprises a target-specific nucleotide sequence that is different from the other target-specific nucleotide sequences in the tags at that location.

Any genetic locus of interest may provide a target-specific nucleotide sequence. For example, sequences of bacterial 16S ribosomal RNA (rRNA), 18S ribosomal RNA, poly(A) RNA, an RNA polymerase gene, a DNA polymerase gene, the RecA gene, a transposase gene, ribosomal internal transcribed spacer (ITS) sequences, a gene encoding an enzyme, control region DNA sequences, binding site DNA sequences, or a portion of any of these sequences may serve as a target-specific nucleotide sequence. A disclosed system, kit, apparatus, or method may use one or more of the bacterial 16S rRNA primers described in Sundquist et al., "Bacterial Flora-Typing with Targeted, Chip-Based Pyrosequencing," 7:108 *BMC Microbiology* (2007) and Wang et al., "Conservative Fragments in Bacterial 16S rRNA Genes and Primer Design for 16S Ribosomal DNA Amplicons in Metagenomic Studies," 4:10 *PLoS ONE* e7401 (2009), each of which is incorporated herein by reference in its entirety.

A sample used in the disclosed apparatuses and methods may comprise a plurality of nucleic acid molecules. A sample may comprise at least one DNA molecule or at least one RNA molecule. A sample may comprise at least one nucleic acid molecule formed by restriction enzyme digestion. A sample may comprise at least one cell (e.g., an archaebacterial cell, a eubacterial cell, a fungal cell, a plant cell, and/or an animal cell). A sample may comprise at least one microorganism. A sample may comprise one or more viruses (e.g., a bacteriophage), for which host cells may need to be provided. A portion of a sample at a location on a microarray may be a single cell or a colony grown from a single cell. For example, individual microorganisms or cells may be placed in microwells and the individual microorganisms or cells may be allowed to divide or replicate so that a colony grows within each microwell that had an individual microorganism or cell placed in it. A location on a microarray may thus contain a single microorganism species or a mixed community of microorganism strains that support one another's growth. A sample may comprise any suitable dilutant. In non-limiting examples, a sample comprises soil, sewage, fecal matter, contents of a body cavity, a biological fluid, living organic matter, dead organic matter, a microbial suspension, naturally-sourced freshwater, drinking water, seawater, wastewater, supercritical carbon dioxide, a mineral, a gas, a buffer, alcohol, an organic solvent, and/or an oil. In some embodiments, a nucleic acid molecule comprising (a) (i) a location-specific nucleotide sequence and (ii) one or more target-specific nucleotide sequences; or (b) one or more target-specific nucleotide sequences (i.e., not comprising a location-specific nucleotide sequence) is placed on at least one location on a microarray before a portion of a sample is placed at the location. In other embodiments, a nucleic acid molecule comprising (a) (i) a location-specific nucleotide sequence and (ii) one or more target-specific nucleotide sequences; or (b) one or more target-specific nucleotide sequences (i.e., not comprising a location-specific nucleotide sequence) is placed on at least one location on a microarray after a portion of a sample is placed at the location. In one example, a sample or a portion of a sample may be placed on a microarray and incubated before a nucleic acid molecule comprising at least one of: (i) a location-specific nucleotide sequence and (ii) a target-specific nucleotide sequence is placed on the microarray. In some embodiments, a portion of the portion of a sample may be removed from at least one location on the microarray and stored in a separate receptacle or the microarray may be split either before or after the nucleic acid molecules are placed on at least one location on the microarray.

At least one location-specific tag may comprise a nucleic acid molecule or a portion of a nucleic acid molecule that is pre-synthesized and placed at the location by a liquid handling procedure. For instance, a liquid handling procedure may be pipetting, spotting with a solid pin, spotting with a hollow pin, or depositing with an inkjet device. A tag may be generated at the location using multiple nucleic acid molecules that are pre-synthesized separately. At least one tag may comprise a nucleic acid molecule that is synthesized at the location by in situ synthesis (e.g., by inkjet printing or by photolithography).

Digital Enumeration of Species

A high density chip device comprised of a surface having high density microwells is described herein. Microbes from a microbiome sample may be diluted and applied to the device such that wells contain approximately one microbe per occupied well. The chip then may be incubated such that the microbes replicate within the wells. Further, a DNA based locational indexing system is described herein to determine what species is present in each well. This indexing system may involve having PCR primers preloaded into each well that contain addressing barcodes that identify the well and a primer sequence targeted to a specific genetic element (e.g., 16S) in the microbial genome that provides species information or targets a desired genetic sequence. After incubation, the microbial DNA is released, the PCR primers amplify the target bacterial DNA region, and the amplicons from the various wells on a chip are pooled and then may be read next generation sequencing.

The systems, kits, apparatus, and methodologies described herein may be utilized to perform an absolute count of the number of each microbial species or variant in a sample. Each well may represent a digital event which represents the presence of a single microbe in the original diluted sample. The locational indexing system may allow a user to determine what bacterial species is in the well. A unit of measurement may be "there is a bacterial species in a well" and may be independent of the number of bacteria in the well.

In one example, a mixed sample of microbes includes 50% Species 1, 30% Species 2, and 20% Species 3. The sample is diluted then applied to the chip such that each occupied well has, for the most part, one microbe. The microbe replicates. Note the replication rate may be different for different species. Then, the chip is processed such that the DNA from the microbes in the wells is released and the 16S or some other target sequence is amplified. The DNA amplification products from each well may be pooled and sequenced using next generation sequencing. The next generation sequencing data may be analyzed to determine, for each well, what species is in each occupied well. Many wells may not be occupied at all. The abundance of each species may be determined by: the total number of wells occupied by each species divided by the total number of occupied wells. An absolute abundance determination may be made by multiplying the % abundance of each species from step by the total number of microbes in the original sample. The sequencing data may be compared to publicly available sequence datasets to determine what species is in each occupied well. For example, ribosomal RNA sequence data is available in the SILVA rRNA database project described above. Other ribosomal RNA sequence databases include the Ribosomal Database Project, Greengenes, and the GenBank® genetic sequence database, also described above.

Current methods for estimating the abundance of microbial species in a sample involve the use of traditional techniques such as microscopy, staining, selective media, metabolic/physiological screens, and cultivation using petri dishes. These methods are often inaccurate due to lack of specificity (microscopy, staining, metabolic/physiological screens) or lack of ability to account for all species in a sample (selective media, cultivation) whereby many species do not grow well or do not grow at all with traditional approaches.

Current molecular methods for determining the relative abundance of microbial species in microbiome samples involve extracting microbial DNA from samples, performing PCR amplification of the 16S or some other DNA region that provide species or other information, then performing next generation sequencing (NGS) on the resulting PCR product. The relative abundance of each species in the original sample is inferred from the relative frequency of the species specific DNA sequence in the NGS data. There are many examples in the literature of this type of analysis and this method underpins much microbiome research.

The problem with the current methodology is that it does not control for different numbers of 16S gene that may exist in different microbes, PCR bias whereby sequences from different microbial species may be amplified at different rates, and sequencing bias where sequences from different microbial species may be sequenced at different rates. The result is that there is a lot of uncertainty with respect to the accuracy of relative abundance data derived using current methodologies.

The counting of different species may be based on the presence of a species in a single well. This is directly related to a single microbe from the original sample partitioning into the well during loading. Only PCR/NGS may be used to identify what microbial species exists in each well. The number of sequences identified does not form part of the calculation. Hence, it does not matter if there is PCR, NGS, or target sequence copy number variance or bias in the method.

Some embodiments may have applications in microbiome research, microbial product discovery and development, clinical diagnostics, and any other area where accurate counts of microbial species in a sample are required.

Accordingly, some embodiments may provide a much more accurate measurement of the relative abundance of each species in a microbiome sample, and the ability to convert this relative abundance measurement into an absolute abundance or a direct count of each species in the original sample (by accounting for the dilution and/or combining with a measurement of the total number of microbes in the original sample). Some embodiments may provide new applications for high density microfabricated chips (in addition to cultivation and screening of microbes).

Figure 18:
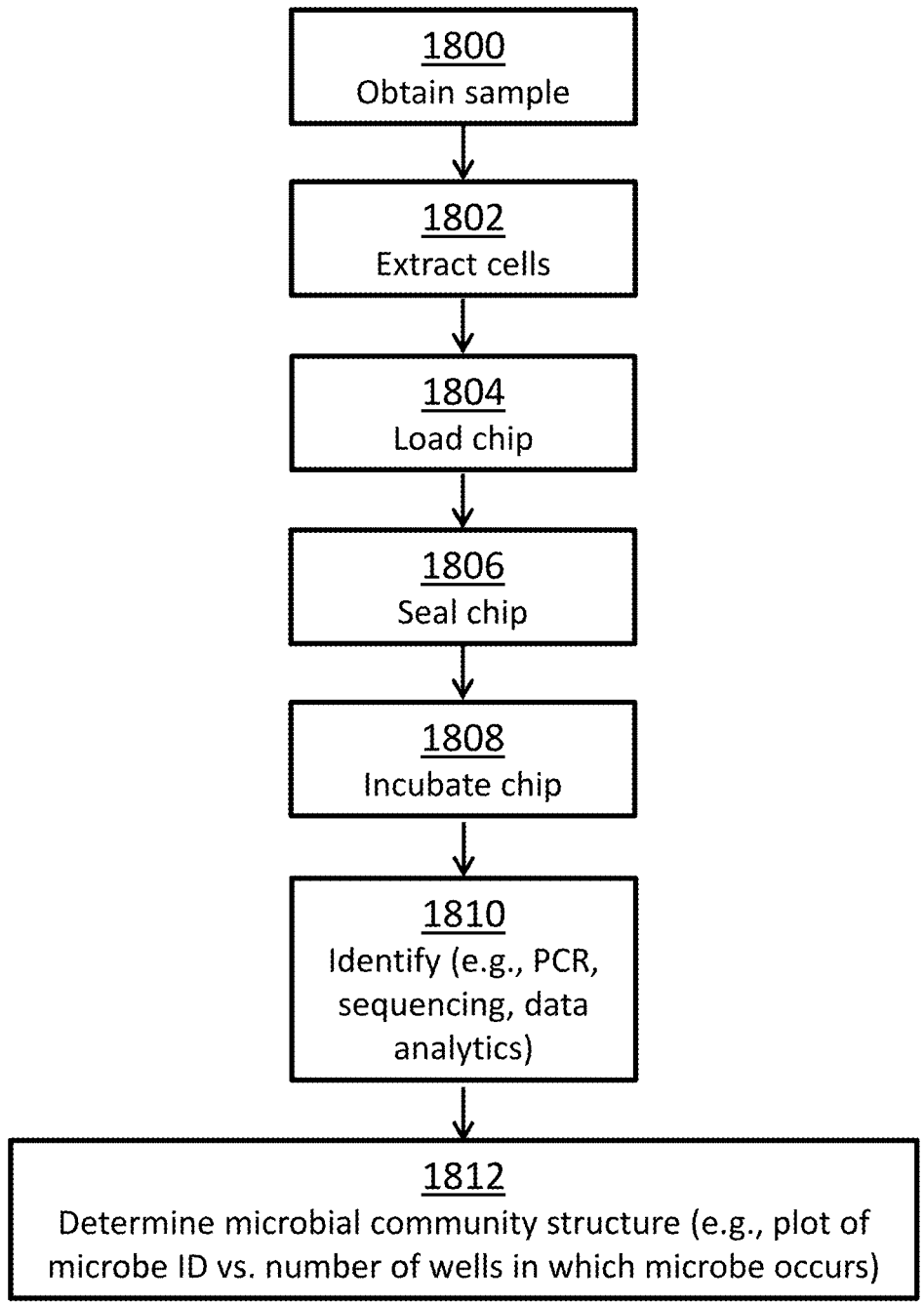
FIG. 18 is a flowchart illustrating a counting method in accordance with some embodiments.

FIG. 18 is a flowchart illustrating a counting method in accordance with some embodiments. In step 1800, a sample is obtained. In step 1802, at least one cell is extracted from the obtained sample. In step 1804, at least one high density microwell array of a microfabricated device or chip is loaded with the at least one extracted cell. Step 1804 may include preparing a cell concentration with the at least one extracted cell, selecting at least one nutrient/media, and/or selecting at least one membrane. In step 1806, at least a portion of the microwell array is sealed with the at least one selected membrane to retain the cell concentration with the microwells. In step 1808, the chip is incubated. Step 1808 may include selecting a temperature, determining atmosphere (e.g., aerobic or anaerobic), and/or timing incubation). In step 1810, the cultivated cells may be sacrificed for identification. Step 1810 may include PCR, sequencing, and/or various data analytics. In step 1812, information about the sample (e.g., a microbial community structure) may be assessed and/or determined.

Figure 19:
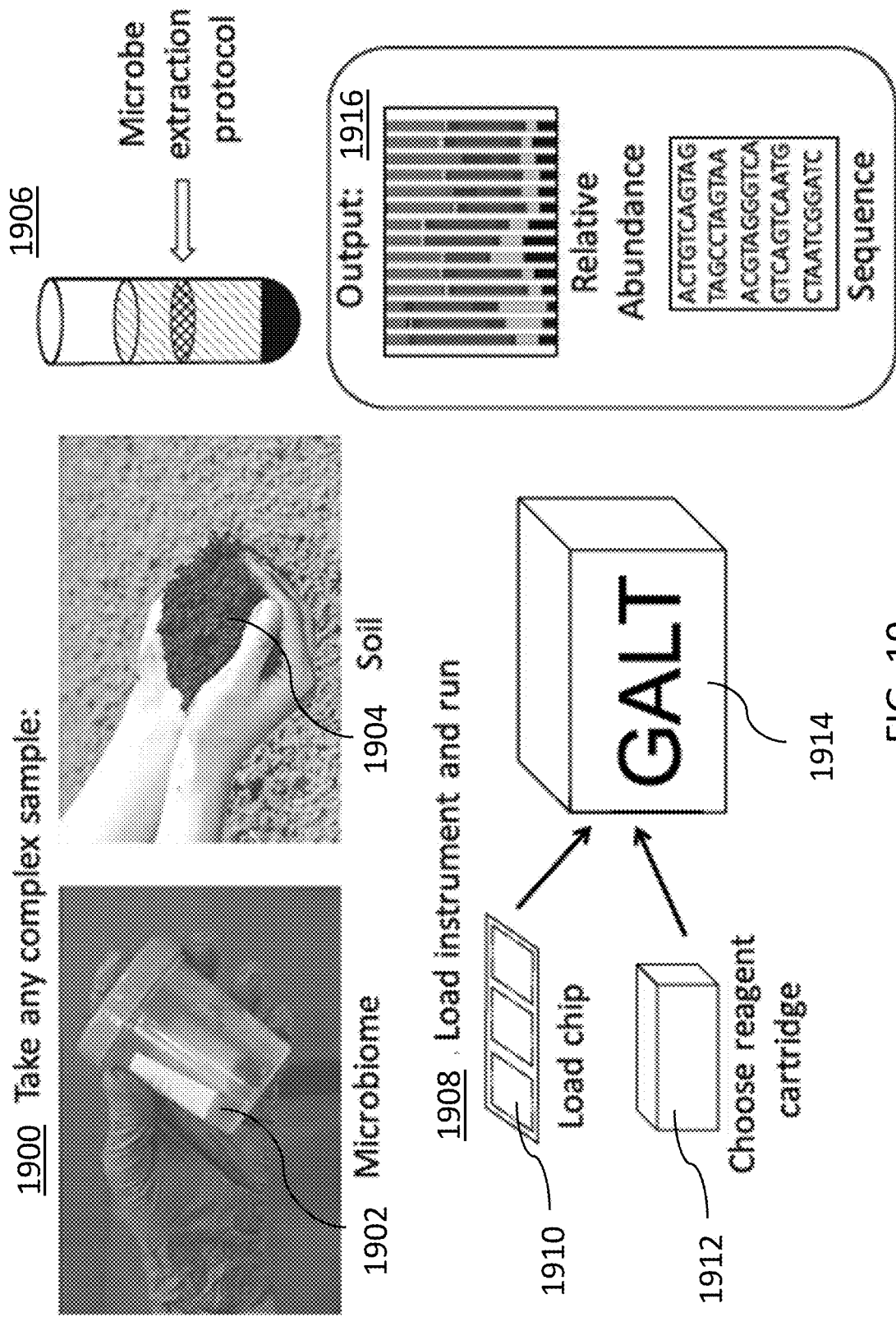
FIG. 19 is a diagram illustrating a counting method in accordance with some embodiments. Panel 1916 shows the output: sequences and relative abundance of cultivated cells (SEQ ID NOs: 2-6).

FIG. 19 is a diagram illustrating a counting method in accordance with some embodiments. Panel 1900 shows examples of complex samples, specifically a microbiome sample 1902 and a soil sample 1904. In Panel 1906, at least one cell is extracted from the sample using, for example, the protocol illustrated in FIGS. 5A and 5B. In Panel 1908, the at least one extracted cell (and any environmental extract and/or dilutant) is loaded on a microfabricated device or chip with at least one high density microwell array 1910. Chip 1910 and a reagent cartridge 1912 may be loaded into an incubator 1914. The reagent may be useful for adding liquid to maintain nutritional requirements for growth and/or various screening purposes. Panel 1916 shows the output: sequences and relative abundance of cultivated cells (SEQ ID NOs: 2-6).

Droplet-Based Platforms

A discrete droplet-based platform may be used to separate, cultivate, and/or screen in much the same way that chips are used. A droplet is an analog of a microwell serving as a nano- or picoliter vessel. Droplet generation methods, especially when combined with cell-sorter-on-a-chip type instrumentation, may be used to separate out microbes from a complex environmental sample. Droplet addition may be used to feed microbes. Droplet splitting may be used for sequencing or some other destructive testing while leaving behind a living sample. All the prep work necessary for sequencing may be done in droplet format as well.

Some embodiments may be used to get microbes out of a complex environment and into droplets. For example, a modular system for generating droplets containing cell suspensions may contain one or small numbers of cells. The aqueous drops may be suspended in a nonmiscible liquid keeping them apart from each other and from touching or contaminating any surfaces. Droplets may be generated at, for example, 30 Hz in each microchannel, which translates into millions per day.

A drop-based microfluidic system may encapsulate, manipulate, and/or incubate small drops (e.g., about 30 pL). Cell survival and proliferation is noted to be similar to control experiments in bulk solution. Droplets may be produced at several hundred Hz, meaning millions of drops can be produced in a few hours. A simple chip-based device may be used to generate droplets and the droplets may be engineered to contain a single cell.

Some embodiments may be used to screen cells in droplets. Fluorescence screening of droplets post-incubation may be done on-chip and at a rate of, for example, 500 drops per second. Droplets may be flowed through a channel at the focus of an epifluorescence microscope that may be configured for a number of different measurements. This may be a particularly effective way to do screening for metabolites as the local concentration is quite high on account of being confined to a very small droplet.

Some embodiments may be used to sort droplets. Once cells have been isolated, grown, and/or screened, they may be sorted so that useful samples may be retrieved. Droplets may be sorted in an analogous way to the commonly used FACS machine.

Some embodiments may be used to split droplets. Some embodiments may require the ability to take a sample and split it in order to send one portion to sequencing (a destructive process) and retain another portion that is a viable culture. There are a number of different ways to split droplets including, but not limited to, constructing T-junctions with carefully calculated dimensions that result in drops splitting as they flow by or electrowetting (taking care not to cause cell lysis with voltages that are too high).

Some embodiments may be used to merge droplets and/or add a reagent to a droplet. For example, long term incubation of cells (e.g., weeks) requires the ability to add liquid to maintain nutritional requirements for growth. It also may be useful to be able to add reagents for various screening purposes. Droplet screening relies on being able to merge a droplet containing a compound-code with a droplet containing a single cell. The droplets then may be incubated and/or returned to an assay chip to identify compounds via their codes. This may require the ability to precisely merge drops on an as-needed basis.

Some embodiments may be used to perform PCR in droplets. PCR may be used in order to ultimately sequence a specific genetic element (e.g., the 16S region) in order to identify microbes. This may be used to determine what type of microbe is growing in each well. In a droplet-based system this approach may be used to determine what microbe is present in each droplet as long as the correct primer sequence is designed to amplify the right region of the genome.

Some embodiments may be used to sequence DNA out of droplets (e.g., generated in the PCR step) and/or prepare DNA libraries.

Location Specific Tags for High Density Chips

A high density chip device having a surface with a high density of microwells may be used. Microbes from a microbiome sample may be diluted and applied to the device such that wells contain approximately one microbe per occupied well. The chip may be incubated such that the microbe replicates within the well and the resulting population represents a single species. A DNA-based locational indexing system may be used to determine what species is present in each well. This indexing system may involve having PCR primers preloaded into each well that contain addressing barcodes that identify the well, and a primer sequence targeted to a specific genetic element (e.g., 16S in the microbial genome) that provides species information. After incubation the microbial DNA may be released, the PCR primers may amplify the target bacterial DNA region, and the amplicons from the various wells on a chip may be pooled and then read by next generation sequencing.

The above locational indexing system may involve incorporating a different locational code for each well of the microchip, or multiple locational codes may be incorporated into each well such that the total number of codes required to code a specified number of wells is reduced. For example, if there are 100 wells in a chip it would require 100 codes if there is one code per well. The same chip could be coded with only 20 codes if two codes were read from each well (i.e., 10 coding for the x axis of the grid and 10 coding for the y axis).

An example of a PCR strategy to incorporate two codes per well is provided in TABLE 2

TABLE 2

| Primers | Amplified PCR Products |
| --- | --- |
| 5'- CODE1-TARGETSEQUENCEPRIMER1-3'<br>3'- TARGETSEQUENCEPRIMER2 - CODE2 - 5' | CODE1 - TARGETSEQUENCE-CODE 2 |

An example of a PCR strategy to incorporate three codes per well provided in TABLE 3.

TABLE 3

| Primers | Amplified PCR Products |
| --- | --- |
| 5'- CODE1-TARGETSEQUENCEPRIMER1-3'<br>3'- TARGETSEQUENCEPRIMER2 - CODE2 - ADAPTER 5'<br>3'- ADAPTER' - CODE3' 5' | CODE1 - TARGETSEQUENCE-CODE<br>2- ADAPTER - CODE3 |

Three oligo primers are used to make a single PCR product. Advantages to this system using two oligos to put a multi-partite barcode on one end of the molecule may include, for example, reducing maximum length of oligos needed or making extra-long barcodes.

This approach can be generalized to incorporate n barcodes per reaction. The approach can also have different implementations such that the barcodes are on the same side of the target sequence region. NGS sequencing adaptors may be added, and the full sequence for the population of barcoded PCR products may be read using next generation sequencing.

In another implementation, a fixed code may be added to indicate sample number or plate number and allow pooling of multiple samples/plates in a run for two barcodes as shown in TABLE 4.

TABLE 4

| Primers | Amplified PCR Products |
| --- | --- |
| 5'- PLATEA - CODE1 - TARGETSEQUENCEPRIMER1-3'<br>3'- TARGETSEQUENCEPRIMER2 - CODE2 - 5' | PLATEA - CODE1 - TARGETSEQUENCE - CODE 2 |

In another implementation, a fixed code may be added to indicate sample number or plate number and allow pooling of multiple samples/plates in a run for three barcodes as shown in TABLE 5.

TABLE 5

| Primers | Amplified PCR Products |
| --- | --- |
| 5'- PLATEA - CODE1 - TARGETSEQUENCEPRIMER1-3'<br>3'- TARGETSEQUENCEPRIMER2 - CODE2 - ADAPTER 5'<br>3'- ADAPTER' - CODE3' 5' | PLATEA - CODE1 - TARGETSEQUENCE - CODE 2 - ADAPTER - CODE3 |

Note that in all cases the position of the barcode in the sequence conveys information hence the CODE1, CODE2, and CODE3 barcodes do not necessarily have to be different from each other in a particular well.

Making oligos and printing chips using a single code coding system are high cost. For example, a 10,000 well chip requires 10,000 single barcodes and 10,000 separate printing cycles to place those barcodes into the wells on the chip. If a two-code system is used, then potentially only 200 barcodes are required with only 200 printing cycles to manufacture chips. This represents a significant saving in oligo cost, printing time and printing capital investment.

The use of dual barcoded PCR primers, followed by amplification and sequencing analysis, to provide locational data on DNA or DNA containing moieties randomly partitioned onto a microfabricated chip may have high utility and relatively low cost.

Figure 20:
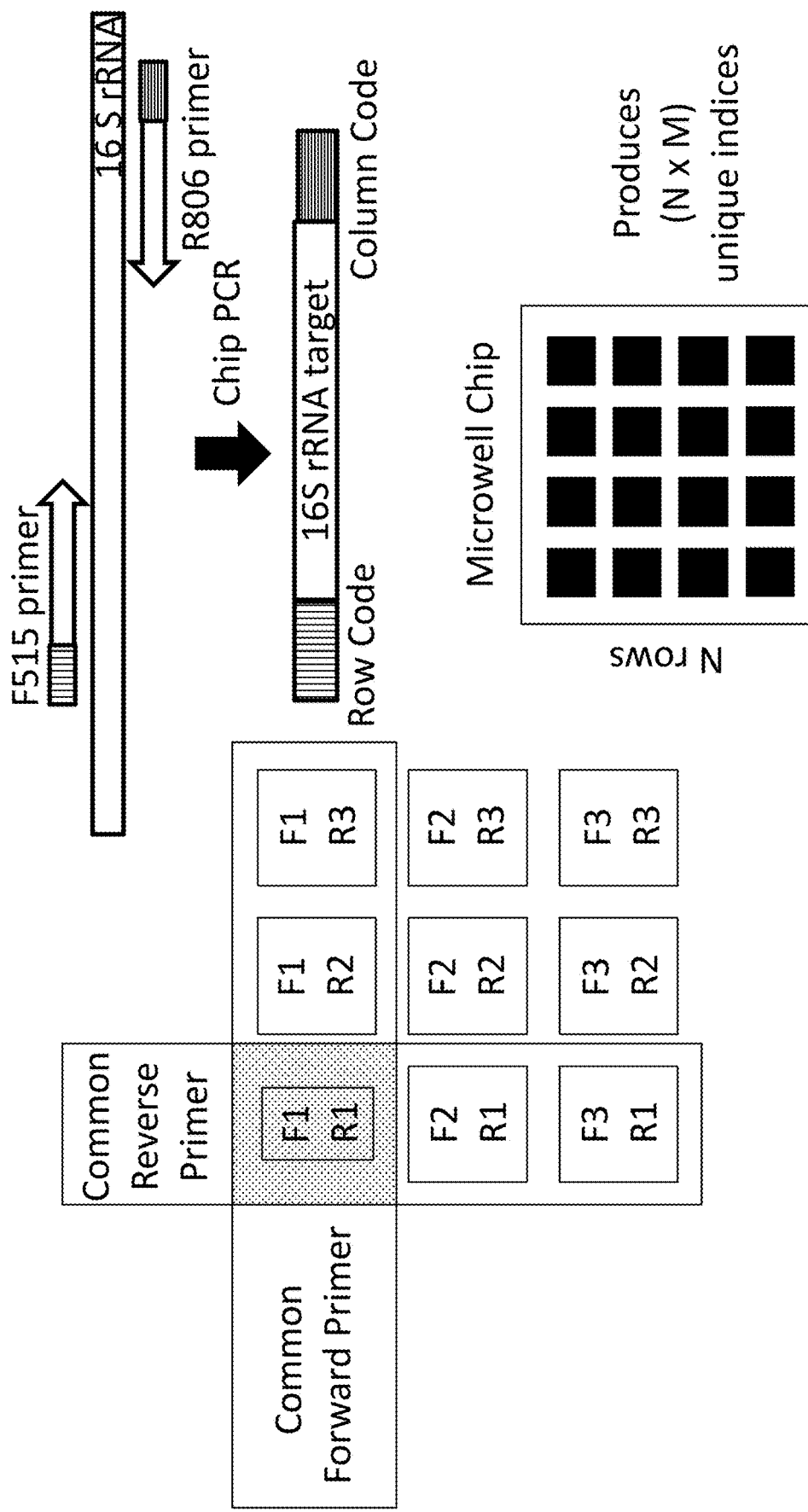
FIG. 20 is a diagram illustrating an indexing system in accordance with some embodiments.

FIG. 20 is a diagram illustrating an indexing system in accordance with some embodiments. Microwell chip 2000 has N rows and M columns, thereby producing N×M unique indices. A location of a microwell in chip 2000 may be considered to have the coordinates (N, M). Each column has a common reverse primer sequence (e.g., R1, R2, R3, . . . RM), and each row has a common forward primer sequence (e.g., F1, F2, F3, . . . FN). For example, a unique tag targeted to a specific genetic element in, for example, 16S ribosomal ribonucleic acid (rRNA) may include forward primer sequence F515 and reverse primer sequence R806. Following PCR of chip 2000, the presence of the targeted genetic element may be mapped back to a unique microwell of origin based on the presence of a forward primer sequence and a reverse primer sequence. For example, the presence of F515 and R806 directs a user to the microwell with coordinates (515, 806) in chip 2000.

Variability Reduction for PCR Amplification Product Across Microwells Containing Bacteria A DNA-based locational indexing system may be used to determine what species is present in each well. This indexing system may involve having PCR primers preloaded into each well that contain addressing barcodes that identify the well, and a primer sequence targeted to a specific genetic element (e.g. 16S) in the microbial genome that provides species information. After incubation the microbial DNA may be released, the PCR primers amplify the target bacterial DNA region, and the amplicons from the various wells on a chip are pooled and then read by next generation sequencing.

Some embodiments for limiting the variability in the amount of PCR product across wells may include limiting amount of PCR primer in the well during manufacture of the chip such that for the majority of possible sample DNA concentrations the amount of PCR primer will limiting in the DNA amplification reaction, hence the amount of PCR product produced will be less variable across wells.

Some embodiments for limiting the variability in the amount of PCR product across wells may include limiting the number of PCR cycles on the chip to less than 3 cycles, or less than 5 cycles, or less than 10 cycles or less than 15 cycles, or less than 20 cycles or less than 25 cycles or less than 30 cycles such that the amount of PCR product produced will be less variable across wells vs. a full cycle PCR amplification protocol.

Some embodiments for limiting the variability in the amount of PCR product across wells may include limiting the amount of nucleotides in the reaction mix so that the number of PCR amplicons produced is a more related to the amount of nucleotides than the amount of DNA in the original sample. Microwells with a large amount of target DNA will exhaust the nucleotides early in the cycling process while microwells with a small amount of target DNA will exhaust the nucleotides later in the cycling process, but produce around the same amount of amplification product.

Some embodiments for limiting the variability in the amount of PCR product across wells may include limiting the amount of nutrient available to microbes growing in the wells such that cells will replicate until the media is exhausted then stop replicating.

Some embodiments for limiting the variability in the amount of PCR product across wells may include placing a dye in each well that identifies PCR product such that the signal gets brighter as more PCR product is produced. The intensity of the dye during each PCR cycle may be monitored, and a sample may be taken from the well once the desired signal intensity is observed.

Some embodiments for limiting the variability in the amount of PCR product across wells may include using mixtures of hybridization beads covered with oligos complementary to each well-specific bar code to selectively hybridize amplified DNA from each well. Once the beads are saturated unbound DNA may be washed away releasing bound DNA from the beads. The amount of DNA from each well will then be normalized at the saturation limit of the beads.

Some embodiments for limiting the variability in the amount of PCR product across wells may include incubating chips for a long period of time such that the fast growing microbes rapidly fill wells and cease replicating, and the slower growing microbes gradually fill wells and cease growing once approximately the same number of cells are in the wells In some embodiments, use of barcoded primers and next generation sequencing (NGS) within the context of the chip format and method may be used to identify which species is growing in which well on the high density microchip. When an approximately equal number of bacteria occupy each microwell in the chip, the signal from each well in the NGS data may be approximately the same.

For example, in a typical NGS run generating 12 million sequence reads, if 24 chips are sequenced in the run, each having 10,000 microwells, and there is the same number of bacteria per well, there is on average 50 reads per well.

However, different bacteria grow at different rates so it is likely that some wells have few bacteria and some wells will have many bacteria. This potentially skews the NGS run so much that the wells with few bacteria are not detected in the NGS analysis.

Hence, in the example of a typical NGS run generating 12 million sequence reads, 24 chips are sequenced per run, each having 10,000 microwells, half of which have 100 times more bacteria in them than the other half. The probability that the bacteria in the slow growing wells are detected is markedly reduced. In this case:

$$(10,000 \times 24)/2 \times 100 = 12,000,000 \qquad (1)$$

$$(10,000 \times 24)/2 = 120,000 \qquad (2)$$

The low frequency wells are represented at 1% of total. So of 12,000,000 reads in an NGS run 120,000 will be from the low frequency wells—i.e. average of 1 read per well.

To minimize the impact of this phenomenon novel methods need to be developed to help equalize the amount of PCR product across wells so that all wells are detected in the NGS run.

Silicon-Based Microwell Chips for Microbial Isolation, Growth, Screening, and Analysis A microfabricated device or chip may be composed at least in part of silicon instead of or in addition to plastic, glass, and/or polymers to allow for electrical measurements on a well-by-well basis. For example, the walls of each well may be isolated to create microcapacitors. In another example, an FET in each well such that the gate surface is exposed to the contents of the well. Instead of a purely silicon-based chip, thin metal layers may be generated on top of an existing chip by plating, vapor deposition, and/or arc/flame spraying. This may add more functionality to a chip, utilize alternate methods of manufacture which may be cheaper and/or cleaner, and/or allow miniaturization for handheld and/or portable devices.

Some embodiments may allow for monitoring growth by electrical measurement. Impedance monitoring may be applied to measure microorganism (e.g., bacterial) growth. For example, impedance across a tube containing *Escherichia coli* (*E. coli*) is compared to cell counts therefrom in Ur et al., "Impedance Monitoring of Bacterial Activity," 8:1 J. Med. Microbiology 19-28 (1975), which is incorporated herein by reference in its entirety. Measurements may be taken on other types of bacteria including *Pseudomonas*, *Klebsiella*, and *Streptococcus* to demonstrate the effect is general. Wells may be filled with different media in order to test growth conditions across different formulations.

Some embodiments may allow for screening by electrical measurement. Electrical measurements may be made on a well-by-well basis allowing for screening. One example would be pH. There are a number of different ways to get a pH-dependent response from the gate of a device in a well including, but not limited to, ISFETs and pH-meters. An array of wells with embedded pH sensors may determine, electrically, which wells contain microbes that are producing acidic or basic metabolites. A simple example is screening for the production of lactic acid from lactose. Bacteria is diluted out into wells, grown, and then fed lactose. Wells that record a drop in pH contain microbes capable of metabolizing lactose into lactic acid.

Some embodiments may allow for electrical measurements of redox probes. Another way to leverage electrical measurements is to look at how bacteria in wells affect a known redox probe. Essentially, a system with well-defined response may be measured in the presence of bacteria and deviations from expected behavior may be attributed to the bacterial samples. A typical redox probe is something like ferricyanide; [Fe(CN)6]3−/4−. The reduction of ferricyanide to ferrocyanide is very well characterized such that small changes in behavior, particularly around electron transfer from the electrodes, are discoverable. This system is "label free" as it detects without having to directly modify the bacteria themselves.

Antibodies that can recognize microorganisms (e.g., *E. coli*) may be immobilized on ITO electrodes. Electron transfer resistance may be measured from the electrodes to a ferricyanide containing solution. *E. coli* binding to the electrode surface increases the resistance proportional to the concentration of *E. coli* on the surface. This is one example of a family of measurements that may be made to detect specific types of organisms or metabolites using redox probes.

Working in silicon (or at least metals or metallized plastics) provides advantages including, but not limited to, less expensive production of chips (e.g., by piggybacking on existing technologies); integrated detection capability allowing small and/or portable versions; additional measuring capabilities not present in other materials (e.g., LCR, CV, etc.); integration of newly discovered chip-based detection modalities into existing devices; and the combination of electrical measurements and sequencing. These advantages would benefit any customer using interferometric detection.

Releasable Barriers to Protect Well-Specific Chemistries on a Chip

FIGS. 21A-21E are diagrams illustrating a chip with well-specific chemistries in accordance with some embodiments. In FIG. 21A, a microfabricated device or chip is shown with a plurality of microwells. In FIG. 21B, microwell-specific chemistries have been disposed in each microwell of the chip. In FIG. 21C, a sealant has been applied over the microwell-specific chemistries in each microwell of the chip, thereby preventing interaction of the chemistries with further additions to the wells. In FIG. 21D, samples are loaded, and experiments are performed on the samples in the microwells. In FIG. 21E, a trigger (e.g., heat) releases the microwell-specific chemistries for interaction with samples in the wells.

Microwell chips may be manufactured, be cleaned, and/or have surfaces treated. The specific chemistries may be prepared separately and then deposited into wells by, for example, using a method and/or device that allows a specific set of chemicals to be directed to a specific well (or wells). A sealant then may be applied to protect the various chemistries from the environment and/or be removed/released/disbursed with some defined, external trigger.

A microfabricated device or chip may be manufactured to a specific design, for example, cleaned and/or surface treated to improve wetting. PCR primers may be printed or pin-spotted into specific wells. The chip may be allowed to dry, and then a wax layer may be deposited by evaporation from an ethanol solution. Optimal concentration may be about 1% v/v. Molten wax may be applied directly or an aqueous or alcohol wax solution may be sprayed. Alternatively, spin coating or vapor deposition may be used. Various waxes may be used including, but not limited to, glyceryl stearate with and without polyethylene glycol, cetearyl alcohol, 1-hexadecanol, glyceryl ester of stearic acid, ceteareth-20 (CAS Registry No. 68439-49-6), and some commercial products including, but not limited to, Lotionpro™ 165 (available from Lotioncrafter®, Eastsound, Wash.) and Polawax™ (available from Croda, Inc., Edison, N.J.). The underlying chemistry later may be released by, for example, heating until the wax melts. For these compositions it will be between 50° C. and 70° C. It is important to be low enough not to damage any chemical component or to boil our aqueous solutions.

The key concept is of well-specific chemistry that is walled off from the chip until the experimenter triggers release. This method may be used for barcoding in wells, but it also may be applied more broadly to a whole range of different problems. Different chemistries that may be useful to seal on a chip include, but are not limited to, antibiotics, fluors, dyes, PCR primers, lysis-promoters, antibodies, and/ or tests for various metabolites. While wax is a good way to seal things that can later be released by heating, other materials may be used to seal and release upon exposure to light, sonication, and/or some other trigger. The advantage of this method over simply adding reagents to the chip is one of control on a well-by-well basis. A similar effect might be achieved by printing chemicals into wells after doing microbial experiments, but this introduces problems with time (the print run may be as long as a day) and the fact that it is impossible to expose every well for the same amount of time if each well is filled individually after the microbes are on the chip. With a release mechanism every well can be exposed at the same time. In one example, wax may be deposited onto chips by solvent casting.

Isolated Microwells for Simplicity and/or Controlling Relative Abundance

A high-density chip device may comprise a surface having high-density microwells. Microbes from a microbiome sample, or other cell types, may be diluted and applied to the device such that wells contain approximately one microbe or cell per occupied well. These microwells may be sealed with semi-permeable membranes that allow nutrients to diffuse into the microwells but prevent all or at least some of the microbes or cells from moving out of the microwells.

A sample of microbes or cells may be prepared and then sealed into a chip using an impermeable or only-gas-permeable membrane. No reservoir of liquid sits on top of the chip or membrane and hence only the nutrient in the well at the time of sealing is available to support growth of the microbes or cells in the microwell. Two reasons for this feature include: (1) simplicity in construction and workflow as the device need not have semi-permeable membranes or reservoirs, nutrients do not have to be added, and there is less potential for contamination; and (2) a check on the relative abundance of fast-growers by limiting their access to nutrients. For a sample containing some fast-growers and some slow-growers, the fast-growers will rapidly be resource-limited in their respective microwells and stop or slow growth while the slow-growers continue to grow. This provides for slow growers to be represented at a higher relative abundance in the population of microbes across the chip, compared to the case where the fast growers do not have a limiting amount of nutrient. This becomes important for downstream processing when sequencing everything on a chip. It also provides a better detection limit for rare species as the rare species are not outgrown by fast growing species to a point that limits the ability of the system to detect them.

Current methods attempt to get all species to grow whether they are fast- or slow-growing by nature. This has the inevitable result that fast-growers dominate communities and only increase in relative abundance with time. Many types of downstream analysis such as sequencing or fluorescence screening cannot resolve every species in a given population but only those above a certain limiting relative abundance. If the goal is to preserve diversity and detect rare species, then the fast-growers need to be limited in some way.

For an example that demonstrates this idea, consider the simple case of a sample containing two species: one doubles every day and the other doubles every week as shown in TABLE 6. If the slow-grower is rare to begin with, at 5% relative abundance, it soon becomes very rare as both species grow.

TABLE 6

| Unlimited | Day 0 | Day 1 | Day 2 | Day 3 | Day 7 | Day 14 |
| --- | --- | --- | --- | --- | --- | --- |
| Fast grower | 19 | 38 | 76 | 152 | 2432 | 311296 |
| Slow grower | 1 | 1 | 1 | 1 | 2 | 3 |
| Total | 20 | 39 | 77 | 153 | 2434 | 311299 |
| Rel. ab. fast | 0.950 | 0.974 | 0.987 | 0.993 | 0.999 | 1.000 |
| Rel. ab. slow | 0.050 | 0.026 | 0.013 | 0.007 | 0.001 | 0.000 |

If the fast-growers are limited by competition for nutrition and/or physical space to grow, then the relative abundance of the slow-growers will start to increase after some time has elapsed as shown in TABLE 7.

TABLE 7

| Limited | Day 0 | Day 1 | Day 2 | Day 3 | Day 7 | Day 14 |
| --- | --- | --- | --- | --- | --- | --- |
| Fast grower | 19 | 38 | 50 | 50 | 50 | 50 |
| Slow grower | 1 | 1 | 1 | 1 | 2 | 3 |
| Total | 20 | 39 | 51 | 51 | 52 | 53 |
| Rel. ab. fast | 0.950 | 0.974 | 0.980 | 0.980 | 0.962 | 0.943 |
| Rel. ab. slow | 0.050 | 0.026 | 0.020 | 0.020 | 0.038 | 0.057 |

High Density Microfabricated Arrays for Biobanking Cells

Biobanks are designed to give researchers access to a large number of samples from a large population in order to drive certain types of research, such as disease-related biomarker discovery. The current state of the art in biobanking provides for samples to be stored in tubes or low-density plate format such as a 96-well or 384-well plate. This works when the number of samples to be stored is relatively low in number and the samples themselves are discrete, isolated populations. Current approaches to biobanking become very cumbersome when storing samples, such as microbiome samples, where the number of samples may be high and the number of different species or variants in each sample may extend from hundreds to thousands or many millions per sample. Using current methods, a laborious isolation protocol must be implemented to separate out individual species or variants either prior to or subsequent to the storage step in order to access a desired species or variant.

The systems, kits, apparatus, and methodologies described herein may be applied to biobank cells, microbes, viruses, and other biological entities. A high-density chip device comprised of a surface having high density microwells may have thousands, hundreds of thousands, or millions of microwells per chip. For example, microbes from a microbiome sample (or another biological entity such as a different type of cell or a virus) may be diluted and applied to the device such that wells contain approximately one microbe per occupied well. The chip then may be incubated such that the microbe replicates within the well and the resulting population represents a single species. A nucleic acid-based locational indexing system may be utilized to determine what species is present in each well. This indexing system may involve having PCR primers preloaded into each well. The PCR primers may contain addressing barcodes that identify the well, and a primer sequence targeted to a specific genetic element (e.g., 16S) in the microbial genome that provides species information or targets a desired genetic sequence. After incubation the microbial DNA is released, and the PCR primers amplify the target bacterial DNA region. The amplicons from the various wells on a chip may be pooled and then read by next generation sequencing.

Using high-density microfabricated chips for biobanking provides for a multitude of species or variants within each sample to be stored as separate populations without the need to implement a laborious isolation protocol either before or after storage. Using the DNA-based locational indexing system or a custom assay enables a simpler, generic approach to identifying genetic signatures or characteristics of the contents of each microwell to give information such as, for example, species information. Additionally, the chip devices provide for an extremely space effective method of storing cell isolates. For example, a single microscope slide dimensioned chip with 100,000 wells occupies substantially less space that the corresponding traditional storage formats. The chip format also may be useful for properly archiving and curating samples and/or for managing subject (e.g., patient) information databases by having one chip contain many different samples from a single subject.

In order to bank cells using this apparatus, cells may be disposed and/or positioned in microwells of the apparatus. The cells in the microwells may be treated to ameliorate the impact of storage then placed in appropriate storage conditions. For example, cells may be treated with agents such as glycerol to ameliorate the impact of freezing. Then the chip may be placed in appropriate storage conditions such as a freezer. The cells may be dehydrated, lyophilized, and/or freeze dried, and the chip may be placed in appropriate conditions to safeguard the dried cells. Additional structures may be added to the chip to further enhance its utility as a storage device. For example, a membrane or another structural element may be placed on top of the chip to seal at least some of the wells prior to storage.

A chip may be loaded with cells such that a portion of microwells on the chip are occupied by approximately one cell each. The chip is incubated to allow for replication of cells. The chip is duplicated, and either the original chip or the duplicate chip is used to identify the cells or species or gene signatures present in each well of the chip (by, e.g., using the locational indexing system described above). The chip is treated and/or stored in appropriate conditions. The replication step and/or the identification step may take place after storage rather than before storage.

One or more cells from each strain of a pre-existing set of isolated strains may be disposed into separate microwells on a chip. The position of the microwell into which each strain or cell type was placed may be recorded, and the chip may be treated and/or stored in appropriate conditions.

A version of the chip may be created in which preservative chemistry is sequestered underneath a wax barrier in each well. Isolates may be allowed to grow sealed up inside a chip and then preserved at a later date by heat-induced release of the preservatives before banking.

Such apparatus may be used to store/biobank mixed microbiome samples such as microbiome samples from soil, human gut, seawater, oral cavity, skin, etc. A chip may be used to store other types of biological entities such as fungi, archaebacteria, human cells (including reproductive cells), animal cells, and viruses.

The DNA locational indexing system may be used across all biological entity types to generate information regarding the content of each well. An entire chip may be screened for desired activity using custom assays such as antibody- or substrate-based assays. For example, a chip with banked populations of T cells may be screened for a particular immunological activity.

In one illustrative example, human stool microbiome samples may be collected from study participants. The stool microbes from each individual may be biobanked on chips to maintain both a record of that individual's microbiome as well as a sample of the microbiome to use as a source of target microbes at a later date. In another example, mixed populations of T cells or other immunological cells may be sampled from individuals during clinical or research studies or as part of a therapeutic workflow (e.g., cell therapy using ex vivo treated cells). In yet another example, soil biomes may be stored in conjunction with seed banking.

High Resolution Picking

A high accuracy/precision picking apparatus or system may be designed to execute various picking functions from and/or to microwells on a microfabricated chip described above. A target substrate or chip may be a microscope slide format (approximately 25 mm×75 mm×1 mm) with injection-molded features on one surface. Microwells may be arranged in a grid pattern with about 4-8 mm well-free edge around the edges of the chip. Well size and spacing may be determined based on picker capability. Microwells may be square with a size from about 25 μm to about 200 μm along each edge and spacing in from about 25 μm to about 100 μm between well edges. Microwells may be circular or hexagonal instead. Well depths may be from about 25 μm to about 100 μm. For example, a 75 mm×25 mm slide with a 7 mm edge, 100 μm square wells with 100 micron edge-to-edge spacing will have about 16,775 microwells.

A high accuracy/precision picking system may be designed to execute various picking functions from and/or to portions of a membrane corresponding to microwells on a microfabricated chip, as described above. A membrane may be a thin sheet that has previously been used to seal growing bacteria into microwells. When peeled off the chip the membrane may retain an imprint of the microwell array as well as a sample of bacteria on its surface after separation from the chip. Thus, the peeled membrane may act as a replicate of the bacteria growing in the chip.

A high resolution picker may receive data input from a user. The input may include at least one pair of chip microwell coordinates such that the picker picks from and/or to the at least one input pair of coordinates. A sterilization routine may be performed between cycles. A high resolution picker may be capable of operating in an anaerobic chamber.

A high resolution picker system may receive a chip and align the picker with the chip, for example, using fiducial markers and/or reference wells. The picker may pick, for example, cells growing in microwells on the chip into, for example, 96- or 384-well plates containing growth media. The picker may include a single picking pin or a plurality of picking pins.

A high resolution picker system may receive a membrane and align the picker with the membrane, for example, using reference well marks on the membrane. The picker may pick, for example, cells from the membrane into, for example, 96- or 384-well plates containing growth media. The picking pin(s) may have a different shape (e.g., mushroom-shaped) and/or surface (e.g., texture) for picking from a membrane. The system also may include one or more mechanisms (e.g., a floating pin and/or vacuum) to hold and/or flatten the membrane.

A high resolution picker system may enable chip replication via a chip-to-chip transfer. The picker may receive and align a first chip based on fiducial markers and/or reference wells. The picker also may receive and align a second chip based on fiducial markers and/or reference wells. The picker may transfer, for example, cells growing in microwells on the first chip to microwells on the second chip.

A high throughput system for automatically picking a target species of a plurality of species of at least one biological entity cultivated in a microfabricated device may include a port for receiving the microfabricated device. The microfabricated device defines a high density array of microwells. Each microwell of the high density array of microwells is configured to isolate and cultivate at least one species of the at least one biological entity and includes at least one tag of a plurality of unique tags. Each tag of the plurality of unique tags includes a nucleic acid molecule, which includes a target-specific nucleotide sequence for annealing to the at least one biological entity and a location-specific nucleotide sequence correlating to at least one microwell of the high density array of microwells. The system also includes a high-resolution picking apparatus with at least one protrusion for picking the at least one biological entity from at least one microwell of the high density array of microwells. The system further includes an input device for receiving an indication of at least one target-specific nucleotide sequence and at least one processor communicatively coupled to the input device and the high-resolution picking apparatus. The at least one processor acquires the indication of the at least one target-specific nucleotide sequence from the input device, compares the at least one target-specific nucleotide sequence to the plurality of unique tags, determines at least one microwell of the high density array of microwells including the target species based on the comparison, and controls the high-resolution picking apparatus to pick the at least one biological entity from the at least one determined microwell of the high density array of microwells.

A high throughput system is disclosed for automatically picking a target species of a plurality of species of at least one biological entity cultivated in a microfabricated device. The microfabricated device defines a high density array of microwells, each microwell of the high density array of microwells being associated with at least one unique primer of the plurality of unique primers. The system includes a port for receiving a membrane removed from the microfabricated device, the membrane having sealed each microwell of the high density array of microwells to retain the at least one biological entity in the high density array of microwells, such that portions of the at least one biological entity corresponding to the high density array of microwells remain attached to the membrane following removal of the membrane. The system also includes a high-resolution picking apparatus including at least one protrusion for picking the at least one biological entity from at least one membrane location corresponding to at least one microwell of the high density array of microwells, an input device for receiving an indication of at least one target-specific nucleotide sequence associated with the target species, and at least one processor communicatively coupled to the input device and the high-resolution picking apparatus. The at least one processor acquires the indication of the at least one target-specific nucleotide sequence from the input device, compares the at least one target-specific nucleotide sequence to the plurality of unique tags, determines at least one membrane location corresponding to at least one microwell of the high density array of microwells comprising the target species based on the comparison, and controls the high-resolution picking apparatus to pick the portions of the at least one biological entity from the at least one determined membrane location.

The above-described embodiments can be implemented in any of numerous ways. For example, embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Further Examples

A microfabricated device may include a substrate with a series of functional layers. The series of functional layers includes a first functional layer defining a first array of experimental units (e.g., wells) and at least one subsequent functional layer defining a subsequent array of experimental units (e.g., microwells) in each experimental unit of the preceding functional layer. Each of the experimental units may be configured to receive and grow at least one cell, perform at least one screen, and/or test at least one nutrient.

In an embodiment, an apparatus for screening different conditions against a matrix of cells includes a substrate. The substrate includes a first surface. The surface defines a first array of wells. Each well includes an inner surface. Each inner surface defines a second array of microwells. Each microwell is configured to receive and grow at least one cell.

In an embodiment, an apparatus for screening different conditions against a matrix of cells includes a substrate with a series of functional layers. The series of functional layers includes a first functional layer defining a first array of experimental units and at least one subsequent functional layer defining a subsequent array of experimental units in each experimental unit of the preceding functional layer. Each of the experimental units is configured to receive and grow at least one cell.

In an embodiment, a method is disclosed for segregating cells in a substrate including a first surface. The first surface defines a first array of experimental units. Each experimental unit is configured to receive at least one cell. At least a portion of each experimental unit is configured with first surface characteristics that include attracting cells and/or increasing cellular tendency to occupy the experimental unit. Alternatively or in addition, at least a portion of the first surface may be configured with second surface characteristics that include repelling cells and/or reducing cellular tendency to stick to the first surface. The method also includes applying a composition including cells to the first surface such that at least one cell occupies at least one experimental unit.

In an embodiment, a method for sampling a cell population in a substrate includes sampling a population of cells in at least one microwell by applying a picking device to a first surface of the substrate. The device includes at least one protrusion facing the first surface. The at least one protrusion has a diameter less than the opening diameter of each microwell. The at least one protrusion is inserted into at least one microwell holding a population of cells such that a portion of the population of cells in the at least one microwell adheres and/or attaches to the at least one protrusion. The method also includes withdrawing a sample of the population of cells in the at least one microwell by removing the device from the first surface of the substrate such that the portion of the population of cells in the at least one microwell remains adhered and/or attached to the at least one protrusion.

In an embodiment, a method for sampling a cell population in a substrate includes sampling a population of cells in at least one experimental unit by applying a picking device to a first surface of the substrate. The device includes at least one protrusion facing the first surface. The at least one protrusion has a diameter less than the opening diameter of each microwell. The at least one protrusion is inserted into at least one experimental unit holding a population of cells such that a portion of the population of cells in the at least one experimental unit adheres and/or attaches to the at least one protrusion. The method also includes withdrawing a sample of the population of cells in the at least one experimental unit by removing the device from the first surface of the substrate such that the portion of the population of cells in the at least one experimental unit remains adhered and/or attached to the at least one protrusion.

In an embodiment, a method for sampling a cell population in a substrate including a first surface and a second surface opposite the first surface, the first surface defining a first array of microwells, includes applying a picking device to the second surface of the substrate. The device includes at least one protrusion facing the second surface. The at least one protrusion has a diameter about equal to or less than the diameter of each microwell. The at least one protrusion is pushed against the second surface at a location corresponding to at least one microwell holding a population of cells and/or inserted into the at least one microwell holding the population of cells such that a portion of the population of cells in the at least one microwell is displaced above the inner surface of the well and/or the first surface of the substrate. The method also includes sampling the population of cells in the at least one microwell by collecting the displaced portion of the population of cells.

In an embodiment, a method for sampling a cell population in a substrate including a first surface and a second surface opposite the first surface, the first surface defining a first array of experimental units, includes applying a picking device to the second surface of the substrate. The device includes at least one protrusion facing the second surface. The at least one protrusion has a diameter about equal to or less than a diameter of at least one experimental unit. The at least one protrusion is pushed against the second surface at a location corresponding to the at least one experimental unit holding a population of cells and/or inserted into the at least one experimental unit holding the population of cells such that a portion of the population of cells in the at least one experimental unit is displaced above the first surface of the substrate. The method also includes collecting the displaced portion of the population of cells.

In an embodiment, a method for sampling a cell population in a substrate including a first surface, the first surface defining a first array of wells, each well having an inner surface defining a second array of microwells, each microwell having an opening diameter, includes applying a picking device to the first surface of the microfabricated substrate. The device includes at least one protrusion facing the first surface. The at least one protrusion has a diameter less than the diameter of each microwell. The at least one protrusion is inserted into at least one microwell holding a population of cells such that a portion of the population of cells in the at least one microwell is volume displaced above at least one of the inner surface of the well and the first surface of the substrate. The method also includes sampling the population of cells in the at least one microwell by collecting the volume displaced portion of the population of cells.

In an embodiment, a method for sampling a cell population in a substrate including a first surface, the first surface defining a first array of experimental units, includes applying a picking device to the first surface of the microfabricated substrate. The device includes at least one protrusion facing the first surface. The at least one protrusion has a diameter less than a diameter of at least one experimental unit. The at least one protrusion is inserted into the at least one experimental unit holding a population of cells such that a portion of the population of cells in the at least one experimental unit is volume displaced above the first surface of the substrate. The method also includes sampling the population of cells in the at least one experimental unit by collecting the volume displaced portion of the population of cells.

In an embodiment, a method for sampling a cell population in a substrate including a first surface defining a first array of wells, each well including an inner surface, each inner surface defining a second array of microwells, each microwell having an opening diameter, includes sampling a population of cells in at least one microwell by applying a picking device to the first surface of the substrate. The device includes at least one needle and/or nanopipette facing the first surface. The at least one needle and/or nanopipette has an external diameter less than the opening diameter of each microwell and an internal diameter capable of accommodating a target cell diameter. The at least one needle and/or nanopipette is inserted into at least one microwell holding a population of cells. The method also includes withdrawing a sample of the population of cells in the at least one microwell by using pressure to pull a portion of the population of cells from the at least one microwell into the device.

In an embodiment, a method for sampling a cell population in a substrate includes a first surface defining a first array of experimental units, includes sampling a population of cells in at least one microwell by applying a picking device to the first surface of the substrate. The device includes at least one needle and/or nanopipette facing the first surface. The at least one needle and/or nanopipette has an external diameter less than the opening diameter of each microwell and an internal diameter capable of accommodating a target cell diameter. The at least one needle and/or nanopipette is inserted into at least one experimental unit holding a population of cells. The method also includes withdrawing a sample of the population of cells in the at least one experimental unit by using pressure to pull a portion of the population of cells from the at least one experimental unit into the device.

In an embodiment, a method for sampling a cell population in a substrate including a first surface defining a first array of wells, each well including inner surface defining a second array of microwells, includes sampling a population of cells in fluid in at least one microwell by applying focused acoustic energy to at least one microwell holding a population of cells in fluid. The focused acoustic energy is applied in a manner effective to eject a droplet from the at least one microwell. The droplet includes a sample of the population of cells in the at least one microwell.

In an embodiment, a method for sampling a cell population in a substrate including a first surface defining a first array of experimental units includes sampling a population of cells in fluid in at least one experimental unit by applying focused acoustic energy to at least one experimental unit holding a population of cells in fluid, the focused acoustic energy being applied in a manner effective to eject a droplet from the at least one experimental unit. The droplet includes a sample of the population of cells in the at least one experimental unit.

In an embodiment, a substrate includes a first surface and a second surface. The first surface defines a first array of wells. Each well has an inner surface defining a second array of microwells. The substrate includes at least a first piece including at least a portion of the first surface and a second piece including at least a portion of the second surface. The first piece and the second piece are detachably connected along at least a portion of a plane parallel to the first surface and the second surface. The plane divides the second arrays of microwells. The first array and/or the second array may be substantially planar. A method for sampling a cell population in at least one microwell includes detaching the first piece and the second piece such that a first portion of the population of cells in the at least one microwell remains attached to the first piece and a second portion of the population of cells in the at least one microwell remains attached to the second piece.

In an embodiment, a substrate includes a first surface and a second surface. The first surface defines a first array of experimental units. The substrate includes at least a first piece including at least a portion of the first surface and a second piece including at least a portion of the second surface. The first piece and the second piece are detachably connected along at least a portion of a plane parallel to the first surface and the second surface. The plane divides the first array of experimental units. The first array may be substantially planar. The experimental units may be wells. A method for sampling a cell population in at least one experimental unit includes detaching the first piece and the second piece such that a first portion of the population of cells in the at least one experimental unit remains attached to the first piece and a second portion of the population of cells in the at least one experimental unit remains attached to the second piece.

In an embodiment, a substrate includes a first surface defining a first array of wells, each well including an inner surface, each inner surface defining a second array of microwells. A detachable membrane is applied to at least a portion of at least one inner surface such that a portion of the population of cells in at least one microwell attaches to the detachable membrane. A method of sampling the population of cells in the at least one microwell includes peeling back the detachable membrane such that the portion of the population of cells in the at least one microwell remains attached to the detachable membrane.

In an embodiment, a substrate includes a first surface defining a first array of experimental units. A detachable membrane is applied to at least a portion of the first surface such that a portion of the population of cells in at least one experimental unit attaches to the detachable membrane. A method of sampling the population of cells in the at least one experimental unit includes peeling back the detachable membrane such that the portion of the population of cells in the at least one experimental unit remains attached to the detachable membrane.

In an embodiment, a substrate includes a first surface and a second surface. The first surface defines a first array of wells. Each well has an inner surface, each inner surface defining a second array of microchannels. Each microchannel has a first opening in the first surface and a second opening in the second surface. A first detachable membrane is applied to at least a portion of at least one inner surface such that at least some of the population of cells in at least one microchannel attach to the first detachable membrane. A second detachable membrane is applied to at least a portion of the second surface such that at least some of the population of cells in at least one microchannel attach to the second detachable membrane. A method of sampling the population of cells in the at least one microchannel includes peeling back the first detachable membrane such that the at least some of the population of cells in the at least one microchannel remain attached to the first detachable membrane and/or the second detachable membrane such that the at least some of the population of cells in the at least one microchannel remain attached to the second detachable membrane.

In an embodiment, a substrate includes a first surface and a second surface. The first surface defines a first array of experimental units. Each experimental unit has a first opening in the first surface and a second opening in the second surface. A first detachable membrane is applied to at least a portion of the first surface such that at least some of the population of cells in at least one experimental unit attach to the first detachable membrane. A second detachable membrane is applied to at least a portion of the second surface such that at least some of the population of cells in at least one experimental unit attach to the second detachable membrane. A method of sampling the population of cells in the at least one experimental unit includes peeling back the first detachable membrane such that the at least some of the population of cells in the at least one experimental unit remain attached to the first detachable membrane and/or the second detachable membrane such that the at least some of the population of cells in the at least one experimental unit remain attached to the second detachable membrane.

In an embodiment, a method for culturing cells in a sample derived from an environment includes applying the sample to the first surface of a substrate such that at least one cell occupies at least one microwell, well, or experimental unit, applying a semi-permeable membrane to at least a portion of the first surface such that a nutrient can diffuse into the at least one microwell, well, or experimental unit and escape of the at least one occupying cell from the at least one microwell, well, or experimental unit is prevented and/or mitigated, and incubating the at least once occupying cell in the at least one microwell, well, or experimental unit with at least one nutrient.

In an embodiment, a method for culturing and adaptation of cells in a sample derived from an environment in a substrate includes applying the sample to the first surface of the substrate such that at least one cell occupies at least one microwell, well, or experimental unit, applying a semi-permeable membrane to at least a portion of the first surface such that a nutrient can diffuse into the at least one microwell, well, or experimental unit and escape of the at least one occupying cell from the at least one microwell, well, or experimental unit is prevented and/or mitigated, incubating the at least one occupying cell in the at least one microwell, well, or experimental unit with at least one nutrient, gradually transitioning over a period of time from the at least one nutrient to at least one alternative nutrient formulation using progressive partial exchange, and detecting growth of the at least one occupying cell in the at least one microwell, well, or experimental unit.

In some embodiments, pooled molecular assay data elements may be assigned and/or correlated back to individual locations of origin. In an embodiment, microarray includes a plurality of locations for applying a sample. Each location on a microarray may be configured to receive a portion of the sample. Each location is marked with a unique tag capable of identifying from which location a portion of the sample came after that portion of the sample is removed from the microarray.

In an embodiment, a method of identifying from which location on a microarray a portion of a sample comprising at least one nucleic acid molecule came, after that portion of the sample is removed from the microarray, includes the step of (a) applying one or more portions of the sample onto one or more of a plurality of locations on the microarray. Each location is marked with a unique tag comprising a nucleic acid molecule. The nucleic acid molecule includes (i) a location-specific nucleotide sequence; and (ii) a first target-specific nucleotide sequence. The method also includes the step of (b) allowing the nucleic acid molecule found in at least one portion of the sample to anneal to a tag marking a location. The method further includes the step of (c) performing primer extension, reverse transcription, single-stranded ligation, or double-stranded ligation on the population of annealed nucleic acid molecules, thereby incorporating a location-specific nucleotide sequence into each nucleic acid molecule produced by primer extension, reverse transcription, single-stranded ligation, or double-stranded ligation. The method further includes the steps of (d) combining the population of nucleic acid molecules produced in step (c); (e) sequencing the population of combined nucleic acid molecules, thereby obtaining the sequence of one or more location-specific nucleotide sequences; and (f) correlating the sequence of at least one location-specific nucleotide sequence obtained from the population of combined nucleic acid molecules to the location on the microarray marked with a tag including the location-specific nucleotide sequence, thereby identifying from which location on a microarray a portion of a sample comprising at least one nucleic acid molecule came. The sample may include at least one cell, and the cell may replicate after step (a) and before step (b). A portion of the portion of the sample may be removed from at least one location before step (b), and said portion of the portion of the sample may be stored in a separate receptacle correlated to the original location of the portion of the sample on the microarray.

In an embodiment, a method of manufacturing a microarray with a plurality of locations for applying a sample, wherein at least one location is marked with a unique tag, includes the step of (a) synthesizing a plurality of tags. Each tag includes a nucleic acid molecule including: (i) a location-specific nucleotide sequence; and (ii) a first target-specific nucleotide sequence. The method further comprises the step of (b) placing a tag on at least one location of the plurality of locations on the microarray. A unique tag may include a nucleic acid molecule including (i) a location-specific nucleotide sequence; and (ii) a first target-specific nucleotide sequence. The tag further may include an amplification primer binding site and/or an adapter nucleotide sequence.

A microfabricated device may be manufactured, via injection molding, using cyclic olefin polymer. The substrate or chip may have a substantially planar surface with dimensions of about 1 inch by about 3 inches. The surface further may define about 200,000 wells, each well having a diameter of about 50 μm. Alternatively, the surface may define about 800,000 microwells, each microwell having a diameter of about 25 μm. The surface may be treated with a corona plasma treatment to make it more hydrophilic.

Microorganisms (e.g., bacteria) isolated from soil may be diluted into soil extract nutrient and applied to the surface of the chip. Next, a membrane may be applied to the surface of the chip. The membrane may be, for example, a hydrogel layer. The membrane may be reversibly or irreversibly attached or affixed to the chip using, for example, lamination. Then, a second device may be placed on first of the membrane and surface of the chip to divide the surface of the chip into partitions. Each partition of the surface has some subset of the wells or microwells therein.

In an on-chip adaptation, each partition may be loaded with an environmentally-derived nutrient media. During an incubation period, the chip may be monitored to observe bacterial growth using, for example, an optical system to detect differences as bacteria grow in microwells. Over time, the nutrient media may be slowly adjusted until it is a fully formulated media that can be used to grow the bacteria in a laboratory environment.

In an off-chip adaptation, any wells or microwells where bacterial growth is observed may be sampled. The bacteria samples may be transferred to, for example, a plate, second chip, or a traditional tool like a petri dish for adaptation to formulated media.

Some embodiments may be used for optimizing media. For example, a single species of bacteria may be applied to a surface of the chip. Next, a membrane may be applied to the surface of the chip. The membrane may be, for example, a hydrogel layer. The membrane may be reversibly or irreversibly connected to or affixed to the chip using, for example, lamination. Then, a second device may be placed on top of the membrane and/or surface of the chip to divide the membrane and/or surface of the chip into partitions. Each partition of the membrane and/or surface has some subset of the wells or microwells underlying the membrane and/or thereon the surface. Each partition may be loaded with a different medium (e.g., derived from a different environment). During an incubation period, the chip may be monitored to observe growth rates in the wells or microwells with different nutrient formulations.

Some embodiments may be used for screening for microbes that solubilize phosphate, particularly for agricultural applications. Phosphorus is a major essential macronutrient for plants. Soil phosphorus may be managed to optimize crop production and is applied to soil in the form of phosphate fertilizers. However, a large portion of soluble inorganic phosphate, which is applied to the soil as chemical fertilizer, is immobilized rapidly and becomes unavailable to plants. Phosphate solubilizing bacteria strains hydrolyze organic and inorganic phosphorus from insoluble compounds, and may be used to improve plant growth and yield. A sample that includes microbes may be derived from an environment, such as soil (particularly if organic and inorganic phosphorus are being effectively hydrolyzed from insoluble compounds in the environment). According to an embodiment, the sample may be loaded onto a surface of a substrate with at least one array of experimental units such that at least some of the microbes occupy a plurality of the experimental units. The occupying microbes may be incubated in the plurality of experimental units with different forms of phosphate and compared/screened for their ability to hydrolyze the different forms of phosphate.

Some embodiments may be used for screening for mutants that have higher growth rates. A sample of microorganisms (e.g., bacteria) may be derived from a single lab culture that has been treated with a mutagen. According to an embodiment, the sample may be loaded onto a surface of a substrate with at least one array of experimental units such that at least some of the bacteria occupy a plurality of the experimental units. The occupying bacteria may be incubated in the plurality of experimental units with at least one nutrient and observed/compared to identify the experimental unit(s) with higher growth rates.

Some embodiments may be used for identifying, for example, novel antibiotics, antifungals, or anti-viral compounds. A sample that includes microorganisms (e.g., bacteria) may be derived from an environment. According to an embodiment, the sample may be loaded onto a surface of a substrate with at least one array of experimental units such that at least some of the bacteria occupy a plurality of the experimental units. The occupying bacteria are grown in the plurality of experimental units for a period of time, then a layer of indicator bacteria is grown on first of the occupying bacteria (this may require a thin layer of agar). Experimental units that produce clear plaques in the layer of indicator bacteria indicate antibiotic production.

Some embodiments may be used for screening for a particular enzyme activity. According to an embodiment, a sample including cells may be loaded onto a surface of a substrate with at least one array of experimental units such that at least one of the cells occupies a plurality of the experimental units. The occupying cells are grown in the plurality of experimental units for a period of time, then a substrate that produces a color when cleaved by the enzyme is added. Experimental units that produce this color reaction indicate the desired enzyme activity.

Some embodiments may be used for screening for microorganisms that perform bioremediation, particularly for environmental clean-up applications. Pollution and environmental contamination is complex. For example, the effects of an oil spill or other release of liquid petroleum hydrocarbon into an environment depends upon many factors. In a marine environment, the type(s) of oil, the temperature(s) of the water, and the type(s) of shoreline all affect cleanup. A sample that includes microorganisms may be derived from an environment, such as oil-bearing rock formations. According to an embodiment, the sample may be loaded onto a surface of a substrate with at least one array of experimental units such that at least some of the microorganisms occupy a plurality of the experimental units. The occupying microorganisms may be incubated in the plurality of experimental units with different types of oil and compared/screened for their ability to remove or neutralize the oil.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method comprising obtaining a microfabricated device defining a high density array of microwells for cultivating at least one cell from a sample, at least one microwell of the high density array of microwells comprising the at least one cell and at least one unique tag to identify the at least one microwell of the high density array of microwells in which at least one species of the at least one cell is cultivated, the at least one unique tag comprising a nucleic acid molecule, the nucleic acid molecule comprising:

a target-specific nucleotide sequence for annealing to a target nucleic acid fragment present in at least one species of interest of the at least one cell; and a location-specific nucleotide sequence for identifying the at least one microwell of the high density array of microwells;

incubating the microfabricated device to grow a plurality of cells from the at least one cell in the at least one microwell of the high density array of microwells;

splitting the plurality of cells in the at least one microwell of the high density array of microwells into a first portion of the plurality of cells and a second portion of the plurality of cells, the at least one unique tag remaining with at least the first portion of the plurality of cells;

analyzing the first portion of the plurality of cells to:
determine the at least one species of interest; and
identify the at least one microwell of the high density array of microwells in which the at least one species of interest was cultivated based on the at least one unique tag; and based on identifying the at least one microwell of the high density array of microwells in which the at least one species of interest was cultivated, locating the at least one species of interest within the second portion of the plurality of cells.

2. The method of claim 1, further comprising picking at least one cell of the at least one species of interest from the second portion of the plurality of cells.

3. The method of claim 1, wherein:
the at least one unique tag comprises a first unique tag and a second unique tag; the first unique tag comprises a first location-specific nucleotide sequence predetermined to identify a first dimension of microwells in the high density array of microwells;
the second unique tag comprises a second location-specific nucleotide sequence predetermined to identify a second dimension of microwells in the high density array of microwells; and
the first location-specific nucleotide sequence and the second location-specific nucleotide sequence together identify the at least one microwell of the high density array of microwells.

4. The method of claim 3, wherein:
the first unique tag comprises a first target-specific nucleotide sequence comprising a forward polymerase chain reaction (PCR) primer; and
the second unique tag comprises a second target-specific nucleotide sequence comprising a reverse PCR primer.

5. The method of claim 1, wherein obtaining the microfabricated device comprises disposing the at least one unique tag in the at least one microwell of the high density array of microwells.

6. The method of claim 1, wherein obtaining the microfabricated device comprises loading the sample comprising the at least one cell on the microfabricated device.

7. The method of claim 1, wherein obtaining the microfabricated device comprises applying a membrane to retain the at least one cell in the at least one microwell of the high density array of microwells.

8. The method of claim 7, wherein the membrane is at least one of permeable only by gas and impermeable.

9. The method of claim 7, wherein the membrane allows diffusion of a nutrient medium into the at least one microwell of the high density array of microwells.

10. The method of claim 7, wherein splitting the plurality of cells in the at least one microwell of the high density array of microwells comprises removing the membrane from at least one microwell of the high density array of microwells such that the first portion of the plurality of cells remains in the at least one microwell of the high density array of microwells and the second portion of the plurality of cells remains connected to a surface of the membrane.

11. The method of claim 10, wherein locating the at least one species of interest within the second portion of the plurality of cells comprises identifying an area on the surface of the membrane corresponding to the at least one microwell of the high density array of microwells in which the at least one species of interest was cultivated.

12. The method of claim 7, wherein splitting the plurality of cells in the at least one microwell of the high density array of microwells comprises removing the membrane from the at least one microwell of the high density array of microwells such that the first portion of the plurality of cells remains connected to a surface of the membrane and the second portion of the plurality of cells remains in the at least one microwell of the high density array of microwells.

13. The method of claim 1, wherein analyzing the first portion of the plurality of cells to determine a presence or an absence of the at least one species of interest comprises performing a polymerase chain reaction (PCR) on the first portion of the plurality of cells to amplify any of the target nucleic acid fragment present in the first portion of the plurality of cells based on the target-specific nucleotide sequence of the at least one unique tag.

14. The method of claim 13, wherein analyzing the first portion of the plurality of cells to determine a presence or an absence of the at least one species of interest further comprises sequencing any PCR-amplified target nucleic acid fragments.

15. The method of claim 14 wherein the sequencing comprises performing next generation sequencing (NGS).

16. The method of claim 1, further comprising supplying at least one nutrient for cultivating the at least one species of the at least one cell.

17. The method of claim 16, wherein the at least one nutrient for cultivating the at least one species of the at least one cell comprises at least one of:
an extract from a natural environment of the at least one species of the at least one cell;
a medium derived from the natural environment of the at least one species of the at least one cell;
a medium formulated to resemble the natural environment of the at least one species of the at least one cell;
a selective medium to cultivate only the at least one species of the at least one cell; and
a differential medium to distinguish the at least one species of the at least one cell.

18. The method of claim 17, wherein the natural environment of the at least one species of the at least one cell is at least one of a biological tissue, a biological product, a microbial suspension, air, soil, sediment, living organic matter, forage, petroleum, sewage, and water.

19. The method of claim 1, wherein the at least one cell includes at least one of an Archaea cell, a Bacteria cell, and a Eukaryota cell.

20. The method of claim 1, wherein the at least one species of interest is selected based on at least one of a nucleic acid and a gene.

21. The method of claim 1, further comprising:
picking the at least one cell of the at least one species of interest from the second portion of the plurality of cells.

22. A method comprising:
obtaining a microfabricated device defining a high density array of microwells for cultivating at least one cell from a sample, at least one microwell of the high density array of microwells comprising at least one unique tag to identify the at least one microwell of the high density array of microwells in which at least one species of the at least one cell is cultivated, the at least one unique tag comprising a nucleic acid molecule, the nucleic acid molecule comprising: a target-specific nucleotide sequence for annealing to a target nucleic acid fragment present in at least one species of interest of the at least one cell; and a location-specific nucleotide sequence predetermined to identify the at least one microwell of the high density array of microwells;

preparing and loading the sample on the microfabricated device such that no more than one cell of the at least one cell is disposed in each microwell of a preponderance of the high density array of microwells; and determining, based on the at least one unique tag:
- a first number of microwells of the high density array of microwells comprising at least one cell;
- a second number of microwells of the high density array of microwells comprising the at least one species of interest from the sample; and
- based on the first number and the second number, a relative abundance of the at least one species of interest in the sample.

23. The method of claim 22, further comprising determining:
- a total number of cells from the sample; and
- based on the total number of cells in the sample and the relative abundance of the at least one species of interest in the sample, an absolute abundance of the at least one species of interest in the sample.

24. A method comprising:
obtaining a microfabricated device defining a high density array of experimental units for cultivating at least one biological entity from a sample, at least one experimental unit of the high density array of experimental units comprising the at least one biological entity and at least one unique tag to identify spatial information relating to the at least one experimental unit of the high density array of experimental units in which at least one type of the at least one biological entity is cultivated, the at least one unique tag comprising a first binding molecule, the first binding molecule comprising:
- a target-specific component for binding to a biomolecule present in the at least one type of interest of the at least one biological entity; and
- a location-specific component for identifying the spatial information relating to the at least one experimental unit of the high density array of experimental units,
- wherein the at least one biological entity is at least one of an organism, a cell, a cell component, a cell product, and a virus, and
- wherein the first binding molecule is at least one of a protein, a nucleic acid, a carbohydrate, a lipid, and a drug;

incubating the microfabricated device to grow a plurality of biological entities from the at least one biological entity in the at least one experimental unit of the high density array of experimental units; and analyzing the plurality of biological entities in the at least one experimental unit of the high density array of experimental units to:
- determine the at least one type of interest of the at least one biological entity; and
- identify the spatial information relating to the at least one experimental unit of the high density array of experimental units in which the at least one type of interest of the at least one biological entity was cultivated based on the at least one unique tag.

* * * * *

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: unique molecular identifier tag
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t
```

-continued

```
<400> SEQUENCE: 1
nnnannncnn ntnnngnnna nnncnnn                                              27

<210> SEQ ID NO 2
<211> LENGTH: 11
<212> TYPE: DNA
<213> ORGANISM: Artificial Sequence
<220> FEATURE:
<223> OTHER INFORMATION: exemplary sequence of isolated strain of
      cultivated cell

<400> SEQUENCE: 2
actgtcagta g                                                               11

<210> SEQ ID NO 3
<211> LENGTH: 11
<212> TYPE: DNA
<213> ORGANISM: Artificial Sequence
<220> FEATURE:
<223> OTHER INFORMATION: exemplary sequence of isolated strain of
      cultivated cell

<400> SEQUENCE: 3
tagcctagta a                                                               11

<210> SEQ ID NO 4
<211> LENGTH: 11
<212> TYPE: DNA
<213> ORGANISM: Artificial Sequence
<220> FEATURE:
<223> OTHER INFORMATION: exemplary sequence of isolated strain of
      cultivated cell

<400> SEQUENCE: 4
acgtagggtc a                                                               11

<210> SEQ ID NO 5
<211> LENGTH: 11
<212> TYPE: DNA
<213> ORGANISM: Artificial Sequence
<220> FEATURE:
<223> OTHER INFORMATION: exemplary sequence of isolated strain of
      cultivated cell

<400> SEQUENCE: 5
gtcagtcaat g                                                               11

<210> SEQ ID NO 6
<211> LENGTH: 11
<212> TYPE: DNA
<213> ORGANISM: Artificial Sequence
<220> FEATURE:
<223> OTHER INFORMATION: exemplary sequence of isolated strain of
      cultivated cell

<400> SEQUENCE: 6
ctaatcggat c                                                               11
```